US009511050B2

(12) United States Patent
Toretsky et al.

(10) Patent No.: US 9,511,050 B2
(45) Date of Patent: Dec. 6, 2016

(54) METHODS AND COMPOSITIONS FOR TREATING CANCER

(71) Applicant: GEORGETOWN UNIVERSITY, Washington, DC (US)

(72) Inventors: Jeffrey A. Toretsky, Silver Spring, MD (US); Aykut Uren, Rockville, MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 15/030,713

(22) PCT Filed: Oct. 20, 2014

(86) PCT No.: PCT/US2014/061418
§ 371 (c)(1),
(2) Date: Apr. 20, 2016

(87) PCT Pub. No.: WO2015/061229
PCT Pub. Date: Apr. 30, 2015

(65) Prior Publication Data
US 2016/0263086 A1    Sep. 15, 2016

Related U.S. Application Data

(60) Provisional application No. 61/895,308, filed on Oct. 24, 2013.

(51) Int. Cl.
*A61K 31/405* (2006.01)
*A61K 31/404* (2006.01)
*A61K 45/06* (2006.01)
*A61K 47/40* (2006.01)

(52) U.S. Cl.
CPC ............ *A61K 31/404* (2013.01); *A61K 45/06* (2013.01); *A61K 47/40* (2013.01)

(58) Field of Classification Search
CPC .................................................. C07D 209/08
USPC ...................................................... 514/415
See application file for complete search history.

(56) References Cited

U.S. PATENT DOCUMENTS

| | | | |
|---|---|---|---|
| 6,969,729 B2 | 11/2005 | Jensen | |
| 8,232,310 B2 | 7/2012 | Toretsky et al. | |
| 8,232,410 B2 | 7/2012 | Ojima et al. | |
| 9,045,415 B2 | 6/2015 | Toretsky et al. | |
| 9,290,449 B2 | 3/2016 | Toretsky et al. | |
| 2005/0288244 A1 | 12/2005 | Manoharan et al. | |
| 2010/0004179 A1 | 1/2010 | Toretsky | |
| 2010/0167994 A1 | 7/2010 | Toretsky et al. | |
| 2013/0259927 A1 | 10/2013 | Nemunaitis | |
| 2015/0051260 A1 | 2/2015 | Toretsky et al. | |
| 2015/0329488 A1 | 11/2015 | Toretsky et al. | |

FOREIGN PATENT DOCUMENTS

| | | |
|---|---|---|
| CN | 1365972 A | 8/2002 |
| EP | 0133244 A2 | 2/1985 |
| WO | WO 03/000925 A1 | 1/2003 |
| WO | WO 2006/117414 A1 | 11/2006 |
| WO | WO 2008/083326 | 7/2008 |
| WO | WO 2013/155341 | 10/2013 |

OTHER PUBLICATIONS

International Search Report and Written Opinion issued in PCT/US2014/061418 dated Jan. 28, 2015.
Erkizan, H.V., et al., A small molecule blocking oncogenic protein EWS-FLI1 interaction with RNA helicase A inhibits growth of Ewing's sarcoma, Nature15(7): 750 (2009).
Lambert, G., et al., EWS Fli-1 Antisense nanocapsules inhibits Ewing sarcoma-related tumor in mice Biochem Biophys Res Comm 279(2): 401 (2000).
Abaan et al., "PTPL1 is a direct transcriptional target of EWS-FLI1 and modulates Ewing's sarcoma tumorigenesis", Oncogene (2005) 24(16): 2715-2722.
Anderson et al., "BRCA1 protein is linked to the RNA polymerase II holoenzyme complex via RNA helicase A", Nat Genet (1998) 19(3):254-256.
Ankhiwala, Studies in Spiroheterocycles. Synthesis and Antimicrobial Activities of Some New Spiro (indoline-3, 5'-pyrazonlin)-1'-phenyl-2-ones and Spiro ( . . . J Indian Chem Soc. (1990) 67: 432-434.
Babu et al., "Heteropolyacid-silica mediated [3+2] cycloaddition of ylides—a facile multicomponent one-pot synthesis of novel dispiroheterocycles", Tetrahedron Ltt. (2006) 47(52): 9221-9225.
Baer et al., "Profiling and functional annotation of mRNA gene expression in pediatric rhabdomyosarcoma and Ewing's sarcoma", Int J Cancer (2004) 110(5):687-694.
Bayoumy et al., "Studies on Spiroheterocyclic Nitrogen Compounds. Part 1: Synthesis of Some New Spiro Pyrazolines, Isoxazolines and Pyrimidinethiones Containing Benzanilide Moiety", J Indian Chem Soc. (1984) LXI(1):520-522.
Beccalli et al., "Synthesis of [a]annulated carbazoles from indol-2,3-dione." Tetrahedron (1993) 49(21): 4741-4758.
Berg et al., "Small-molecule antagonists of Myc/Max dimerization inhibit Myc-induced transformation of chicken embryo fibroblasts", Proc Natl Acad Sci U S A (2002) 99(6):3830-3835.
Bhalla et al., "Local flexibility in molecular function paradigm", Mol Cell Proteomics (2006) 5:1212-1223.
Bowdish et al., "Immunomodulatory properties of defensins and cathelicidins", Curr Top Microbiol Immunol (2006) 306:27-66.
Braun et al., "Identification of target genes for the Ewing's sarcoma EWS/FLI fusion protein by representational difference analysis", Mol Cell Biol (1995) 15(8):4623-4630.
Carter et al., "Chemotherapy of Cancer", 2nd Edition; John Wiley & Sons, New York (1981), Appendix C—Drug-Tumor Interactions; 5 pages.
Castillero-Trejo et al., "Expression of the EWS/FLI-1 oncogene in murine primary bone-derived cells results in EWS/FLI-1-dependent, Ewing sarcoma-like tumors", Cancer Res (2005) 65(19):8698-8705.

(Continued)

*Primary Examiner* — Raymond Henley, III
(74) *Attorney, Agent, or Firm* — Knobbe, Martens, Olson & Bear LLP

(57) ABSTRACT

Methods and compositions provided herein relate to the treatment of cancer. In some embodiments, the compositions have utility in the treatment of cancers including glioblastoma multiforme and lung cancer.

20 Claims, 38 Drawing Sheets

(56) References Cited

OTHER PUBLICATIONS

Chen et al., "Specific alterations of U1-C protein or U1 small nuclear RNA can eliminate the requirement of Prp28p, an essential DEAD box splicing factor", Mol Cell (2001) 7(1):227-232.

Cheng et al., "Rational drug design via intrinsically disordered protein", Trends Biotechnol. (2006) 24(10):435-442.

Dandia et al., "Investigation of the Reactions of some New Fluorine containing 3-Aroylmethylene-indol-2-ones with Urea and Thiourea Derivatives", J Indian Chem Soc., (Nov. 1995) 72: 833-835.

Dandia et al., "Facile One Pot Microwave Induced Solvent-Free Synthesis and Antifungal, Antitubercular Screening of Spiro [1,5]-Benzothiazepin-2,3'[3'$H$]indol-2[1'$H$]ones", Chem Pharm Bull (2003) 51(10): 1137-1141.

Database accession No. CID 359736, 3-[2-(4-Amino-phenyl)-2-oxo-ethyl]-3-hydroxy-1,3-dihydro-indol-2-one—Compound Summary; (Mar. 26, 2005) XP-002717179; Database PubChem Compound; pp. 1-5.

Database accession No. CID 326411; NSC297830—Compound summary; XP-002717181; (Mar. 26, 2004) Database PubChem Compound; pp. 1-5.

Database accession No. RN 362506-54-5; XP-002745329; (Oct. 16, 2001) Supplier: ChemBridge Corporation; 1 page.

Database accession No. RN 362507-29-7; XP-002745330; (Oct. 16, 2001) Supplier: Interbioscreen Ltd.; 1 page.

Database accession No. CID 366668, NSC635343—Compound summary; XP-002717180; (Mar. 26, 2005) Database PubChem Compound; pp. 1-3.

Database accession No. CID 366694, NSC635411—Compound summary; (Mar. 6, 2005) Database PubChem Compound; pp. 1-3.

Database accession No. CID 398900, NCI60_038544—Compound summary; (May 30, 2009) Database PubChem Compound; pp. 1-2.

Database accession No. CID 703160, ZINC00085926—Compound summary; (Jul. 8, 2005) Database PubChem Compound; pp. 1-2.

Database accession No. CID 772922, ZINC00257314—Compound summary; (Jul. 8, 2005) Database PubChem Compound; pp. 1-2.

Database accession No. CID 797457, ZINC00302255—Compound summary; (Jul. 9, 2005) Database PubChem Compound; pp. 1-2.

Database accession No. CID 797741, ZINC00302664—Compound summary; (Jul. 9, 2005) Database PubChem Compound; pp. 1-2.

Database accession No. CID 1149577, ZINC00894999—Compound summary; (Jul. 10, 2005) Database PubChem Compound; pp. 1-2.

Database accession No. RN 1144428-37-4; XP-002745331; (May 8, 2009) Supplier: Interbioscreen Ltd.; 1 page.

Database accession No. CID 1517002, ZINC01439946—Compound summary; (Jul. 11, 2005) Database PubChem Compound; pp. 1-2.

Database accession No. CID 51703682, ZINC35686355—Compound summary; (May 5, 2011) Database PubChem Compound; pp. 1-2.

Delattre et al., "The Ewing family of tumors—a subgroup of small-round-cell tumors defined by specific chimeric transcripts", N Engl J Med (1994) 331(5):294-299.

Demichelis et al., TMPRSS2: ERG gene fusion associated with lethal cancer in a watchful waiting cohort, Oncogene (2007) 26:4596-4599.

Derossi et al., "The third helix of the Antennapedia homeodomain translocates through biological membranes", J Biol Chem (1994) 269(14):10444-10450.

Erkizan et al., "A small molecule blocking oncogenic protein EWS-FLI1 interaction with RNA helicase A inhibits growth of Ewing's sarcoma", Nat Med. (2009) 15(7): 750-756.

Feldmann et al., "Blockage of hedgehog signaling inhibits pancreatic cancer invasion and metastases: A new paradigm for combination therapy in solid cancers", Cancer Res. (2007) 67:2187-2196.

Frangioni et al., "Use of a general purpose mammalian expression vector for studying intracellular protein targeting: identification of critical residues in the nuclear lamin A/C nuclear localization signal", J Cell Sci (1993) 105(Pt. 2):481-488.

French et al., "Midline carcinoma of children and young adults with NUT rearrangement", J Clin Oncol (2004) 22(20):4135-4139.

Fujii et al., "An antagonist of dishevelled protein-protein interaction suppresses beta-catenin-dependent tumor cell growth", Cancer Res (2007) 67(2):573-579.

Gadek et al., "Small molecule antagonists of proteins", Biochem Pharmacol (2003) 65(1):1-8.

Gangwal et al., "Microsatellites as EWS/FLI response elements in Ewing's sarcoma", Proc Natl Acad Sci U S A (2008) 105(29):10149-10154.

Garden et al., "A versatile synthetic methodology for the synthesis of tryptophols", Tetrahedron (2002) 58(42):8399-8412.

Grier et al., "Addition of ifosfamide and etoposide to standard chemotherapy for Ewing's sarcoma and primitive neuroectodermal tumor of bone", N Engl J Med (2003) 348(8):694-701.

Golub et al., "Molecular Classsification of Cancer: Class Discovery and Class Prediction by Gene Expression Monitoring", Science (1999) 286: 531-537.

Gyurkocza et al., "Antileukemic activity of shepherdin and molecular diversity of hsp90 inhibitors", J Natl Cancer Inst (2006) 98(15):1068-1077.

Hartman et al., "RNA helicase A is necessary for translation of selected messenger RNAs", Nat Struct Mol Biol. (2006) 13:509-516.

Helman et al., "Mechanisms of sarcoma development", Nat Rev Cancer (2003) 3(9):685-694.

Hu-Lieskovan et al., "Sequence-specific knockdown of EWS-FLI1 by targeted, nonviral delivery of small interfering RNA inhibits tumor growth in a murine model of metastatic Ewing's sarcoma", Cancer Res (2005) 65:8984-8992.

Iost et al., "mRNAs can be stabilized by DEAD-box proteins", Nature (1994) 372(6502):193-196.

Joshi et al., "Synthesis and central nervous system activities of certain fluorine-containing 3-substituted indol-2-ones." Pharmazie (1984) 39(3): 153-155.

IUPAC-IUB [Inter'l Union of Pure and Applied Chemistry—Inter'l Union of Biochemistry} Commission of Biochemical Nomenclature. Appreviated nomenclature of synthetic polypeptides (polymerized amino acids). Revised Recommentations (1971); Biochem. (1972) 11(5):942-944.

Kaiser, J., "First Pass at Cancer Genome Reveals Complex Landscape", Sciene (2006) 313:1370.

Khan et al., "Classification and diagnostic prediction of cancers using gene expression profiling and artificial neural networks", Nat Med (2001) 7(6):673-679.

Kidwai et al., "Microwave-induced "solvent-free" novel technique for the synthesis of spiro [indole-pyrazole/isoxazole/pyrimidine] derivatives", Oxidation Communications (2001) 24(2): 287-290.

Kinsey et al., "NR0B1 is required for the oncogenic phenotype mediated by EWS/FLI in Ewing's sarcoma", Mol Cancer Res (2006) 4(11):851-859.

Knoop et al., "The splicing factor U1C represses EWS/FLI-mediated transactivation", J Biol Chem (2000) 275(32):24865-24871.

Knoop et al., "EWS/FLI alters 5'-splice site selection", J Biol Chem (2001) 276(25):22317-22322.

Kobayashi et al., "Studies on Indole Derivatives—Synthesis of 3-Phenyl-9$H$-pyridazino[3,4-$b$]indole Derivatives", Chem Pharm Bull. (1964) 12(10):1129-1135.

Kovar et al., "EWS/FLI-1 antagonists induce growth inhibition of Ewing tumor cells in vitro", Cell Growth Differ (1996) 7(4):429-437.

Kovar et al., "Potentials for RNAi in sarcoma research and therapy: Ewing's sarcoma as a model", Semin Cancer Biol. (2003) 13:275-281.

Krontiris et al., "Internal Medicine", 4th Edition, Elsevier Science (1994) Chapters 71-72, pp. 699-729.

Lala et al., "Role of nitric oxide in tumor progression: Lessons from experimental tumors", Cancer Metastasis Rev. (1998) 17(1): 91-106.

Lambert et al., EWS FLI-1 antisense nanocapsules inhibits Ewing sarcoma-related tumor in mice, Biochem Biophys Res Commun. (2000) 279(2):401-406.

(56) References Cited

OTHER PUBLICATIONS

Lang et al., "Identification of peptide mimetics of xenoreactive alpha-Gal antigenic epitope4 by phage display", Biochem Biophys Res Commun (2006) 306:27-66.
Lee et al., "RNA helicase A is essential for normal gastrulation", Proc Natl Acad Sci U S A (1998) 95(23):13709-13713.
Leeson et al., "The influence of drug-like concepts on decision-making in medicinal chemistry", Nature reviews (2007) 6(11):881-890.
Lessnick et al., "The Ewing's sarcoma oncoprotein EWS/FLI induces a p53-dependent growth arrest in primary human fibroblasts", Cancer Cell (2002) 1(4):393-401.
Li et al., "Control of apoptosis and mitotic spindle checkpoint by survivin", Nature (1998) 396(6711):580-584.
Lindgren et al., "Translocation properties of novel cell penetrating transportan and penetratin analogues", Bioconjug Chem (2000) 11(5):619-626.
Maitra et al., "Detection of t(11;22)(q24;q12) Translation and EWS-FLI-1 Fusion Transcript in a Case of Solid Pseudopapillary Tumor of the Pancreas", Ped Develop Pathol. (2000) 3:603-605.
Maksimenko et al., "Oligonucleotides targeted against a junction oncogene are made efficient by nanotechnologies", Pharm Res (2003) 20(10):1565-1567.
Mateo-Lozano et al.; Rapamycin induces the fusion-type independent downregulation of the EWS/FLI-1 proteins and inhibits Ewing's sarcoma cell proliferation; Oncogene (2003) 22(58):9282-9287.
May et al., "Ewing sarcoma 11;22 translocation produces a chimeric transcription factor that requires the DNA-binding domain encoded by FLI1 for transformation", Proc Natl Acad Sci U S A (1993) 90(12):5752-5756.
May et al., "The Ewing's sarcoma EWS/FLI-1 fusion gene encodes a more potent transcriptional activator and is a more powerful transforming gene than FLI-1", Mol Cell Biol (1993) 13(12):7393-7398.
McIntyre et al., "Design and cloning strategies for constructing shRNA expression vectors", BMC Biotechnol. (2006) 6:1.
Medlineplus; Cancer [online]; [retrieved on Jul. 6, 2007] URL—http://www.nlm.nik.gov/medlineplus/cancer.html. 10 pages.
Merchant et al., "Potential use of imatinib in Ewing's sarcoma: evidence for in vitro and in vivo activity", J Natl Cancer Inst (2002) 94(22):1673-1679.
Merchant et al., Interferon gamma enhances the effectiveness of tumor necrosis factor-related apoptosis—Inducing ligand receptor agonists in a xenograft model of Ewing's sarcoma., Cancer Res (2004) 64(22):8349-8356.
Murray et al., "Targeting protein-protein interactions: Lessons from p53/MDM2", Biopolymers (2007) 88(5):657-686.
Myohanen et al., "Sequence-specific DNA binding activity of RNA helicase A to the p16INK4a promoter", J Biol Chem (2001) 276(2):1634-1642.
Nakajima et al., "RNA helicase A mediates assocation of CBP with RNA polymerase II", Cell (1997) 90(6):1107-1112.
Nakatani et al., "Identification of p21WAF1/CIP1 as a direct target of EWS-Fli1 oncogenic fusion protein", J Biol Chem (2003) 278(17):15105-15115.
Ng et al., "Multiple aromatic side chains within a disordered structure are critical for transcription and transforming activity of EWS family oncoproteins", Proc Natl Acad Sci U S A (2007) 104(2):479-484.
Ojida et al., "Highly enantioselective reformatsky reaction of ketones: Chelation-assisted enantioface discrimination", Org Lett (2002) 4(18):3051-3054.
Ouchida et al., "Loss of tumorigenicity of Ewing's sarcoma cells expressing antisense RNA to EWS-fusion transcripts", Oncogene (1995) 11(6):1049-1054.
Pagliaro et al., "Emerging classes of protein-protein interaction inhibitors and new tools for their development", Curr Opin Chem Biol. (2004) 8(4):442-449.

Pajouhesh et al., "Potential Anticonvulsants VI: Condensation of Isatins with Cyclohexonone and Other Cyclic Ketones", J Pharma Sciences (1983) 72(3):318-321.
Palermo et al., "The AF4-mimetic peptide, PFWT, induces necrotic cell death in MV4-11 leukemia cells", Leuk Res. (2008) 32(4):633-42.
Perez et al., "Antennapedia homeobox as a signal for the cellular internalization and nuclear addressing of a small exogenous peptide", J Cell Sci (1992) 102(Pt. 4):717-722.
Petermann et al., "Oncogenic EWS-Fli1 interacts with hsRPB7, a subunit of human RNA polymerase II", Oncogene (1998) 17:603-610.
Plescia et al., "Rational design of shepherdin, a novel anticancer agent", Cancer Cell (2005) 7(5):457-468.
Popp et al., "Synthesis of 3-Hydroxy-3-phenacyloxindole Analogs", J Pharma Science (1979) 68(4):519-520.
Poppe et al., "Expression analyses identify MLL as a prominent target of 11q23 amplification and support an etiologic role for MLL gain of function in myeloid malignancies", Blood (2004) 103(1):229-235.
Pui et al., "Clinical heterogeneity in childhood acute lymphoblastic leukemia with 11q23 rearrangements", Luekemia (2003) 17(4):700-706.
Pui et al., "Acute lymphoblastic leukemia", N Engl J Med (2004) 350(15):1535-1548.
Rahim et al., "YK-4-279 Inhibits ERG and ETV1 Mediated Prostate Cancer Cell Invasion", PLoS One (2011) 6(4):e19343; 8 pages.
"Remington's Pharmaceutical Sciences", Mack Publishing Company 19th edition (1995).
Riggi et al., "Ewing's sarcoma—Like tumors originate from EWS-FLI-1-expressing mesenchymal progenitor cells", Cancer Res (2006) 66(19):9786.
Righetti et al., "Heterodiene Syntheses. Part 21. etc.". J Chem Soc., Perkin Transactions I, (1979) 4: 863-868.
RN 667914-27-4 (Registry, 2H-Indol-2-one, 3-[2-(4-aminophenyl)-2-oxoethyl]-5, 7-dichloro-1, 3-dihydro-3-hydroxy, Mar. 26, 2004); 1 page.
RN 667914-33-2 (Registry, 2H-Indol-2-one, 4, 7-dichloro-3-[2-(4-aminophenyl)-2-oxoethyl]-1, 3-dihydro-3-hydroxy, Mar. 26, 2004); 1 page.
RN 672338-27-1 (Registry, 2H-Indol-2-one, 4, 6-dichloro-1, 3-dihydro-3-hydroxy-3-[2-(3-nitrophenyl)-2-oxoehyl], Apr. 7, 2004); 1 page.
RN 6938523-27-7 (Registry, 2H-Indol-2-one, 7-bromo-1,3-dihydro-3-hydroxy-3-[2-(4-methoxyphenl)-2-oxoethyl]-5-methyl, Jun. 16, 2004); 1 page.
RN 848688-25-5 (Registry, 2H-Indol-2-one, 4,6-dichloro-3-[2-(2, 4-dimethoxyphenyl)-2-oxoethyl]-1, 3-dihydro-3-hydroxy, Apr. 18, 2005); 1 page.
RN 900016-35-5 (Registry, 2H-Indol-2-one, 7-chloro-1, 3-dihydro-3-hydroxy-3-[2-oxo-2-(3,4,5-trimethoxphenyl) ethyl, Aug. 9, 2006); 1 page.
RN 909225-77-0 (Registry, 2H-Indol-2-one, 7-chloro-3-[2-(4-ethylphenyl)-2-oxoethyl]-1,3-hydroxy, Oct. 2, 2006); 1 page.
RN 692281-43-9 (Registry, 2H-Indol-2-one, 4-chloro-3-[2-(4-fluorophenyl)-2-oxoethyl]-1,3-dihydro-3-hydroxy-7-methyl, Jun. 13, 2004); 1 page.
RN 848755-10-2 (Registry, 2H-Indol-2-one4,6-dichloro-3-[2-(3,4-dimethoxyphenyl)-2-oxoethyl)-1,3-dihydro-3-hydroxy, Apr. 19, 2005); 1 page.
Sanchez et al., "Alteration of cyclin D1 transcript elongation by a mutated transcription factor up-regulates the oncogenic D1b splice isoform in cancer", Proc Natl Acad Sci U S A. (2008) 105(16):6004-6009.
Sillerud et al., "Design and structure of peptide and peptidomimetic antagonists of protein-protein interaction", Curr Protein Pept Sci (2005) 6(2):151-169.
Smith et al., "Expression profiling of EWS/FLI identifies NKX2.2 as a critical target gene in Ewing's sarcoma", Cancer Cell (2006) 9(5):405-416.
Snyder et al., "Treatment of terminal peritoneal carcinomatosis by a transducible p53-activating peptide", PLos Biol (2004) 2(2):0186-0193.

(56) References Cited

OTHER PUBLICATIONS

Srinivasan et al., "The synthetic peptide PFWT disrupts AF4-AF9 protein complexes and induces apoptosis in t(4;11) leukemia cells", Leukemia (2004) 18(8):1364-1372.
Stegmaier et al., "Signature-based small molecule screening identifies cytosine arabinoside as an EWS/FLI modulator in Ewing sarcoma", PLoS medicine (2007) 4(4):e122.
Strigacova et al., "Novel oxindole derivatives and their biological activity", Folia Microbiol (Praha). (2001) 46(3):187-192.
Subramanian et al., "Gene set enrichment analysis: a knowledge-based approach for interpreting genome-wide expression profiles", Proc Natl Acad Sci U S A. (2005) 102(43):15545-15550.
Tanaka et al., "EWS-FLI1 antisense oligodeoxynucleotide inhibits proliferation of human Ewing's sarcoma and primitive neuroectodermal tumor cells", J Clin Invest (1997) 99(2):239-247.
Terrone et al., "Penetratin and related cell-penetrating cationic peptides can translocate across lipid bilayers in the presence of a transbilayer potential", Biochem. (2003) 42(47):13787-13799.
Tetsuka et al., "RNA helicase A interacts with nuclear factor kappaB p65 and functions as a transcriptional coactivator", Eur J Biochem (2004) 271(18):3741-3751.
Thoren et al., "The antennapedia peptide penetratin translocates across lipid bilayers—the first direct observation", FEBS Lett (2000) 482(3):265-268.
Tiemann et al., "Solid pseudopapillary neoplasms of the pancreas are associated with FLI-1 expression, but not with EWS/FLI-1 translocation." Mod Pathol. (2006) 19(11):1409-1413.
Torchia et al., "EWS/FLI-1 induces rapid onset of myeloid/erythroid leukemia in mice", Mol Cell Biol (2007) 27(22):7918-7934.
Toretsky et al., "Inhibition of EWS-FLI-1 fusion protein with antisense oligodeoxynucleotides", J Neurooncol. (1997) 31(1-2):9-16.
Toretsky et al., "Phosphoinositide 3-hydroxide kinase blockade enhances apoptosis in the Ewing's sarcoma family of tumors", Cancer Res (1999) 59(22):5745-5750.
Toretsky et al., "Glypican-3 expression in Wilms tumor and hepatoblastoma", J Pediatr Hematol Oncol. (2001) 23(8):496-499.
Toretsky et al., "Oncoprotein EWS-FLI1 activity is enhanced by RNA helicase A", Cancer Res (2006) 66(11):5574-5581.
Üren et al., "Recombinant EWS-FLI1 oncoprotein activates transcription", Biochem. (2004) 43(42):13579-13589.
Üren et al., "Activation of the canonical Wnt pathway during genital keratinocyte transformation: a model for cervical cancer progression", Cancer Res (2005) 65(14):6199-6206.
Üren et al., "Ewing's Sarcoma Oncoprotein EWS-FLI1: The Perfect Target without a Therapeutic Agent", Future Onc. (2005) 1(4):521-528.
Üren et al., "Pediatric malignancies provide unique cancer therapy targets", Curr Opin Pediatr. (2005) 17:14-19.
Välineva et al., "Characterization of RNA helicase A as component of STAT6-dependent enhanceosome", Nucleic Acids Res (2006) 34(14):3938-3946.
Velikorodov et al., "Some Condensations of Methyl 4-Acetylphenylcarbamate", Russian J Org Chem (2010) 46(7):971-975.
Velikorodov et al., "Synthesis of New Spiro Compounds Containing a Carbamate Group", Russian J Org Chem. (2010) 46(12):1826-1829.
Velikorodov et al., "Synthesis of 3-Pyrrol-3'-yloxindoles with a Carbamate Function", Russian J Org Chem. (2011) 47(11):1715-1717.
Velikorodov et al., "L-Proline-Catalyzed 1,3-Dipolar Cycloaddition of Some Schiff Bases to Methyl 4-[1-Oxo-2(2-oxo-2,3-dihydro1$H$-indol-3-ylidene)ethyl]phenylcarbamate", Russian J Org Chem. (2011) 47(10):1596-1597.
Velikorodov et al., "Three-Component Synthesis of Spiro Compounds with a Carbamate Functionality", Russian J Org Chem. (2011) 47(3):402-404.
Von Hippel et al., "A general model for nucleic acid helicases and their "coupling" within macromolecular machines", Cell (2001) 104(2):177-190.
Walensky et al., "Activation of apoptosis in vivo by a hydrocarbon-stapled BH3 helix", Science (2004) 305(5689):1466-1470.
Wikipedia—Cancer [online]; [retrieved on Jul. 6, 2007]. URL; http://en.wikipedia.org/wiki/Cancer; 2 pages.
Xie et al., "Functional anthology of intrinsic disorder. 1. Biological processes and functions of proteins with long disordered regions", J Proteome Res. (2007) 6(5):1882-1898.
Yin et al., "Low molecular weight inhibitors of Myc-Max interaction and function", Oncogene (2003) 22(40):6151-6159.
Zhang et al., "Multiple functions of nuclear DNA helicase II (RNA helicase A) in nucleic acid metabolism", Acta Biochim Biophys Sin (Shanghai) (2004) 36(3):177-183.
Zhong et al., "RNA helicase A in the MEF1 transcription factor complex upregulates the MDR1 gene in multidrug-resistant cancer cells", J Biol Chem (2004) 279(17):17134-17141.
International Preliminary Report on Patentability dated Apr. 26, 2016 for International Patent Application No. PCT/US2014/061418, filed Oct. 20, 2014.

METHODS AND COMPOSITIONS FOR TREATING CANCER

RELATED APPLICATIONS

This application is the U.S. National Phase of PCT Application No. PCT/US2014/061418 filed Oct. 20, 2014 and published in English as WO 2015/061229 on Apr. 30, 2015 which claims the benefit of U.S. Provisional Application No. 61/895,308 filed Oct. 24, 2013 entitled "METHODS AND COMPOSITIONS FOR TREATING CANCER", the contents of which is incorporated herein by reference in its entirety.

STATEMENT REGARDING FEDERALLY SPONSORED R&D

This invention was made with government support under NIH Grant/Contract Numbers R01CA138212, R01CA133662, RC4CA156509 awarded by the National Institutes of Health of the United States of America. The government has certain rights in the invention.

FIELD OF THE INVENTION

Methods and compositions provided herein relate to the treatment of cancer. In some embodiments, the compositions have utility in the treatment of cancers including glioblastoma multiforme and lung cancer.

BACKGROUND OF THE INVENTION

The Central Brain Tumor Registry of the United States (CBTRUS) lists the total number of primary malignant brain tumor deaths for all 50 states and the District of Columbia in 2012 is estimated to be 13,700. Glioblastomas (GBMs) are the most common brain malignancy with a median survival of only 14.6 months in humans despite standard tri-modality treatment consisting of surgical resection, post-operative radiation therapy and temozolomide chemotherapy. Therapy is almost never curative because the infiltrative nature of these tumors and their intrinsic resistance to radiation and chemotherapy. Even with optimal treatment, the median survival is less than 15 months, with only 10% of patients surviving 2 years without disease recurrence. New therapeutic targets are clearly needed to improve patient survival and quality of life for Glioblastomas and other cancers.

In addition, the Ewing's Sarcoma Family of Tumors (ESFT) are highly aggressive tumors that occur in children, adolescents and young adults in the bone and the soft tissues. They respond to chemotherapy, yet 75% to 80% of the patients who have developed metastatic ESFTs will die in five years despite high doses of chemotherapy (Grier, H. E et al., N. Engl. J. Med. 348, 694-701 (2003)). ESFTs contain a well characterized chromosomal translocation. This joins the Ewing's sarcoma gene (EWS), located on chromosome 22, to an ets family gene, often friend leukemia insertion (FLI)1 located on the chromosome 11, t(11:22) which lead to the expression of various fusion proteins (Aykut Uren, Jeffrey A Torestsky Ewing's sarcoma oncoproteins EWS-FLI1: the perfect target without a therapeutic agent, Future Oncol. 1(4), 521-528 (2005)).

In vitro and in vivo studies have demonstrated that the elimination of the oncoprotein, EWS-FLI1, leads to a decrease proliferation of ESTF cell lines and a decrease of tumor volume. EWS-FLI1 lacks enzymatic activity, however, the RHA helicase A (RHA) increases EWS-FLI1-modulated oncogenesis, therefore the protein-protein interactions between the two proteins is required for the maintenance of the tumor growth (Hyariye N Erkizan et al. A small molecule blocking oncogenic protein EWS-Fll1 interacting with RHA helicase A inhibits growth of Ewing's sarcoma. Nature Medicine 15(7) 750-756 (2009)). The paradigm of disrupting key protein interactions may have utility in treatment of diseases including sarcomas with similar translocations, and leukemias with MLL translocations ((Helman L J, Meltzer P. Mechanisms of sarcoma development. Nat Rev Cancer 2003; 3(9):685-94); and Pui C H, Relling M V, Downing J R. Acute lymphoblastic leukemia. N Engl J Med 2004; 350(15):1535-48). Moreover, disordered proteins may be excellent therapeutic targets based on their intrinsic biochemical properties (Cheng Y, LeGall T, Oldfield C J, et al. Rational drug design via intrinsically disordered protein. Trends Biotechnol 2006; 24(10):435-42).

Despite years of in vitro and xenograft studies with antisense and siRNA directed towards EWS-FLI1, none of these is heretofore practical as a human therapy based on inadequate delivery and stability. Accordingly, there is a need for improved therapies to treat disorders such as ESFTs.

SUMMARY OF THE INVENTION

In a generally applicable first aspect (i.e., independently combinable with any of the aspects or embodiments identified herein), a compound is provided of Formula I:

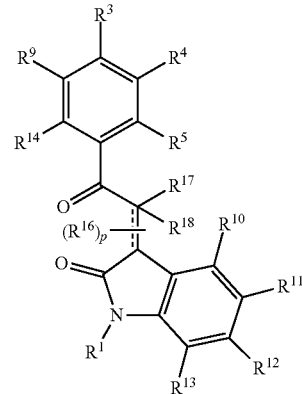

Formula (I)

or a pharmaceutically acceptable salt thereof,
wherein $R^1$ is selected from the group consisting of hydrogen, $C_{1-6}$ alkyl, one amino acid, two amino acids linked together, three amino acids linked together,

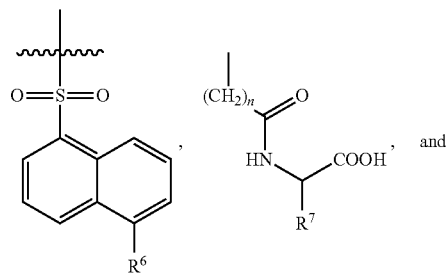

, and

-continued

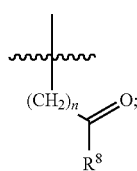

$R^3$, $R^4$, $R^5$, $R^{14}$, $R^{17}$ and $R^{18}$ are independently selected from the group consisting of hydrogen, halogen, $C_{1-6}$ alkyl, $C_{1-6}$ alkoxy, —C(=O)NH$_2$, —NO$_2$, —NH$_2$, —OH, —NH($R^{15}$), —N($R^{15}$)$_2$, and —S$R^{15}$;

$R^{10}$, $R^{11}$, $R^{12}$, and $R^{13}$ are each independently selected from the group consisting of hydrogen, halogen, $C_{1-6}$ alkyl, $C_{1-6}$ alkoxy, —C(=O)NH$_2$, —NO$_2$, —NH$_2$, —OH, —NH($R^{15}$), —N($R^{15}$)$_2$, and —S$R^{15}$;

$R^6$ is $C_{1-6}$ dialkyl amine;

$R^7$ is selected from the group consisting of hydrogen and $C_{1-6}$ alkyl;

$R^8$ and $R^{15}$ are each independently $C_{1-6}$ alkyl;

each $R^{16}$ is independently hydrogen, —OH, or $C_{1-6}$ alkoxy;

n is an integer from 0 to 4;

p is 1 or 3; and the dashed line represents an optional double bond where said double bond has a configuration selected from the group consisting of cis and trans, with the proviso that at least one of $R^3$, $R^4$, $R^5$, $R^9$, and $R^{14}$ is selected from the group consisting of —NH($R^{15}$), —N($R^{15}$)$_2$, and —S$R^{15}$.

In an embodiment of the first aspect, which is generally applicable (i.e., independently combinable with any of the aspects or embodiments identified herein), the compound of Formula I is:

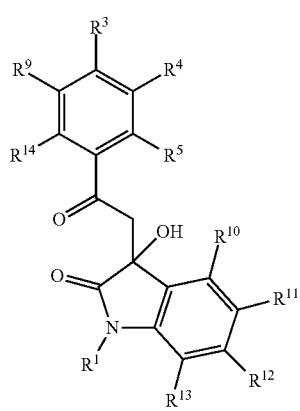

(Ia)

or a pharmaceutically acceptable salt thereof.

In an embodiment of the first aspect, which is generally applicable (i.e., independently combinable with any of the aspects or embodiments identified herein), the compound of Formula I is:

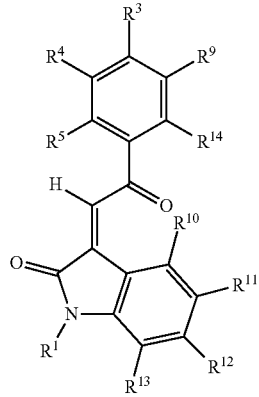

(Ib)

or a pharmaceutically acceptable salt thereof.

In an embodiment of the first aspect, which is generally applicable (i.e., independently combinable with any of the aspects or embodiments identified herein), $R^1$ is selected from the group consisting of Leu, Leu-Asp, Leu-Asp-Ala, —CH$_2$—C(=O)—NHCH$_2$COOH, —CH$_2$—C(=O)—(CH$_2$)C(CH$_3$)$_2$,

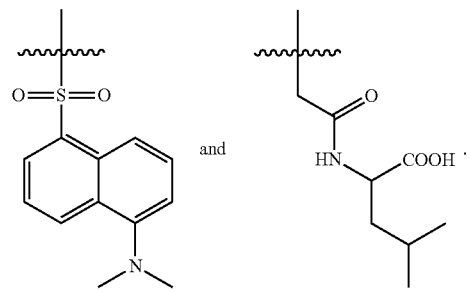

and

In an embodiment of the first aspect, which is generally applicable (i.e., independently combinable with any of the aspects or embodiments identified herein), $R^3$ is selected from —NH($R^{15}$), —N($R^{15}$)$_2$, and —S$R^{15}$.

In an embodiment of the first aspect, which is generally applicable (i.e., independently combinable with any of the aspects or embodiments identified herein), $R^3$ is —N(CH$_3$)$_2$.

In an embodiment of the first aspect, which is generally applicable (i.e., independently combinable with any of the aspects or embodiments identified herein), $R^3$ is —SCH$_3$.

In an embodiment of the first aspect, which is generally applicable (i.e., independently combinable with any of the aspects or embodiments identified herein), the compound of Formula I is:

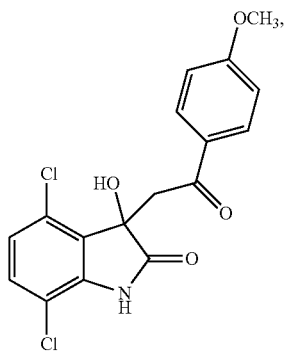

or a pharmaceutically acceptable salt thereof.

In a generally applicable second aspect (i.e. independently combinable with any of the aspects or embodiments identified herein), a method is provided of treating a cancer comprising administering to a subject in need thereof an effective amount of the compound of Formula I.

In an embodiment of the second aspect, which is generally applicable (i.e., independently combinable with any of the aspects or embodiments identified herein), the subject is mammalian.

In an embodiment of the second aspect, which is generally applicable (i.e., independently combinable with any of the aspects or embodiments identified herein), the subject is human.

In an embodiment of the second aspect, which is generally applicable (i.e., independently combinable with any of the aspects or embodiments identified herein), the cancer is selected from the group consisting of lung adenocarcinoma, and glioblastoma multiforme.

In an embodiment of the second aspect, which is generally applicable (i.e., independently combinable with any of the aspects or embodiments identified herein), the cancer comprises a translocation comprising an ETS gene selected from the group consisting of FLI1, ETV1, ETV4, ERG, ETS1, and ETS2.

In an embodiment of the second aspect, which is generally applicable (i.e., independently combinable with any of the aspects or embodiments identified herein), the compound is administered parentally.

In a generally applicable third aspect (i.e. independently combinable with any of the aspects or embodiments identified herein), a method is provided of killing or inhibiting the growth of a neoplastic cell comprising contacting the cell with an effective amount of a compound of Formula I:

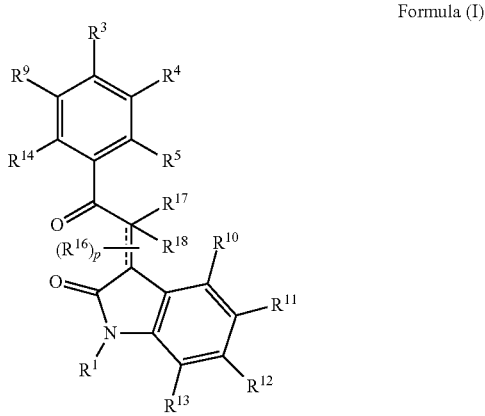

Formula (I)

or a pharmaceutically acceptable salt thereof, wherein $R^1$ is selected from the group consisting of hydrogen, $C_{1-6}$ alkyl, one amino acid, two amino acids linked together, three amino acids linked together,

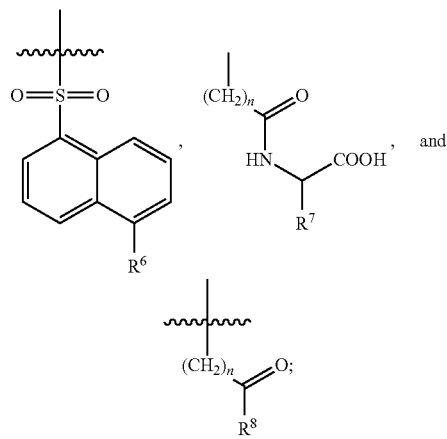

$R^3$, $R^4$, $R^5$, $R^9$, and $R^{14}$ are each independently selected from the group consisting of hydrogen, halogen, $C_{1-6}$ alkyl, $C_{1-6}$ alkoxy, —C(=O)NH$_2$, —NO$_2$, —NH$_2$, —OH, —NH($R^{15}$), —N($R^{15}$)$_2$, and —SR$^{15}$;

$R^{10}$, $R^{11}$, $R^{12}$, and $R^{13}$ are each independently selected from the group consisting of hydrogen, halogen, $C_{1-6}$ alkyl, $C_{1-6}$ alkoxy, —C(=O)NH$_2$, —NO$_2$, —NH$_2$, —OH, —NH($R^{15}$), —N($R^{15}$)$_2$, and —SR$^{15}$;

$R^6$ is $C_{1-6}$ dialkyl amine;

$R^7$ is selected from the group consisting of hydrogen and $C_{1-6}$ alkyl;

$R^8$ and $R^{15}$ are each independently $C_{1-6}$ alkyl;

each $R^{16}$ is independently hydrogen, —OH, or $C_{1-6}$ alkoxy;

$R^{17}$ and $R^{18}$ are independently H or F;

n is an integer from 0 to 4;

p is 1 or 3; and the dashed line represents an optional double bond where said double bond has a configuration selected from the group consisting of cis and trans, with the proviso that at least one of $R^3$, $R^4$, $R^5$, $R^9$, and $R^{14}$ is selected from the group consisting of —NH($R^{15}$), —N($R^{15}$)$_2$, and —SR$^{15}$.

In an embodiment of the third aspect, which is generally applicable (i.e., independently combinable with any of the aspects or embodiments identified herein), the compound of Formula I is:

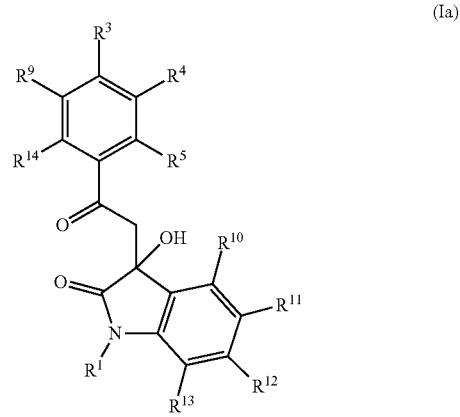

(Ia)

or a pharmaceutically acceptable salt thereof.

In an embodiment of the third aspect, which is generally applicable (i.e., independently combinable with any of the aspects or embodiments identified herein). The compound of Formula I is:

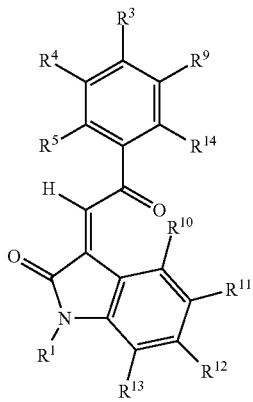

(Ib)

or a pharmaceutically acceptable salt thereof.

In an embodiment of the third aspect, which is generally applicable (i.e., independently combinable with any of the aspects or embodiments identified herein), $R^1$ is selected from the group consisting of Leu, Leu-Asp, Leu-Asp-Ala, —CH$_2$—C(=O)—NHCH$_2$COOH, —CH$_2$—C(=O)—(CH$_2$)C(CH$_3$)$_2$,

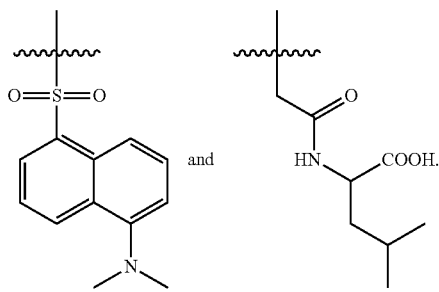 [SMILES: *S(=O)(=O)c1cccc2c(N(C)C)cccc12 ; *CC(=O)NC(CC(C)C)C(=O)O]

and

In an embodiment of the third aspect, which is generally applicable (i.e., independently combinable with any of the aspects or embodiments identified herein), $R^3$ is selected from —NH(R$^{15}$), —N(R$^{15}$)$_2$, and —SR$^{15}$.

In an embodiment of the third aspect, which is generally applicable (i.e., independently combinable with any of the aspects or embodiments identified herein), $R^3$ is —N(CH$_3$)$_2$.

In an embodiment of the third aspect, which is generally applicable (i.e., independently combinable with any of the aspects or embodiments identified herein), $R^3$ is —SCH$_3$.

In an embodiment of the third aspect, which is generally applicable (i.e., independently combinable with any of the aspects or embodiments identified herein). The compound of Formula I is:

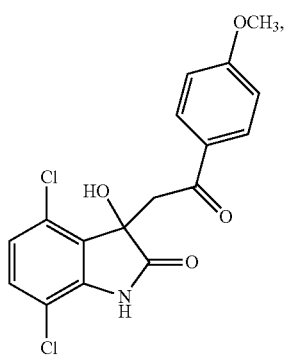 [SMILES: COc1ccc(C(=O)CC2(O)C(=O)Nc3c(Cl)ccc(Cl)c32)cc1]

or a pharmaceutically acceptable salt thereof.

In an embodiment of the third aspect, which is generally applicable (i.e., independently combinable with any of the aspects or embodiments identified herein), the cell is mammalian.

In an embodiment of the third aspect, which is generally applicable (i.e., independently combinable with any of the aspects or embodiments identified herein), the cell is human.

In an embodiment of the third aspect, which is generally applicable (i.e., independently combinable with any of the aspects or embodiments identified herein), the cell is selected from the group consisting of lung adenocarcinoma, and glioblastoma multiforme.

In an embodiment of the third aspect, which is generally applicable (i.e., independently combinable with any of the aspects or embodiments identified herein), the cell comprises a translocation comprising an ETS gene selected from the group consisting of FLI1, ETV1, ETV4, ERG, ETS1, and ETS2.

In an embodiment of the third aspect, which is generally applicable (i.e., independently combinable with any of the aspects or embodiments identified herein), the cell is in vivo.

In an embodiment of the third aspect, which is generally applicable (i.e., independently combinable with any of the aspects or embodiments identified herein), the cell is ex vivo.

In a generally applicable fourth aspect (i.e., independently combinable with any of the aspects or embodiments identified herein), a compound is provided of Formula I:

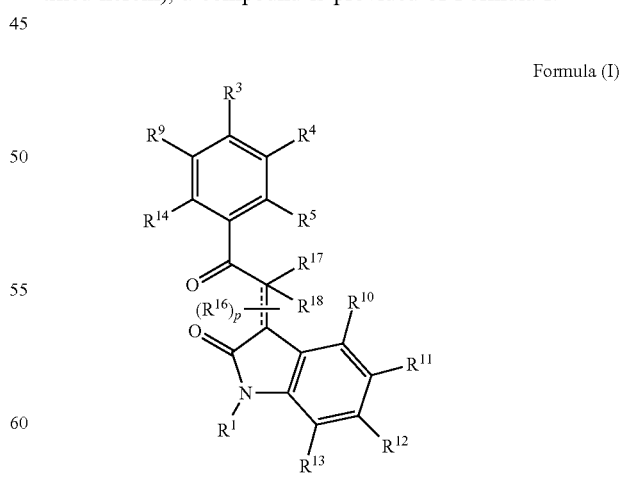

Formula (I)

or a pharmaceutically acceptable salt thereof,
wherein $R^1$ is selected from the group consisting of hydrogen, $C_{1-6}$ alkyl, one amino acid, two amino acids linked together, three amino acids linked together,

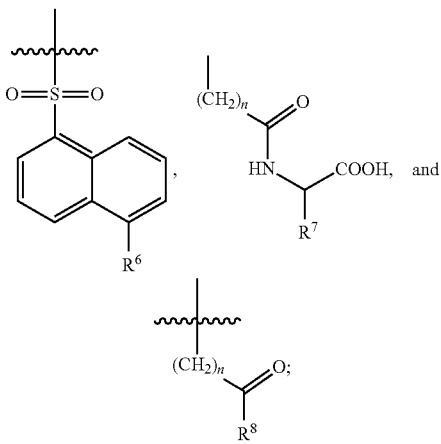

R$^3$, R$^4$, R$^5$, R$^9$, and R$^{14}$ are each independently selected from the group consisting of hydrogen, halogen, C$_{1-6}$ alkyl, C$_{1-6}$ alkoxy, —C(=O)NH$_2$, —NO$_2$, —NH$_2$, —OH, —NH(R$^{15}$), —N(R$^{15}$)$_2$, and —SR$^{15}$;

R$^{10}$, R$^{11}$, R$^{12}$, and R$^{13}$ are each independently selected from the group consisting of hydrogen, halogen, C$_{1-6}$ alkyl, C$_{1-6}$ alkoxy, —C(=O)NH$_2$, —NO$_2$, —NH$_2$, —OH, —NH(R$^{15}$), —N(R$^{15}$)$_2$, and —SR$^{15}$;

R$^6$ is C$_{1-6}$ dialkyl amine;

R$^7$ is selected from the group consisting of hydrogen and C$_{1-6}$ alkyl;

R$^8$ and R$^{15}$ are each independently C$_{1-6}$ alkyl;

each R$^{16}$ is independently hydrogen, —OH, or C$_{1-6}$ alkoxy;

R$^{17}$ and R$^{18}$ are independently H or F;

n is an integer from 0 to 4;

p is 1 or 3; and the dashed line represents an optional double bond where said double bond has a configuration selected from the group consisting of cis and trans, with the proviso that at least one of R$^3$, R$^4$, R$^5$, R$^9$, and R$^{14}$ is selected from the group consisting of —NH(R$^{15}$), —N(R$^{15}$)$_2$, and —SR$^{15}$.

In an embodiment of the fourth aspect, which is generally applicable (i.e., independently combinable with any of the aspects or embodiments identified herein), R$^1$ is selected from the group consisting of Leu, Leu-Asp, Leu-Asp-Ala, —CH$_2$—C(=O)—NHCH$_2$COOH, —CH$_2$—C(=O)—(CH$_2$)C(CH$_3$)$_2$,

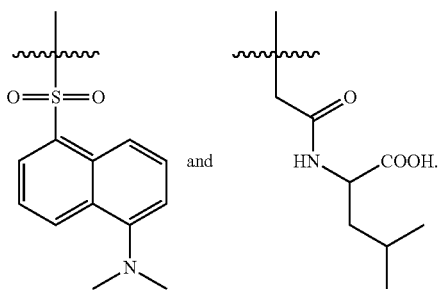 [SMILES: *S(=O)(=O)c1cccc2c(N(C)C)cccc12 ; *CC(=O)NC(CC(C)C)C(=O)O]

In an embodiment of the fourth aspect, which is generally applicable (i.e., independently combinable with any of the aspects or embodiments identified herein), R$^3$ is selected from —NH(R$^{15}$), —N(R$^{15}$)$_2$, and —SR$^{15}$.

In an embodiment of the fourth aspect, which is generally applicable (i.e., independently combinable with any of the aspects or embodiments identified herein), R$^3$ is —N(CH$_3$)$_2$.

In an embodiment of the fourth aspect, which is generally applicable (i.e., independently combinable with any of the aspects or embodiments identified herein), R$^3$ is —SCH$_3$.

In a generally applicable fifth aspect (i.e., independently combinable with any of the aspects or embodiments identified herein), pharmaceutical compositions are provided comprising compounds of Formula I.

Any of the features of an embodiment of the first through fifth aspects is applicable to all aspects and embodiments identified herein. Moreover, any of the features of an embodiment of the first through fifth aspects is independently combinable, partly or wholly with other embodiments described herein in any way, e.g., one, two, or three or more embodiments may be combinable in whole or in part. Further, any of the features of an embodiment of the first through fifth aspects may be made optional to other aspects or embodiments. Any aspect or embodiment of a method can be performed using a compound of another aspect or embodiment, and any aspect or embodiment of a compound can be configured to be employed in a method of another aspect or embodiment.

BRIEF DESCRIPTION OF THE DRAWINGS

FIG. 13A: Mice with ES xenografts were treated with 400 mg/kg compound or controls as indicated. Starting well-established tumors (300 mm³), mice were treated with intraperitoneal compound for three days, 6 total doses. FIG. 13B: H and E stained tumors from same experiment.

FIG. 16A. Luciferase assays of Cos-7 cells cotransfected with ERG and an Id-2 reporter luciferase construct. YK-4-279 treatment decreased Id-2 promoter activity without affecting ERG levels (*;p<0.001). FIG. 16B. VCaP cells were treated with siERG or YK-4-279 for 48 hours and ERG target mRNA and protein levels were determined. YK-4-279 treatment resulted in decreased PLAU, ADAM19 and PLAT mRNA expression. PLAU levels were also reduced.

DETAILED DESCRIPTION

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Figure 1:
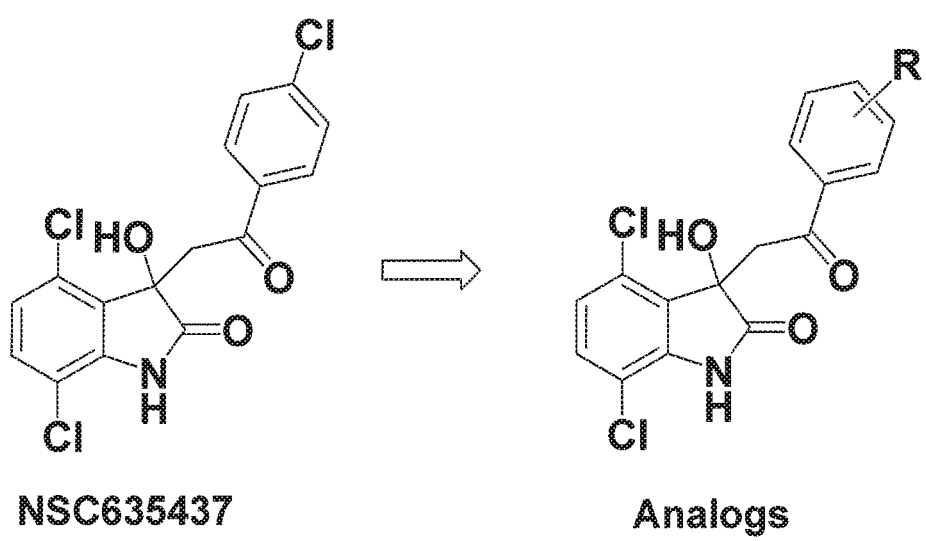
FIG. 1 shows the structure of NSC635437 and a generic structure for certain analogs.
Figure 2:
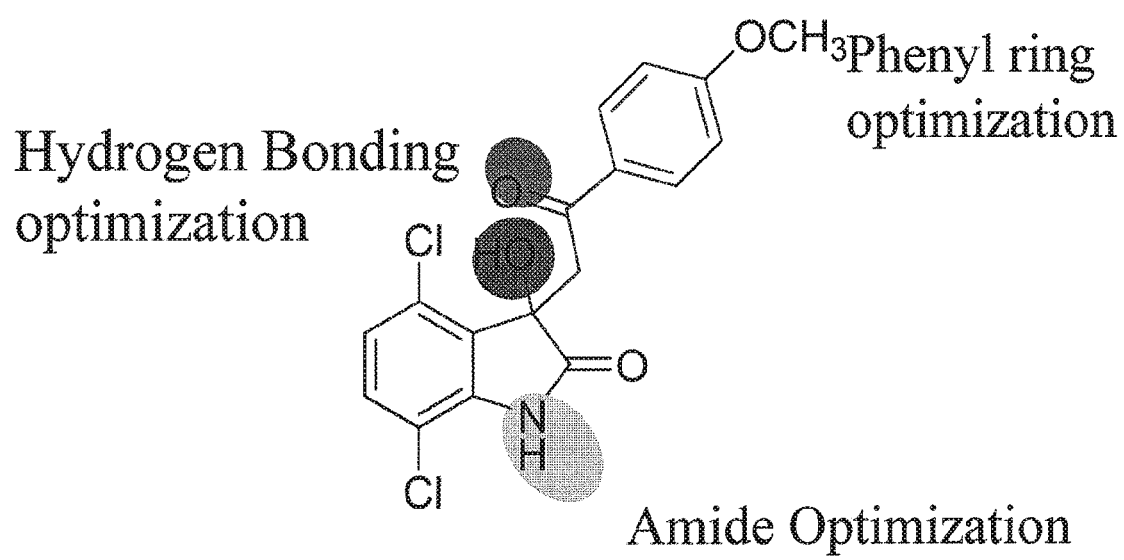
FIG. 2 shows an example strategy to increase the potency of YK-4-279.

A NCI/DTP library of three thousands small molecules was screened for EWS-FLI1 binding using Surface Plasmon Resonance. The compound, NSC635437, was selected as a suitable candidate for further optimization and further study (FIG. 1). Of the first series of analogs designed, YK-4-279, was the most active (FIG. 2). YK-4-279 has been shown to functionally inhibit EWS-FLI1 and ESFT cells and leads to caspase-3 activity increase (Hyariye N Erkizan et al. A small molecule blocking oncogenic protein EWS-FlI1 interacting with RHA helicase A inhibits growth of Ewing's sarcoma. Nature Medicine 15(7) 750-756 (2009)). The present application relates to improved compounds and methods of using such compounds to treat disorders such as lung adenocarcinoma, glioblastoma multiforme, and cancers comprising a translocation comprising an ETS gene selected from the group consisting of FLI1, ETV1, ETV4, ERG, ETS1, and ETS2.

Other methods and compositions useful with those provided herein are disclosed in Int. Pub. No. WO 2008/083326; U.S. Pub. No. 2010/0167994; U.S. Prov App. No. 61/623349; and Int. Pub. No. WO 2013/155341, the disclosures of which are expressly incorporated herein by reference in their entireties.

Definitions

As used herein, any "R" group(s) such as, without limitation, R, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^a$, $R^b$, represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^{1a}$ and $R^{1b}$ of an $NR^{1a}R^{1b}$ group are indicated to be "taken together," it means that they are covalently bonded to one another to form a ring:

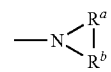

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino and a di-substituted amino group, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that includes a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl)

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heteroalicyclyl)alkyl" and "(heterocyclyl)alkyl" refer to a heterocyclic or a heteroalicyclylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

"Lower alkylene groups" are straight-chained —$CH_2$- tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl or a cycloalkynyl is defined as above. A non-limiting list of alkoxys is methoxy, ethoxy, n-propoxy, 1-methylethoxy(isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy, and 2-fluoroisobutoxy. A haloalkoxy may be substituted or unsubstituted.

As used herein, "aryloxy" and "arylthio" refers to RO— and RS—, in which R is an aryl, such as but not limited to phenyl. Both an aryloxy and arylthio may be substituted or unsubstituted.

A "sulfenyl" or "thio" group refers to an "—SR" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A sulfenyl may be substituted or unsubstituted. The term "sulfenyl" or "thio" includes, but is not limited to an —SH group (also referred to as a "thiol" group) as well as an —$SR_A$ group (also referred to as a "thioether" when $R_A$ is not hydrogen).

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein X is a halogen.

A "trihalomethanesulfonamido" group refers to an "$X_3CS(O)_2N(R_A)$—" group wherein X is a halogen and $R_A$ is hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

The term "amino" as used herein refers to a —$N(R)_2$ group, wherein R is independently selected from the group consisting of hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An amino may be substituted or unsubstituted. The term "amino" includes, but is not limited to a —$NH_2$ group (also referred to as an "ammonium" group), a —NHR group (also referred to as a "secondary amine" when R is not hydrogen), or a —$NR_2$ group (also referred to as a "tertiary amine" when R is not hydrogen).

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-sulfonamido may be substituted or unsubstituted.

An "O-carbamyl" group refers to a "—OC(=O)N($R_AR_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-carbamyl may be substituted or unsubstituted.

An "N-carbamyl" group refers to an "ROC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-carbamyl may be substituted or unsubstituted.

An "O-thiocarbamyl" group refers to a "—OC(=S)—N($R_A R_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-thiocarbamyl may be substituted or unsubstituted.

An "N-thiocarbamyl" group refers to an "ROC(=S)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-thiocarbamyl may be substituted or unsubstituted.

A "C-amido" group refers to a "—C(=O)N($R_A R_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Certain Synthetic Methods

In some embodiments, appropriate acetophenone (4.0 equiv.) and catalytic amount of diethylamine (10 drops) were added to a solution of 4,7-dichloroisatin (1.0 equiv.) in methanol (5 mL). The mixture was stirred at room temperature until starting material (4,7-dichloroisatin) disappeared completely. The resulted solution was concentrated and applied to flash chromatography eluting with Hexane/Ethyl acetate to afford pure product in quantitative yield. Further purification was done by recrystallization with Hexane/Ethyl acetate. NMR spectra were recorded using a Varian-400 spectrometer for $^1$H (400 MHz), chemical shifts (δ) are given in ppm downfield from tetramethylsilane as internal standard, and coupling constants (J-values) are in hertz (Hz). Elemental analyses were performed by Atlantic Microlabs.

Certain compounds provided herein can be prepared according to the following synthesis schemes.

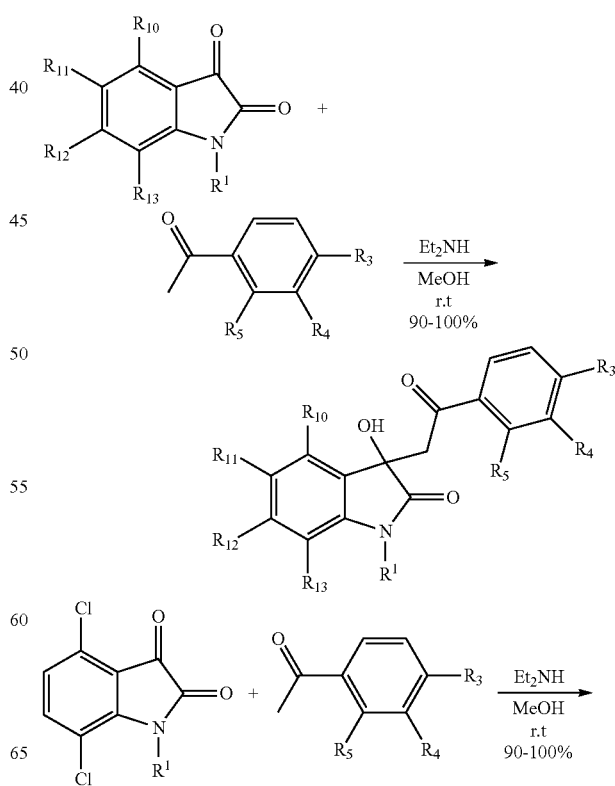

-continued

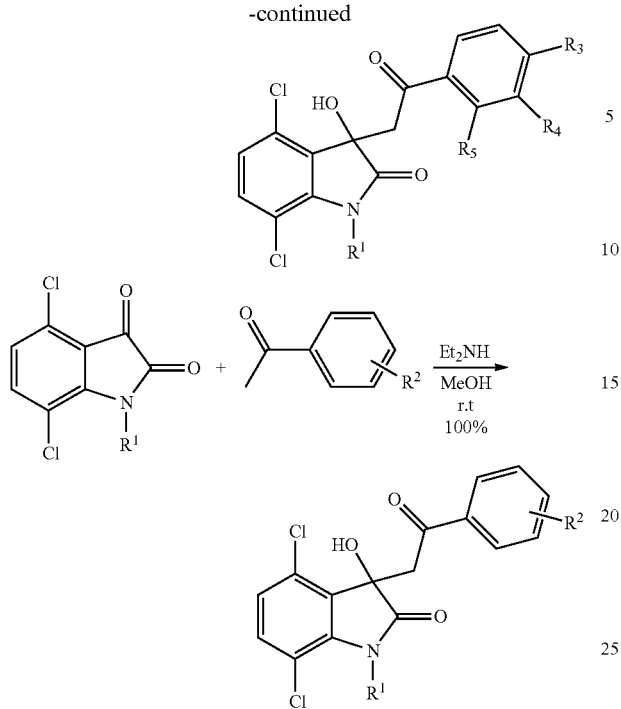

In these schemes, ketone (4.0 equiv.) and a catalytic amount of diethylamine (10 drops) are added to a solution of substituted isatin (1.0 equiv.) in methanol (5 mL). The mixture is stirred at room temperature until starting material (substituted isatin) disappears completely. The resulting solution is concentrated and applied to flash chromatography eluting with hexane/ethyl acetate to afford pure product in quantitative yield. Further purification is done by recrystallization with hexane/ethyl acetate.

The inhibitors incorporating a carbon-carbon double bond in the group linking the two ring systems can be prepared from the corresponding saturated inhibitor by reducing the compound using synthetic techniques known in the art.

Certain Compounds

Certain compounds provided herein include compounds having a Formula I:

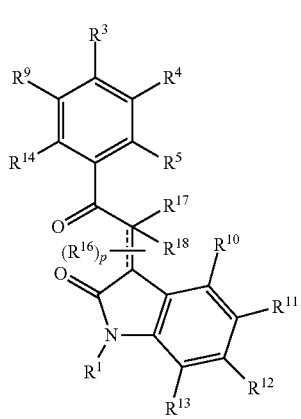

Formula (I)

or a pharmaceutically acceptable salt thereof, wherein $R^1$ is selected from the group consisting of hydrogen, $C_{1-6}$ alkyl, one amino acid, two amino acids linked together, three amino acids linked together,

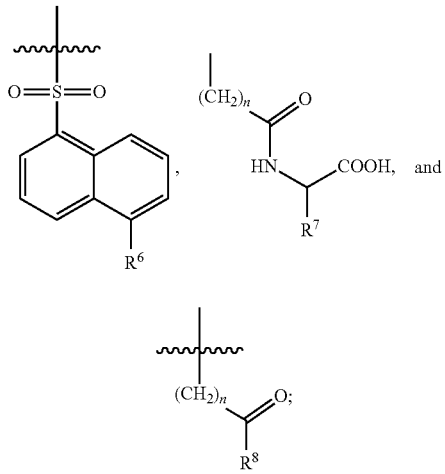

$R^3$, $R^4$, $R^5$, $R^9$, $R^{14}$, $R^{17}$ and $R^{18}$ are each independently selected from the group consisting of hydrogen, halogen, $C_{1-6}$ alkyl, $C_{1-6}$ alkoxy, —C(=O)NH$_2$, —NO$_2$, —NH$_2$, —OH, —NH($R^{15}$), —N($R^{15}$)$_2$, and —SR15; $R^{10}$, $R^{11}$, $R^{12}$, and $R^{13}$ are each independently selected from the group consisting of hydrogen, halogen, $C_{1-6}$ alkyl, $C_{1-6}$ alkoxy, —C(=O)NH$_2$, —NO$_2$, —NH$_2$, —OH, —NH($R^{15}$), —N($R^{15}$)$_2$, and —SR$^{15}$; $R^6$ is $C_{1-6}$ dialkyl amine; $R^7$ is selected from the group consisting of hydrogen and $C_{1-6}$ alkyl; $R^8$ and $R^{15}$ are each independently $C_{1-6}$ alkyl; each $R^{16}$ is independently hydrogen, —OH, or $C_{1-6}$ alkoxy; n is an integer from 0 to 4; p is 1 or 3; and the dashed line represents an optional double bond where said double bond has a configuration selected from the group consisting of cis and trans, with the proviso that at least one of $R^3$, $R^4$, $R^5$, $R^9$, and $R^{14}$ is selected from the group consisting of —NH($R^{15}$), —N($R^{15}$)$_2$, and —SR$^{15}$.

In some embodiments, The compound of Formula I is:

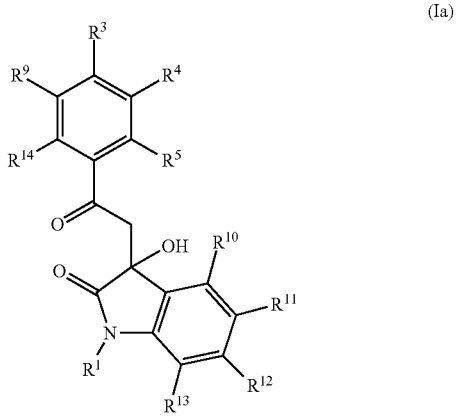

(Ia)

or a pharmaceutically acceptable salt thereof.

In some embodiments, The compound of Formula I is:

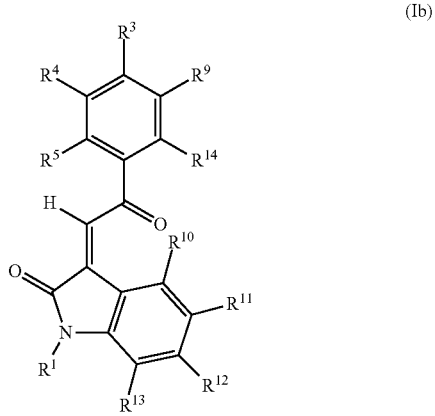

or a pharmaceutically acceptable salt thereof.

In some embodiments, $R^1$ is selected from the group consisting of Leu, Leu-Asp, Leu-Asp-Ala, —CH$_2$—C(=O)—NHCH$_2$COOH, —CH$_2$—C(=O)—(CH$_2$)C(CH$_3$)$_2$,

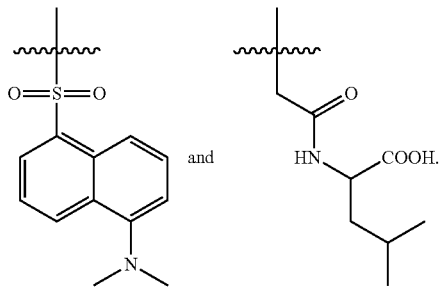 [SMILES: *S(=O)(=O)c1cccc2c(N(C)C)cccc12 ; *CC(=O)NC(CC(C)C)C(=O)O]

In some embodiments, $R^3$ is selected from —NH($R^{15}$), —N($R^{15}$)$_2$, and —S$R^{15}$.

In some embodiments, $R^3$ is —N(CH$_3$)$_2$.

In some embodiments, $R^3$ is —SCH$_3$.

In some embodiments, The compound of Formula I is:

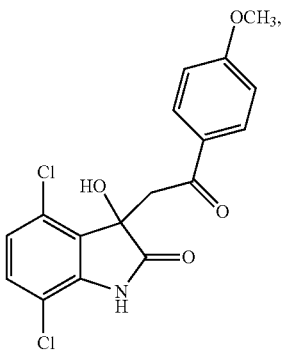

or a pharmaceutically acceptable salt thereof.

Depending upon the substituents present, the small molecule inhibitors can be in a form of a pharmaceutically acceptable salt. The terms "pharmaceutically acceptable salt" as used herein are broad terms, and is to be given its ordinary and customary meaning to a person of ordinary skill in the art (and is not to be limited to a special or customized meaning), and refers without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity.

The compounds of preferred embodiments can include isomers, racemates, optical isomers, enantiomers, diastereomers, tautomers, and cis/trans conformers. All such isomeric forms are included within preferred embodiments, including mixtures thereof. As discussed above, the compounds of preferred embodiments may have chiral centers, for example, they may contain asymmetric carbon atoms and may thus exist in the form of enantiomers or diastereoisomers and mixtures thereof, e.g., racemates. Asymmetric carbon atom(s) can be present in the (R)-, (S)-, or (R,S)-configuration, preferably in the (R)- or (S)-configuration, or can be present as mixtures. Isomeric mixtures can be separated, as desired, according to conventional methods to obtain pure isomers.

The compounds can be in amorphous form, or in crystalline forms. The crystalline forms of the compounds of preferred embodiments can exist as polymorphs, which are included in preferred embodiments. In addition, some of the compounds of preferred embodiments may also form solvates with water or other organic solvents. Such solvates are similarly included within the scope of the preferred embodiments.

Certain Pharmaceutical Compositions

It is generally preferred to administer the inhibitors of preferred embodiments in an intravenous or subcutaneous unit dosage form; however, other routes of administration are also contemplated. Contemplated routes of administration include but are not limited to oral, parenteral, intravenous, and subcutaneous. The inhibitors of preferred embodiments can be formulated into liquid preparations for, e.g., oral administration. Suitable forms include suspensions, syrups, elixirs, and the like. Particularly preferred unit dosage forms for oral administration include tablets and capsules. Unit dosage forms configured for administration once a day are particularly preferred; however, in certain embodiments it can be desirable to configure the unit dosage form for administration twice a day, or more.

The pharmaceutical compositions of preferred embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents.

A pharmaceutically acceptable preservative can be employed to increase the shelf life of the pharmaceutical compositions. Benzyl alcohol can be suitable, although a variety of preservatives including, for example, parabens, thimerosal, chlorobutanol, or benzalkonium chloride can also be employed. A suitable concentration of the preservative is typically from about 0.02% to about 2% based on the total weight of the composition, although larger or smaller amounts can be desirable depending upon the agent selected. Reducing agents, as described above, can be advantageously used to maintain good shelf life of the formulation.

The inhibitors of preferred embodiments can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; $18^{th}$ and $19^{th}$ editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the active ingredient in admixture with excipients suitable for the manufacture of aqueous suspensions.

Formulations for oral use can also be provided as hard gelatin capsules, wherein the active ingredient(s) are mixed with an inert solid diluent, such as calcium carbonate, calcium phosphate, or kaolin, or as soft gelatin capsules. In soft capsules, the inhibitors can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers.

Tablets can be uncoated or coated by known methods to delay disintegration and absorption in the gastrointestinal tract and thereby provide a sustained action over a longer period of time. For example, a time delay material such as glyceryl monostearate can be used. When administered in solid form, such as tablet form, the solid form typically comprises from about 0.001 wt. % or less to about 50 wt. % or more of active ingredient(s), preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets can contain the active ingredients in admixture with non-toxic pharmaceutically acceptable excipients including inert materials. For example, a tablet can be prepared by compression or molding, optionally, with one or more additional ingredients. Compressed tablets can be prepared by compressing in a suitable machine the active ingredients in a free-flowing form such as powder or granules, optionally mixed with a binder, lubricant, inert diluent, surface active or dispersing agent. Molded tablets can be made by molding, in a suitable machine, a mixture of the powdered inhibitor moistened with an inert liquid diluent.

Preferably, each tablet or capsule contains from about 1 mg or less to about 1,000 mg or more of an inhibitor of the preferred embodiments, more preferably from about 10, 20, 30, 40, 50, 60, 70, 80, 90, or 100 mg to about 150, 200, 250, 300, 350, 400, 450, 500, 550, 600, 650, 700, 750, 800, or 900 mg. Most preferably, tablets or capsules are provided in a range of dosages to permit divided dosages to be administered. A dosage appropriate to the patient and the number of doses to be administered daily can thus be conveniently selected. In certain embodiments it can be preferred to incorporate two or more of the therapeutic agents to be administered into a single tablet or other dosage form (e.g., in a combination therapy); however, in other embodiments it can be preferred to provide the therapeutic agents in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Surfactants can also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations can be employed wherein the amifostine or analog(s) thereof is incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments can be added for identification or to characterize different combinations of inhibitor doses.

When administered orally in liquid form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

Pulmonary delivery can also be employed. The compound is delivered to the lungs while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of compound. Typically, each formulation is specific to the type of device employed and can involve the use of an appropriate propellant material, in addition to diluents, adjuvants, and/or carriers useful in therapy.

The compound and/or other optional active ingredients are advantageously prepared for pulmonary delivery in particulate form with an average particle size of from 0.1 µm or less to 10 µm or more, more preferably from about 0.2, 0.3, 0.4, 0.5, 0.6, 0.7, 0.8, or 0.9 µm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 µm. Pharmaceutically acceptable carriers for pulmonary delivery of inhibitor include carbohydrates such as trehalose, mannitol, xylitol, sucrose, lactose, and sorbitol. Other ingredients for use in formulations can include DPPC, DOPE, DSPC, and DOPC. Natural or synthetic surfactants can be used, including polyethylene glycol and dextrans, such as cyclodextran. Bile salts and other related enhancers, as well as cellulose and cellulose derivatives, and amino acids can also be used. Liposomes, microcapsules, microspheres, inclusion complexes, and other types of carriers can also be employed.

Pharmaceutical formulations suitable for use with a nebulizer, either jet or ultrasonic, typically comprise the inhibitor dissolved or suspended in water at a concentration of about 0.01 or less to 100 mg or more of inhibitor per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg per mL of solution. The formulation can also include a buffer and a simple sugar (e.g., for protein stabilization and regulation of osmotic pressure). The nebulizer formulation can also contain a surfactant, to reduce or prevent surface induced aggregation of the inhibitor caused by atomization of the solution in forming the aerosol.

Formulations for use with a metered-dose inhaler device generally comprise a finely divided powder containing the active ingredients suspended in a propellant with the aid of a surfactant. The propellant can include conventional propellants, such as chlorofluorocarbons, hydrochlorofluorocarbons, hydrofluorocarbons, and hydrocarbons. Preferred propellants include trichlorofluoromethane, dichlorodifluoromethane, dichlorotetrafluoroethanol, 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing inhibitor, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

When a compound of the preferred embodiments is administered by intravenous, parenteral, or other injection, it is preferably in the form of a pyrogen-free, parenterally acceptable aqueous solution or oleaginous suspension. Suspensions can be formulated according to methods well known in the art using suitable dispersing or wetting agents and suspending agents. The preparation of acceptable aqueous solutions with suitable pH, isotonicity, stability, and the like, is within the skill in the art. A preferred pharmaceutical composition for injection preferably contains an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils can be employed conventionally as a solvent or suspending medium. For this purpose, any bland fixed oil can be employed including synthetic mono or diglycerides. In addition, fatty acids such as oleic acid can likewise be used in the formation of injectable preparations. The pharmaceutical compositions can also contain stabilizers, preservatives, buffers, antioxidants, or other additives known to those of skill in the art.

The duration of the injection can be adjusted depending upon various factors, and can comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

The compounds of the preferred embodiments can additionally employ adjunct components conventionally found in pharmaceutical compositions in their art-established fashion and at their art-established levels. Thus, for example, the compositions can contain additional compatible pharmaceutically active materials for combination therapy (such as supplementary antimicrobials, antipruritics, astringents, local anesthetics, anti-inflammatory agents, reducing agents, chemotherapeutics and the like), or can contain materials useful in physically formulating various dosage forms of the preferred embodiments, such as excipients, dyes, thickening agents, stabilizers, preservatives or antioxidants. Anti-cancer agents that can be used in combination with the compounds of preferred embodiments include, but are not limited to, vinca alkaloids such as vinblastine and vincristine; anthracyclines such as doxorubicin, daunorubicin, epirubicin; anthracenes such as bisantrene and mitoxantrone; epipodophyllo-toxins such as etoposide and teniposide; and other anticancer drugs such as actinomyocin D, mithomycin C, mitramycin, methotrexate, docetaxel, etoposide (VP-16), paclitaxel, docetaxel, and adriamycin); and immunosuppressants (e.g., cyclosporine A, tacrolimus). In some embodiments, the compounds, compositions and methods provided herein may be in combination with histone deacetylase inhibitors (HDAC), aurora kinase inhibitors, demethylating agents (such as 5-AZA cytidine), immunotherapy with natural killer cells, IGF-IR antibodies, Ewing antigen antibodies, immunosuppressive drugs, and hydroxyurea. Examples of histone deacetylase inhibitors include vorinostat, romidepsin, panobinostat, valproic acid, belinostat, mocetinostat, givinostat, and trichostatin A. Examples of aurora kinase inhibitors include ZM447439, hesperadin, and VX-680. Examples of demethylating agents include 5-azacytidine, 5-azadeoxycytidine, and procaine. Examples of immunosuppressive drugs include 6-mercaptopurine, and azathioprine.

Certain Kits

The compounds of the preferred embodiments can be provided to an administering physician or other health care professional in the form of a kit. The kit is a package which houses a container which contains the compounds in a suitable pharmaceutical composition, and instructions for administering the pharmaceutical composition to a subject. The kit can optionally also contain one or more additional therapeutic agents, e.g., chemotherapeutics currently employed for treating the sarcomas described herein. For example, a kit containing one or more compositions comprising compounds of the preferred embodiments in combination with one or more additional chemotherapeutic agents can be provided, or separate pharmaceutical compositions containing an inhibitor of the preferred embodiments and additional therapeutic agents can be provided. The kit can also contain separate doses of a compound of the preferred embodiments for serial or sequential administration. The kit can optionally contain one or more diagnostic tools and instructions for use. The kit can contain suitable delivery devices, e.g., syringes, and the like, along with instructions for administering the inhibitor(s) and any other therapeutic agent. The kit can optionally contain instructions for storage, reconstitution (if applicable), and administration of any or all therapeutic agents included. The kits can include a plurality of containers reflecting the number of administrations to be given to a subject.

Certain Therapeutic Methods

Some embodiments provided herein relate to methods of treating the Ewing's sarcoma family of tumors (ESFT). ESFT contains the unique fusion protein EWS-FLI1. ESFT affects patients between the ages of 3 and 40 years, with most cases occurring in the second decade. Although the embryologic cell type from which ESFT are derived is unknown, the tumor often grows in close proximity to bone, but can occur as a soft-tissue mass. Over 40% of patients who present with localized tumors will develop recurrent disease and the majority of these will die from ESFT, while 75-80% of patients who present with metastatic ESFT will die within 5 years despite high-dose chemotherapy (Grier H E, Krailo M D, Tarbell N J, et al. Addition of ifosfamide and etoposide to standard chemotherapy for Ewing's sarcoma and primitive neuroectodermal tumor of bone. N Engl J Med 2003; 348(8):694-701). These survival rates have not improved for the past 20 years, even after dose-intensifying chemotherapy. To improve survival and reduce therapy-related morbidity, novel targeted strategies for treating ESFT patients, as provided in the preferred embodiments, can be employed.

ESFT are characterized by a translocation, occurring in 95% of tumors, between the central exons of the EWS gene (Ewing Sarcoma) located on chromosome 22 to the central exons of an ets family gene; either FLI1 (Friend Leukemia Insertion) located on chromosome 11, t(11;22), or ERG located on chromosome 21, t(21;22). The EWS-FLI1 fusion transcript encodes a 55 kDa protein (electrophoretic motility of approximately 68 kD) with two primary domains. The EWS domain is a potent transcriptional activator, while the FLI1 domain contains a highly conserved ets DNA binding domain (May W A, Lessnick S L, Braun B S, et al. The Ewing's sarcoma EWS/FLI-1 fusion gene encodes a more potent transcriptional activator and is a more powerful transforming gene than FLI-1. Mol Cell Biol 1993; 13(12): 7393-8); the resulting EWS-FLI1 fusion protein acts as an aberrant transcription factor. EWS-FLI1 transformation of mouse fibroblasts requires both the EWS and FLI1 functional domains to be intact (May W A, Gishizky M L, Lessnick S L, et al. Ewing sarcoma 11;22 translocation produces a chimeric transcription factor that requires the DNA-binding domain encoded by FLI1 for transformation. Proc Natl Acad Sci USA 1993; 90(12):5752-6).

EWS-FLI1 is an outstanding therapeutic target, in that it is expressed only in tumor cells and is required to maintain the growth of ESFT cell lines. Reduced expression levels of EWS-FLI1 using either antisense oligodeoxynucleotides (ODN) (Toretsky J A, Connell Y, Neckers L, Bhat N K. Inhibition of EWS-FLI-1 fusion protein with antisense oligodeoxynucleotides. J Neurooncol 1997; 31(1-2):9-16; Tanaka K, Iwakuma T, Harimaya K, Sato H, Iwamoto Y. EWS-Fli1 antisense oligodeoxynucleotide inhibits proliferation of human Ewing's sarcoma and primitive neuroectodermal tumor cells. J Clin Invest 1997; 99(2):239-47) or small interfering RNAs (siRNA) (Ouchida M, Ohno T, Fujimura Y, Rao V N, Reddy E S. Loss of tumorigenicity of Ewing's sarcoma cells expressing antisense RNA to EWS-fusion transcripts. Oncogene 1995; 11(6):1049-54; Maksimenko A, Malvy C, Lambert G, et al. Oligonucleotides targeted against a junction oncogene are made efficient by nanotechnologies. Pharm Res 2003; 20(10):1565-7; Kovar H, Aryee D N, Jug G, et al. EWS/FLI-1 antagonists induce growth inhibition of Ewing tumor cells in vitro. Cell Growth Differ 1996; 7(4):429-37) cause decreased proliferation of ESFT cell lines and regression of tumors in nude mice. Recent advances in nanotechnology have improved the delivery and controlled release of siRNA, yet neither antisense ODN nor siRNA reduction of EWS-FLI1 in humans is possible with current technologies (Maksimenko A, Malvy C, Lambert G, et al. Oligonucleotides targeted against a junction oncogene are made efficient by nanotechnologies. Pharm Res 2003; 20(10):1565-7; Lambert G, Bertrand J R, Fattal E, et al. EWS fli-1 antisense nanocapsules inhibits Ewing sarcoma-related tumor in mice. Biochem Biophys Res Commun 2000; 279(2):401-6). One interesting approach to EWS-FLI1 targeting used comparative expression between siRNA reduced EWS-FLI1 and a library of small molecules, which led to a current clinical trial with Ara-C (Stegmaier K, Wong J S, Ross K N, et al. Signature-based small molecule screening identifies cytosine arabinoside as an EWS/FLI modulator in Ewing sarcoma. PLoS medicine 2007; 4(4):e122). This method of identifying Ara-C also indicated doxorubicin and puromycin would reduce EWS-FLI1 levels. Doxorubicin is currently used as standard therapy for ESFT patients and yet, survival is far from acceptable (Grier H E, Krailo M D, Tarbell N J, et al. Addition of ifosfamide and etoposide to standard chemotherapy for Ewing's sarcoma and primitive neuroectodermal tumor of bone. N Engl J Med 2003; 348(8):694-701). The use of Ara-C in ESFT patients is currently being evaluated in a Phase II trial. While it is hoped that this represents a needed clinical breakthrough, it certainly demonstrates the importance of small molecule targeting of EWS-FLI1. The preferred embodiments provide small molecule protein-protein interaction inhibitors (SMPPII) that disrupt EWS-FLI1 from critical protein partners, thereby achieving tumor specificity and more precise targeting of EWS-FLI1.

There is sufficient evidence to conclude that EWS-FLI1 fusion protein functions differently than either untranslocated EWS or FLI1 (May W A, Gishizky M L, Lessnick S L, et al. Ewing sarcoma 11;22 translocation produces a chimeric transcription factor that requires the DNA-binding domain encoded by FLI1 for transformation. Proc Natl Acad Sci USA 1993; 90(12):5752-6). Changes in gene expression profiles of EWS-FLI1-expressing cell lines (Braun B S, Frieden R, Lessnick S L, May W A, Denny C T. Identification of target genes for the Ewing's sarcoma EWS/FLI fusion protein by representational difference analysis. Mol Cell Biol 1995; 15(8):4623-30) or tumor cells taken from ESFT patients, compared to tumors lacking EWS-FLI1 expression, indicate that EWS-FLI1 may play a role in transcriptional regulation (Khan J, Wei J S, Ringner M, et al. Classification and diagnostic prediction of cancers using gene expression profiling and artificial neural networks. Nat Med 2001; 7(6):673-9; Baer C, Nees M, Breit S, et al. Profiling and functional annotation of mRNA gene expression in pediatric rhabdomyosarcoma and Ewing's sarcoma. Int J Cancer 2004; 110(5):687-94). While a clear picture of the mechanism of EWS-FLI1-regulated gene expression has yet to emerge, this activity is likely the result of direct or secondary interactions between EWS-FLI1 and regulators of RNA synthesis and splicing (Uren A, Toretsky J A. Ewing's Sarcoma Oncoprotein EWS-FLI1: the Perfect Target without a Therapeutic Agent. Future Onc 2005; 1(4):521-8).

EWS-FLI1 is a great therapeutic target since it is only expressed in tumor cells; however, the ability to target this tumor-specific oncogene has previously not been successful. One of the challenges towards small molecule development is that EWS-FLI1 lacks any know enzymatic domains, and enzyme domains have been thought to be critical for targeted therapeutics. In addition, EWS-FLI1 is a disordered protein, indicating that it does not exhibit a rigid structure that can be used for structure based drug design (Uren A, Tcherkasskaya O, Toretsky J A. Recombinant EWS-FLI1 oncoprotein activates transcription. Biochemistry 2004; 43(42):13579-89). In fact, the disordered nature of EWS-FLI1 is critical for its transcriptional regulation (Ng K P, Potikyan G, Savene R O, Denny C T, Uversky V N, Lee K A. Multiple aromatic side chains within a disordered structure are critical for transcription and transforming activity of EWS family oncoproteins. Proc Natl Acad Sci USA 2007; 104(2):479-84). Disordered proteins are considered as more attractive targets for small molecule protein-protein interaction inhibitors specifically because of their biochemical disordered properties (Cheng Y, LeGall T, Oldfield C J, et al. Rational drug design via intrinsically disordered protein. Trends Biotechnol 2006; 24(10):435-42).

EWS-FLI1 binds RNA helicase A in vitro and in vivo. It is believed that protein-protein interactions of EWS-FLI1 may contribute to its oncogenic potential; therefore, novel proteins have been sought that directly interact with and functionally modulate EWS-FLI1. Recombinant EWS-FLI1 that is transcriptionally active (Uren A, Tcherkasskaya O, Toretsky J A. Recombinant EWS-FLI1 oncoprotein activates transcription. Biochemistry 2004; 43(42):13579-89) was used as a target for screening a commercial peptide phage display library. Twenty-eight novel peptides that differentially bind to EWS-FLI1 were identified from phage sequencing. A National Center for Biotechnology Information database search for human proteins homologous to these peptides identified a peptide that was homologous to aa 823-832 of the human RNA helicase A, (RHA, gene bank accession number A47363) (Toretsky J A, Erkizan V, Levenson A, et al. Oncoprotein EWS-FLI1 activity is enhanced by RNA helicase A. Cancer Res 2006; 66(11):5574-81).

RHA, a member of the highly conserved DEXD/H box helicase family of proteins, is an integral, multifunctional member of the human transcriptome (Zhang S, Grosse F. Multiple functions of nuclear DNA helicase II (RNA helicase A) in nucleic acid metabolism. Acta Biochim Biophys Sin (Shanghai) 2004; 36(3):177-83; von Hippel P H, Delagoutte E. A general model for nucleic acid helicases and their "coupling" within macromolecular machines. Cell 2001; 104(2):177-90). These proteins are involved in diverse functions in a variety of organisms, from archaea, eubacteria, lower and higher eukaryotes and a number of viruses, including the positive-sense RNA viruses of the Flavivirus family. RHA is a transcriptional coactivator for NF-KB, and has been shown to form complexes with Creb-binding protein (CBP) (Nakajima T, Uchida C, Anderson S F, et al. RNA helicase A mediates association of CBP with RNA polymerase II. Cell 1997; 90(6):1107-12), RNA Polymerase II (Nakajima T, Uchida C, Anderson S F, et al. RNA helicase A mediates association of CBP with RNA polymerase II. Cell 1997; 90(6):1107-12), the breast cancer tumor suppressor BRCA1 (Anderson S F, Schlegel B P, Nakajima T, Wolpin E S, Parvin J D. BRCA1 protein is linked to the RNA polymerase II holoenzyme complex via RNA helicase A. Nat Genet 1998; 19(3):254-6), and, most recently, EWS-FLI1 (Toretsky J A, Erkizan V, Levenson A, et al. Oncoprotein EWS-FLI1 activity is enhanced by RNA helicase A. Cancer Res 2006; 66(11):5574-81). EWS-FLI1 binds to a region of RHA that is unique and not known as a binding site for any of the other RHA binding partners (Toretsky J A, Erkizan V, Levenson A, et al. Oncoprotein EWS-FLI1 activity is enhanced by RNA helicase A. Cancer Res 2006; 66(11):5574-81). RHA expression enhanced EWS-FLI1 mediated anchorage-independent colony formation, while an inactivating mutation of RHA prevented colony formation (Toretsky J A, Erkizan V, Levenson A, et al. Oncoprotein EWS-FLI1 activity is enhanced by RNA helicase A. Cancer Res 2006; 66(11):5574-81). This structural and function interaction is the basis for the therapeutic agents of preferred embodiments.

Despite the importance of transcription in tumorigenesis, the role of helicases in this process has not been well-studied. RHA is an integral member of the human transcriptome with diverse functions (Zhang S, Grosse F. Multiple functions of nuclear DNA helicase II (RNA helicase A) in nucleic acid metabolism. Acta Biochim Biophys Sin (Shanghai) 2004; 36(3):177-83; von Hippel P H, Delagoutte E. A general model for nucleic acid helicases and their "coupling" within macromolecular machines. Cell 2001; 104(2): 177-90). Our recently published data show that RHA interacts with the multifunctional EWS-FLI1 oncoprotein (Toretsky J A, Erkizan V, Levenson A, et al. Oncoprotein EWS-FLI1 activity is enhanced by RNA helicase A. Cancer Res 2006; 66(11):5574-81). This interaction could account for the observed ability of EWS-FLI1 to function in both transcription initiation and post-transcriptional RNA modification. RNA helicases are also known to bind and act as a bridge for some of the same factors that have been identified as binding partners for EWS-FLI1, including the splicing factor U1C (Chen J Y, Stands L, Staley J P, Jackups R R, Jr., Latus L J, Chang T H. Specific alterations of U1-C protein or U1 small nuclear RNA can eliminate the requirement of Prp28p, an essential DEAD box splicing factor. Mol Cell 2001; 7(1):227-32; Knoop L L, Baker S J. The splicing factor U1C represses EWS/FLI-mediated transactivation. J Biol Chem 2000; 275(32):24865-71), Creb-binding protein (CBP) (Nakajima T, Uchida C, Anderson S F, et al. RNA helicase A mediates association of CBP with RNA polymerase II. Cell 1997; 90(6):1107-12) and RNA Polymerase II (Nakajima T, Uchida C, Anderson S F, et al. RNA helicase A mediates association of CBP with RNA polymerase II. Cell 1997; 90(6):1107-12). RHA may perform a similar function for EWS-FLI1 and RNA Pol II, acting in the recruitment of key processing proteins. RHA may also contribute to ESFT oncogenesis by maintaining EWS-FLI1 as part of a large transcriptional complex whose function relies on the ATPase activity of RHA as an energy source. Finally, helicases, like RHA, can stabilize mRNA species (lost I, Dreyfus M. mRNAs can be stabilized by DEAD-box proteins. Nature 1994; 372(6502):193-6). The stabilization and metabolism of EWS-FLI1 transcribed mRNA by RHA may augment the oncogenic nature of EWS-FLI1.

While EWS-FLI1 is quite specific to ESFT cells, EWS and RHA are ubiquitously expressed. The region between EWS-FLI1 and RHA are targeted by molecular therapeutics that may have specificity; since EWS-FLI1 is expressed only in tumors and the interaction points with RHA may be unique. Therapeutic agents, namely, small molecule protein-protein interaction inhibitors, are provided herein to inhibit EWS-FLI1 function.

Most translocation-fusion protein sarcomas portend a poor prognosis, including ESFT. The chromosomal translocation t(11;22), leading to the unique and critical fusion protein EWS-FLI1, is a perfect cancer target. Many other sarcomas share similar translocation variants (Table 2. from Helman L J, Meltzer P. Mechanisms of sarcoma development. Nat Rev Cancer 2003; 3(9):685-94).

EWS-FLI1 translocations have been reported in solid pseudopapillaryneoplasms of the pancreas (Maitra A., et al., Detection of t(11;22)(q24;q12) translocation and EWS-FLI-1 fusion transcript in a case of solid pseudopapillary tumor of the pancreas. Pediatr Dev Pathol 2000; 3:603-605), however the role of EWS-FLI1 in all solid pseudopaillary neoplasms remains to be resolved (Katharina Tiemann et al., Solid pseudopapillary neoplasms of the pancreas are associated with FLI-1 expression, but not with EWS/FLI-1 translocation).

EWS or FLI1 homologues are partners in translocations that occur in a wide range of sarcomas and leukemias. EWS, or its homologue TLS or FUS, is involved in chromosomal translocations of clear cell sarcoma, myxoid liposarcoma, desmoplastic small round cell tumor, chondrosarcoma and acute myeloid leukemia. FLI1 belongs to the ets family of genes. The FLI1 homologue ERG is translocated in approximately 10% of Ewing's sarcomas and 20% of acute myeloid leukemias. This suggests that EWS-FLI1 can serve as model system that might impact upon a family of diseases (related by translocation partners) that affect a large number of patients (Uren A., Tcherkasskaya O. and Toretsky J. A. Recombinant EWS-FLI1 oncoprotein activates transcription. Biochemistry 43(42) 13579-89 (2004)).

ERG is also translocated in prostate cancer, where the TMPRSS2:ERG fusion suggests a distinct molecular subtype that may define risk for disease progression (F. Demichelis et al., TMPRSS2:ERG gene fusion associated with lethal cancer in a watchful waiting cohort. Oncogene (2007) 26, 4596-4599). Other diseases where translocations of EWS or FLI1 family members have been observed include congenital fibrosarcoma and cellular mesoblastic nephroma where the ets family member ETV6 is juxtaposed with NTRK3. Other translocation gene fusions include chronic myeloid leukemia that leads to expression of the BCR-ABL fusion protein, and synovial sarcoma where the SYT gene from chromosome 18 is juxtaposed with either SSX1 or SSX2 from the X chromosome (Aykut Uren and Jeffrey A. Toretsky, Pediatric malignancies provide unique cancer therapy targets. Curr Opin Pediatr 17:14-19 (2005)).

Therefore, the therapeutic agents of the preferred embodiments have potential for application in many other tumors. More broadly, some of the most difficult leukemias also have translocation-generated fusion proteins involving the mixed-lineage leukemia gene (MLL,11q23), and our work could serve as a paradigm for a very treatment-resistant group of cancers (Pui C H, Chessells J M, Camitta B, et al. Clinical heterogeneity in childhood acute lymphoblastic leukemia with 11q23 rearrangements. Leukemia 2003; 17(4):700-6.). Thus embodiments include cancers where translocations have occurred. Translocation fusion genes are listed in Table 1.

TABLE 1

| Translocation | Genes | Type of fusion gene |
|---|---|---|
| Ewing's sarcoma | | |
| t(11; 22)(q24; q12) | EWSR1-FLI1 | Transcription factor |
| t(21; 22)(q22; q12) | EWSR1-ERG | Transcription factor |
| t(7; 22)(p22; q12) | EWSR1-ETV1 | Transcription factor |
| t(17; 22)(q21; q12) | EWSR1-ETV4 | Transcription factor |
| t(2; 22)(q33; q12) | EWSR1-FEV | Transcription factor |
| Clear-cell sarcoma | | |
| t(12; 22)(q13; q12) | EWSR1-ATF1 | Transcription factor |
| Desmoplastic small round-cell tumor | | |
| t(11; 22)(p13; q12) | EWSR1-WT1 | Transcription factor |
| Myxoid chondrosarcoma | | |
| t(9; 22)(q22-31; q11-12) | EWSR1-NR4A3 | Transcription factor |
| Myxoid liposarcoma | | |
| t(12; 16)(q13; p11) | FUS-DDIT3 | Transcription factor |
| t(12; 22)(q13; q12) | EWSR1-DDIT3 | Transcription factor |
| Alveolar rhabdomyosarcoma | | |
| t(2; 13)(q35; q14) | PAX3-FOXO1A | Transcription factor |
| t(1; 13)(p36; q14) | PAX7-FOXO1A | Transcription factor |
| Synovial sarcoma | | |
| t(X; 18)(p11; q11) | SYT-SSX | Transcription factor |
| Dermatofibrosarcoma protuberans | | |
| t(17; 22)(q22; q13) | COL1A1-PDGFB | Growth factor |
| Congenital fibrosarcoma | | |
| t(12; 15)(p13; q25) | ETV6-NTRK3 | Transcription-factor receptor |
| Inflammatory myofibroblastic tumor | | |
| 2p23 rearrangements | TMP3-ALK; TMP4-ALK | Growth-factor receptor |
| Alveolar soft-part sarcoma | | |
| t(X; 17)(p11.2; q25) | ASPL-TFE3 | Transcription factor |

Certain Indications

Certain compounds, compositions and methods provided herein can be used to treat a number of disorders such as a tumor comprising a translocation gene fusion, Ewing's sarcoma, clear cell sarcoma, myxoid liposarcoma, desmoplastic small round-cell tumor, myxoid chondrosarcoma, acute myeloid leukemia, congenital fibrosarcoma, prostate cancer, breast cancer, and pancreatic cancer. In some embodiments, the cancer is lung adenocarcinoma, or glioblastoma multiforme. In some embodiments, the cancer comprises a translocation comprising an ETS gene selected from the group consisting of FLI1, ETV1, ETV4, ERG, ETS1, and ETS2.

EXAMPLES

The following examples, including experiments and results achieved, are provided for illustrative purposes only and are not to be construed as limiting the present invention. Where chemical structures depict atoms having an unfilled valency, it is to be understood that the valency is satisfied with one or more hydrogen atoms.

Example 1

Synthesis of 4,7 Dichloroisatin Analogs

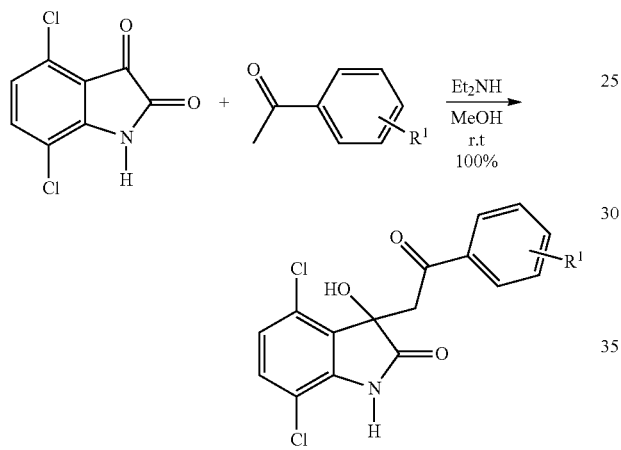

An appropriate acetophenone and 4, 7-dichloroisatin were condensed in the presence of a catalytic amount of diethylamine to prepare the desired compound in quantitative yield. Example compounds: $R^1$=4'-CN (PT-1-11); 2'-OCH$_3$ (PT-1-12); 3'-OCH$_3$ (PT-1-18); 2',4'-OCH$_3$ (PT-1-19); 2',3'-OCH$_3$ (PT-1-20); 3',4'OCH$_3$ (PT-1-21); 3',5'OCH$_3$ (PT-1-22); 2',3',4',-OCH$_3$ (PT-1-23); 3',4',5'-OCH$_3$ (PT-1-13); 4'-OC$_2$H$_5$ (PT-1-14); 4'-CF$_3$ (PT-1-15); 4'-OCF$_3$ (PT-1-16); 4'-N(CH$_3$)$_2$ (PT-1-17); 4'-OPh (PT-1-60); 4'-SCH$_3$ (PT-1-67); and 4'-C(CH$_3$)$_2$ (PT-1-67).

Example 2

Synthesis of Dehydrated 4,7 Dichloroisatin Analogs

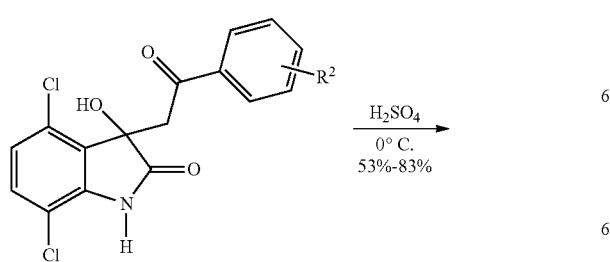

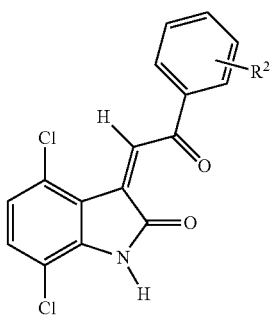

A solution of 4,7-dichloroisatin in 96% H$_2$SO$_4$ was stirred at room temperature to yield the reduced analogs. Example compounds: R2=4'-OCH3 (PT-1-33); 2',4'-OCH3 (PT-1-39); 2',3',4',-OCH3 (PT-1-41); 4'-OC2H5 (PT-1-43); and 4'-N(CH3)2 (PT-1-38).

Example 3

Synthesis of Reduced 4,7 Dichloroisatin Analogs

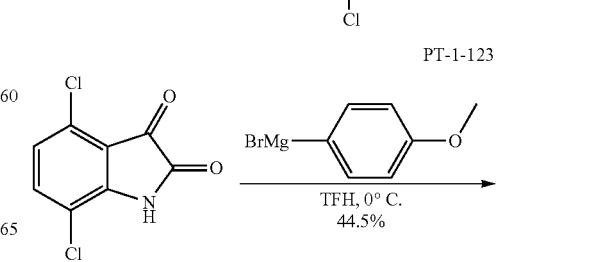

-continued

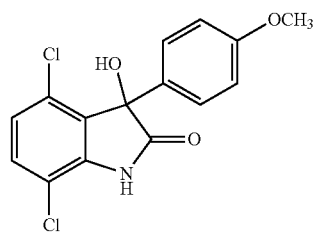

PT-1-155

Example 4

Synthesis of Reduced 4,7 Dichloroisatin Pyridine Derivatives

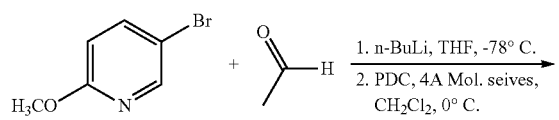

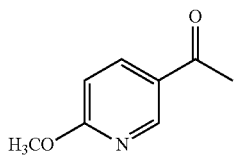

PT-1-173

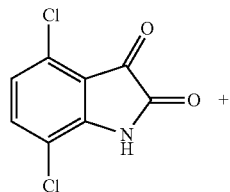

-continued

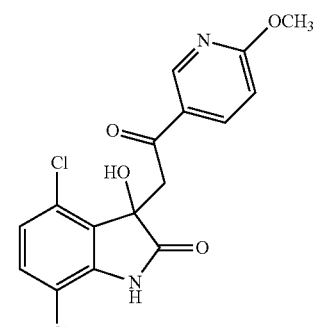

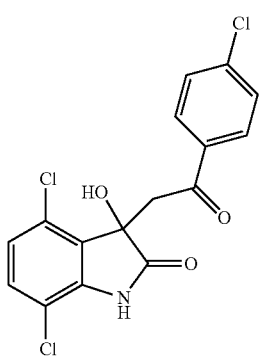 [SMILES: O=C(CC1(O)C(=O)Nc2c(Cl)ccc(Cl)c21)c1ccc(Cl)cc1]

PT-1-175

Example 5

Biological Activity of Certain Compounds

Compounds provided in Table 2 were prepared using methods similar to those described herein. The structures and $IC_{50}$ activities of particular compounds in PANC1 (a human pancreatic carcinoma), TC32 (human ESFT cell line), and TC71 (human ESFT cell line) cells are summarized in Table 2.

TABLE 2

| | | $IC_{50}$ (µM) | | |
|---|---|---|---|---|
| Example | Structure | PANC 1 | TC32 | TC71 |
| YK-4-275 | | 11 | 40 | 23.95 |

TABLE 2-continued

| Example | Structure | IC$_{50}$ (μM) | | |
|---|---|---|---|---|
| | | PANC 1 | TC32 | TC71 |
| YK-4-279 | [structure: 4,7-dichloro-3-hydroxy-3-[2-(4-methoxyphenyl)-2-oxoethyl]indolin-2-one] | 19.98; 33.96 | 0.9395; 0.7657 | 0.9178; 1.426 |
| YK-4-280 | [structure: 4,7-dichloro-3-hydroxy-3-[2-(4-methylphenyl)-2-oxoethyl]indolin-2-one] | 40 | 12.11 | 30.08 |
| YK-4-281 | [structure: 4,7-dichloro-3-hydroxy-3-[2-(3-chlorophenyl)-2-oxoethyl]indolin-2-one] | 40 | 7.218 | 29.61 |
| YK-4-283 | [structure: 4,7-dichloro-3-hydroxy-3-[2-(4-bromophenyl)-2-oxoethyl]indolin-2-one] | 12.66 | 8.911 | 25.96 |

TABLE 2-continued
| Example | Structure | IC$_{50}$ (μM) | | |
|---|---|---|---|---|
| | | PANC 1 | TC32 | TC71 |
| YK-4-284 | 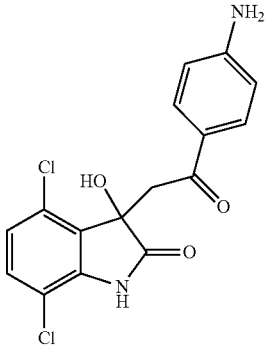 | 40 | 40 | 40 |
| YK-4-285 | 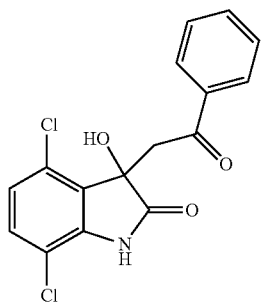 [SMILES: O=C(CC1(O)C(=O)Nc2c(Cl)ccc(Cl)c21)c1ccccc1] | 40 | 40 | 40 |
| YK-4-286 | 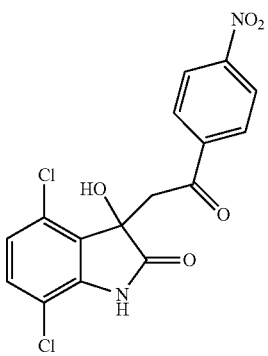 [SMILES: O=C(CC1(O)C(=O)Nc2c(Cl)ccc(Cl)c21)c1ccc([N+](=O)[O-])cc1] | 40 | 4.631 | 9.149 |
| YK-4-287 | 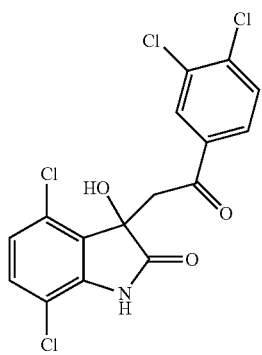 [SMILES: O=C(CC1(O)C(=O)Nc2c(Cl)ccc(Cl)c21)c1ccc(Cl)c(Cl)c1] | 12.6 | 6.32 | 15.82 |

TABLE 2-continued

| Example | Structure | IC$_{50}$ (μM) | | |
| --- | --- | --- | --- | --- |
| | | PANC 1 | TC32 | TC71 |
| YK-4-288 | 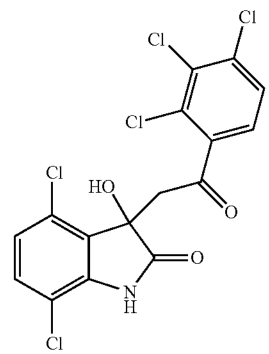 [SMILES: O=C(CC1(O)C(=O)Nc2c(Cl)ccc(Cl)c21)c1ccc(Cl)c(Cl)c1Cl] | 40 | 3.002 | 9.345 |
| YK-4-289 | 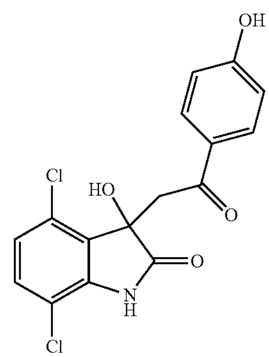 [SMILES: O=C(CC1(O)C(=O)Nc2c(Cl)ccc(Cl)c21)c1ccc(O)cc1] | 40 | 40 | 40 |
| PT-1-11 | 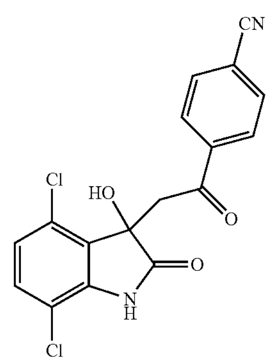 [SMILES: N#Cc1ccc(C(=O)CC2(O)C(=O)Nc3c(Cl)ccc(Cl)c32)cc1] | 40 | 10.34 | 12.28 |
| PT-1-14 | 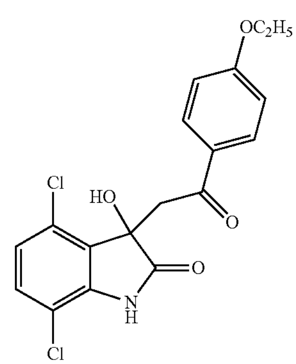 [SMILES: CCOc1ccc(C(=O)CC2(O)C(=O)Nc3c(Cl)ccc(Cl)c32)cc1] | 11.11 | 2.698 | 3.568 |

TABLE 2-continued

| Example | Structure | IC$_{50}$ (μM) | | |
|---|---|---|---|---|
| | | PANC 1 | TC32 | TC71 |
| PT-1-15 | 4,7-dichloro-3-hydroxy-3-[2-oxo-2-(4-trifluoromethylphenyl)ethyl]-1,3-dihydro-2H-indol-2-one | 10.91 | 2.952 | 6.941 |
| PT-1-17 | 4,7-dichloro-3-[2-(4-dimethylaminophenyl)-2-oxoethyl]-3-hydroxy-1,3-dihydro-2H-indol-2-one | 40; 40 | 0.2589; 0.2836 | 0.4008; 0.2945 |
| PT-1-18 | 4,7-dichloro-3-hydroxy-3-[2-(3-methoxyphenyl)-2-oxoethyl]-1,3-dihydro-2H-indol-2-one | 40 | 40 | 40 |
| PT-1-19 | 4,7-dichloro-3-hydroxy-3-[2-(2,4-dimethoxyphenyl)-2-oxoethyl]-1,3-dihydro-2H-indol-2-one | 22.94 | 2.609 | 2.819 |

TABLE 2-continued

| Example | Structure | IC$_{50}$ (μM) | | |
| --- | --- | --- | --- | --- |
| | | PANC 1 | TC32 | TC71 |
| PT-1-22 | 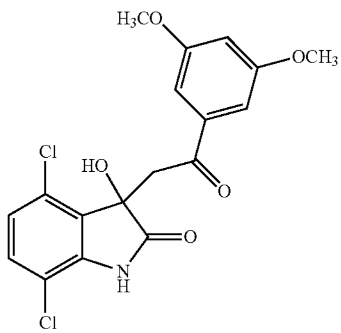 [SMILES: COc1cc(OC)cc(C(=O)CC2(O)C(=O)Nc3c(Cl)ccc(Cl)c32)c1] | 40 | 8.988 | 40 |
| PT-1-23 | 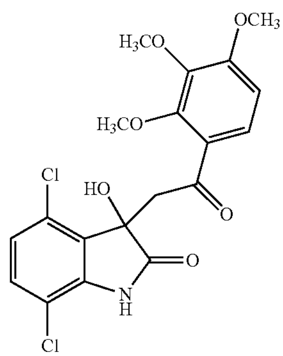 [SMILES: COc1ccc(C(=O)CC2(O)C(=O)Nc3c(Cl)ccc(Cl)c32)c(OC)c1OC] | 40 | 2.698 | 4.422 |
| PT-1-38 | 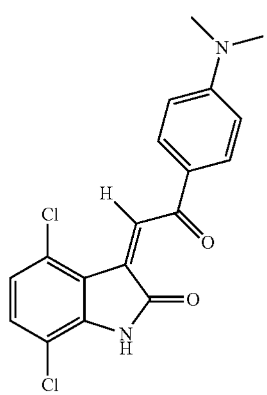 [SMILES: CN(C)c1ccc(C(=O)/C=C2\C(=O)Nc3c(Cl)ccc(Cl)c32)cc1] | 15.5; 40 | 0.2908; 0.3833 | 40; 0.5682 |
| PT-1-39 | 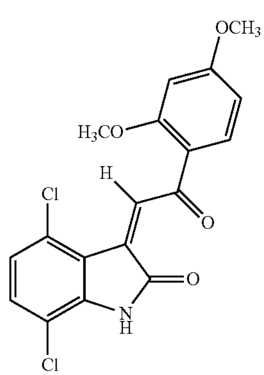 [SMILES: COc1ccc(C(=O)/C=C2\C(=O)Nc3c(Cl)ccc(Cl)c32)c(OC)c1] | 5.413; 6.763 | 1.052; 1.664 | 1.806; 2.318 |

TABLE 2-continued

| Example | Structure | IC$_{50}$ (μM) | | |
|---|---|---|---|---|
| | | PANC 1 | TC32 | TC71 |
| PT-1-41 | 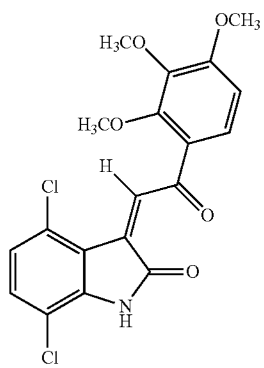 [SMILES: COc1ccc(C(=O)/C=C2\C(=O)Nc3c(Cl)ccc(Cl)c32)c(OC)c1OC] | 2.855; 5.158 | 1.194; 1.611 | 2.142; 1.599 |
| PT-1-43 | 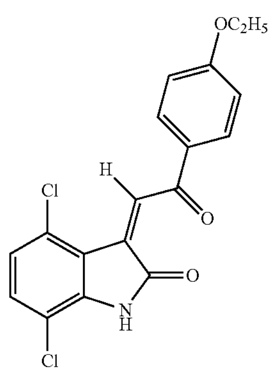 [SMILES: CCOc1ccc(C(=O)/C=C2\C(=O)Nc3c(Cl)ccc(Cl)c32)cc1] | 10.98 | 1.409 | 5.655 |
| PT-1-53 | 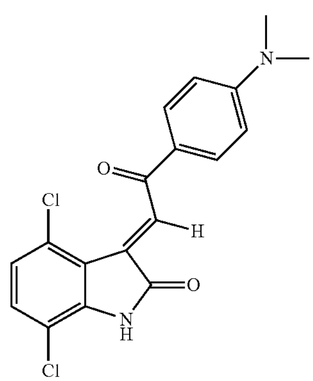 [SMILES: CN(C)c1ccc(C(=O)/C=C2/C(=O)Nc3c(Cl)ccc(Cl)c32)cc1] | 2.202 | 40 | 4.08 |
| PT-1-54 | 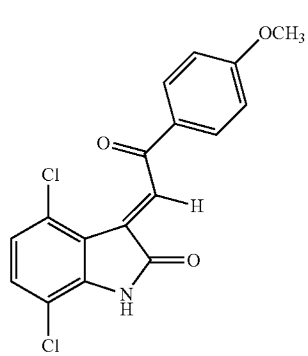 [SMILES: COc1ccc(C(=O)/C=C2/C(=O)Nc3c(Cl)ccc(Cl)c32)cc1] | 2.127; 40 | 1.498; 2.57 | 1.362; 2.202 |

TABLE 2-continued
| Example | Structure | IC$_{50}$ (μM) | | |
|---|---|---|---|---|
| | | PANC 1 | TC32 | TC71 |
| PT-1-60 | 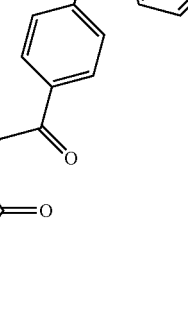 | 40 | 40 | 40 |
| PT-1-64 | | 40 | 32.8 | 40 |
| PT-1-67 | 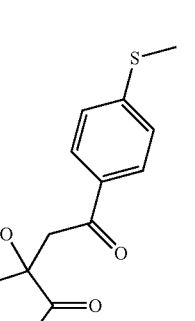 | 28.1; 40 | 0.9822; 1.203 | 0.9086; 1.409 |
| PT-1-69 | 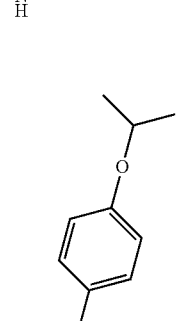 | 40 | 40 | 40 |
| PT-1-267 | 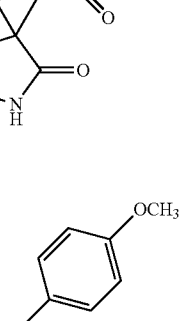 | 40 | 40 | 40 |

TABLE 2-continued

| Example | Structure | IC$_{50}$ (μM) | | |
| --- | --- | --- | --- | --- |
| | | PANC 1 | TC32 | TC71 |
| PT-1-271 | 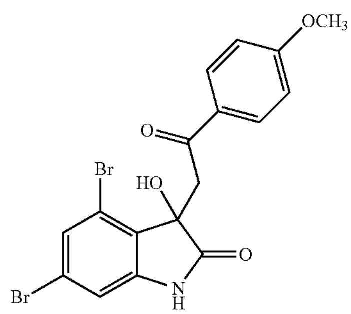 [SMILES: COc1ccc(C(=O)CC2(O)C(=O)Nc3cc(Br)cc(Br)c32)cc1] | 40 | 40 | 40 |
| PT-1-275 | 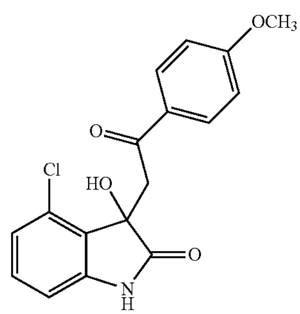 [SMILES: COc1ccc(C(=O)CC2(O)C(=O)Nc3cccc(Cl)c32)cc1] | 40 | 40 | 40 |
| PT-2-39 | 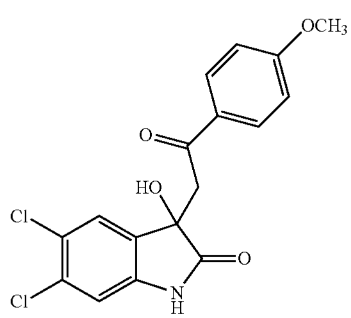 | 40 | 40 | 40 |
| PT-2-52 | 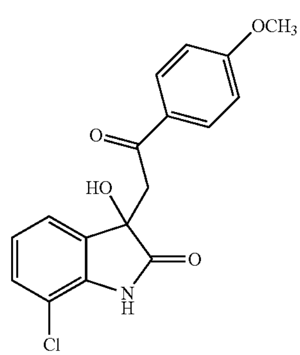 [SMILES: COc1ccc(C(=O)CC2(O)C(=O)Nc3c(Cl)cccc32)cc1] | 40 | 40 | 40 |

TABLE 2-continued

| Example | Structure | IC$_{50}$ (μM) | | |
|---|---|---|---|---|
| | | PANC 1 | TC32 | TC71 |
| PT-2-56 | 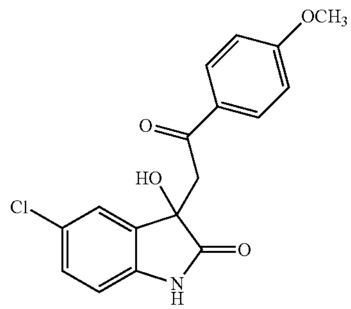 [SMILES: COc1ccc(C(=O)CC2(O)C(=O)Nc3ccc(Cl)cc32)cc1] | 40 | 12.36 | 40 |
| PT-2-59 | 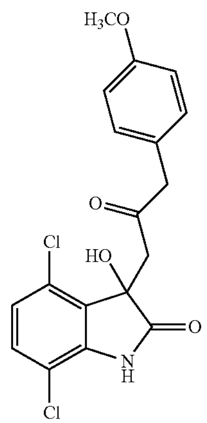 [SMILES: COc1ccc(CC(=O)CC2(O)C(=O)Nc3c(Cl)ccc(Cl)c32)cc1] | 40 | 40 | 40 |
| PT-2-64 | 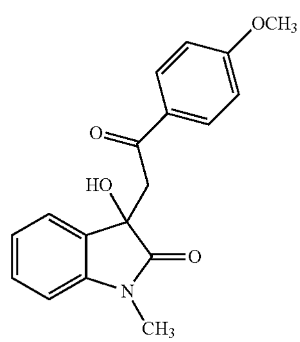 [SMILES: COc1ccc(C(=O)CC2(O)C(=O)N(C)c3ccccc32)cc1] | 40 | 40 | 40 |
| PT-2-69 | 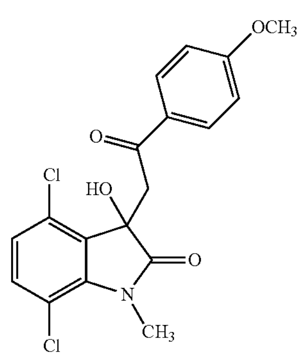 [SMILES: COc1ccc(C(=O)CC2(O)C(=O)N(C)c3c(Cl)ccc(Cl)c32)cc1] | 40; 40 | 2.178; 2.305 | 0.7145; 2.341 |

TABLE 2-continued

| Example | Structure | IC$_{50}$ (µM) | | |
| --- | --- | --- | --- | --- |
| | | PANC 1 | TC32 | TC71 |
| PT-2-71 | 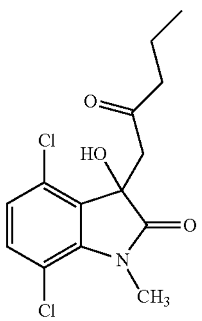 [SMILES: CCCC(=O)CC1(O)C(=O)N(C)c2c(Cl)ccc(Cl)c21] | 40 | 40 | 40 |
| YK-4-276 | 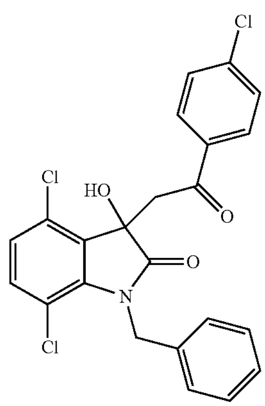 [SMILES: O=C(CC1(O)C(=O)N(Cc2ccccc2)c2c(Cl)ccc(Cl)c21)c1ccc(Cl)cc1] | 40 | 40 | 40 |
| YK-4-277 | 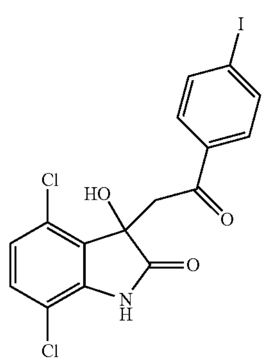 [SMILES: O=C(CC1(O)C(=O)Nc2c(Cl)ccc(Cl)c21)c1ccc(I)cc1] | 40 | 40 | 40 |
| YK-4-278 | 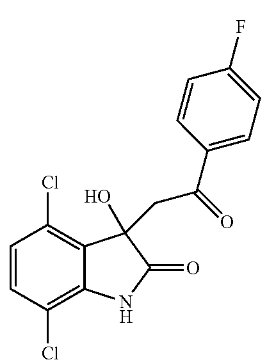 [SMILES: O=C(CC1(O)C(=O)Nc2c(Cl)ccc(Cl)c21)c1ccc(F)cc1] | 40 | 40 | 40 |

TABLE 2-continued

| Example | Structure | IC₅₀ (μM) | | |
| --- | --- | --- | --- | --- |
| | | PANC 1 | TC32 | TC71 |
| YK-4-282 | 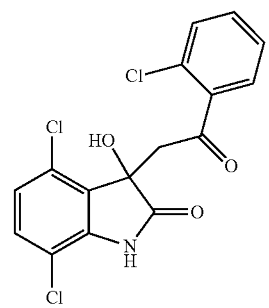 [SMILES: O=C(CC1(O)C(=O)Nc2c(Cl)ccc(Cl)c21)c1ccccc1Cl] | 40 | 40 | 40 |
| PT-1-12 | 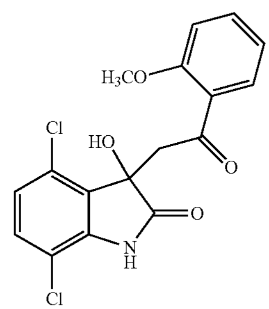 [SMILES: COc1ccccc1C(=O)CC1(O)C(=O)Nc2c(Cl)ccc(Cl)c21] | 40 | 40 | 40 |
| PT-1-13 | 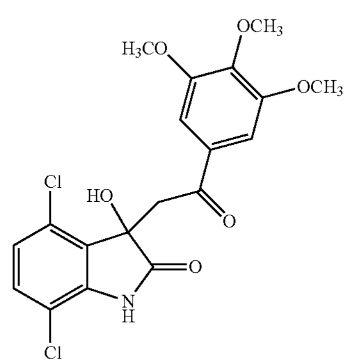 [SMILES: COc1cc(C(=O)CC2(O)C(=O)Nc3c(Cl)ccc(Cl)c32)cc(OC)c1OC] | 40 | 40 | 40 |
| PT-1-16 | 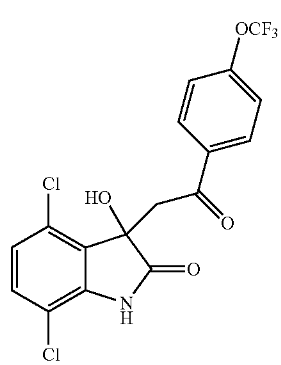 [SMILES: O=C(CC1(O)C(=O)Nc2c(Cl)ccc(Cl)c21)c1ccc(OC(F)(F)F)cc1] | 40 | 40 | 40 |

TABLE 2-continued

| Example | Structure | IC$_{50}$ (μM) | | |
| --- | --- | --- | --- | --- |
| | | PANC 1 | TC32 | TC71 |
| PT-1-20 | 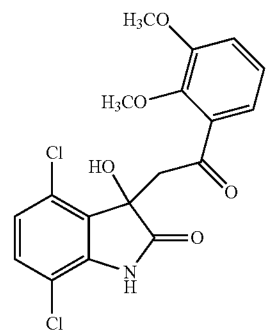 [SMILES: COc1cccc(C(=O)CC2(O)C(=O)Nc3c(Cl)ccc(Cl)c32)c1OC] | 40 | 40 | 40 |
| PT-1-21 | 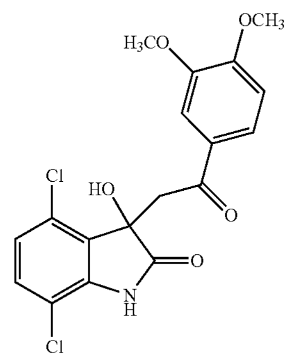 [SMILES: COc1ccc(C(=O)CC2(O)C(=O)Nc3c(Cl)ccc(Cl)c32)cc1OC] | 40 | 40 | 40 |
| PT-1-33 | 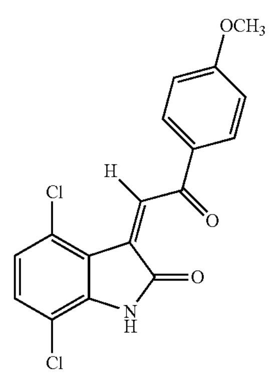 [SMILES: COc1ccc(C(=O)/C=C2\C(=O)Nc3c(Cl)ccc(Cl)c32)cc1] | 40 | 1.035 | 1.636 |
| PT-2-37 | 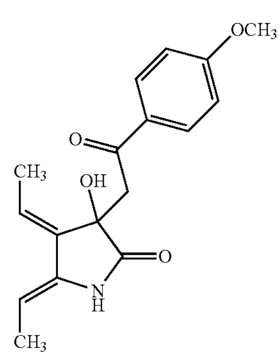 [SMILES: C/C=C1\NC(=O)C(O)(CC(=O)c2ccc(OC)cc2)\C1=C/C] | 40 | 40 | 40 |

TABLE 2-continued

| Example | Structure | IC$_{50}$ (μM) | | |
|---|---|---|---|---|
| | | PANC 1 | TC32 | TC71 |
| PT-2-78 | 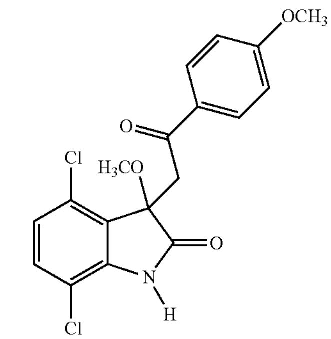 [SMILES: COc1ccc(C(=O)CC2(OC)C(=O)Nc3c(Cl)ccc(Cl)c32)cc1] | 40 | 40 | 40 |
| PT-2-79 | 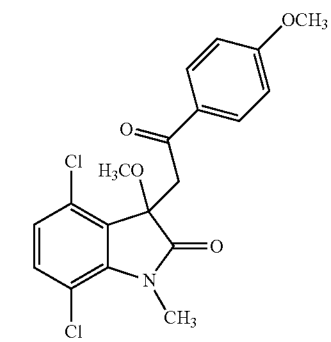 [SMILES: COc1ccc(C(=O)CC2(OC)C(=O)N(C)c3c(Cl)ccc(Cl)c32)cc1] | 11.19 | 12.13 | 16.98 |
| PT-2-47 | 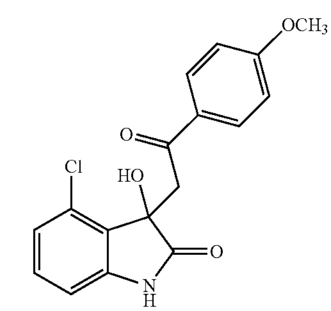 [SMILES: COc1ccc(C(=O)CC2(O)C(=O)Nc3cccc(Cl)c32)cc1] | | | |
| PT-2-39 | 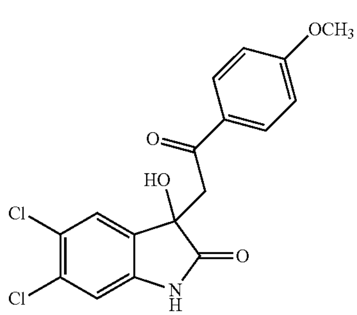 [SMILES: COc1ccc(C(=O)CC2(O)C(=O)Nc3cc(Cl)c(Cl)cc32)cc1] | | | |

TABLE 2-continued
| Example | Structure | IC$_{50}$ (µM) | | |
| --- | --- | --- | --- | --- |
| | | PANC 1 | TC32 | TC71 |
| PT-2-99 | 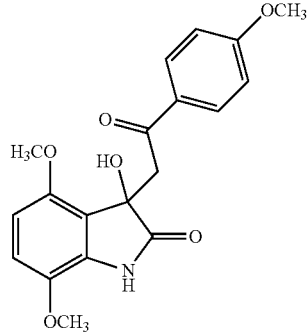 [SMILES: COc1ccc(C(=O)CC2(O)C(=O)Nc3c(OC)ccc(OC)c32)cc1] | | | |
| PT-2-94 | 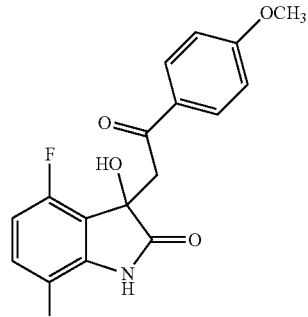 | | | |
| PT-2-84 | 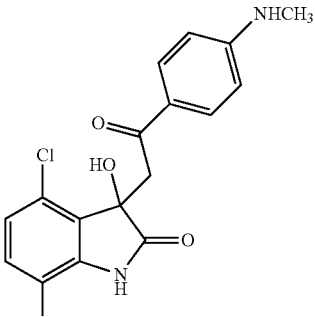 | | | |
| PT-2-89 | 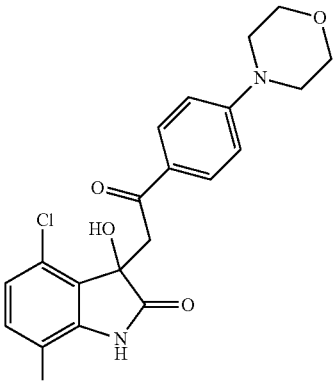 | | | |

Example 6

Growth Inhibition of EWS-FLI1 Cells with Substituted Analogs

Figure 3A:
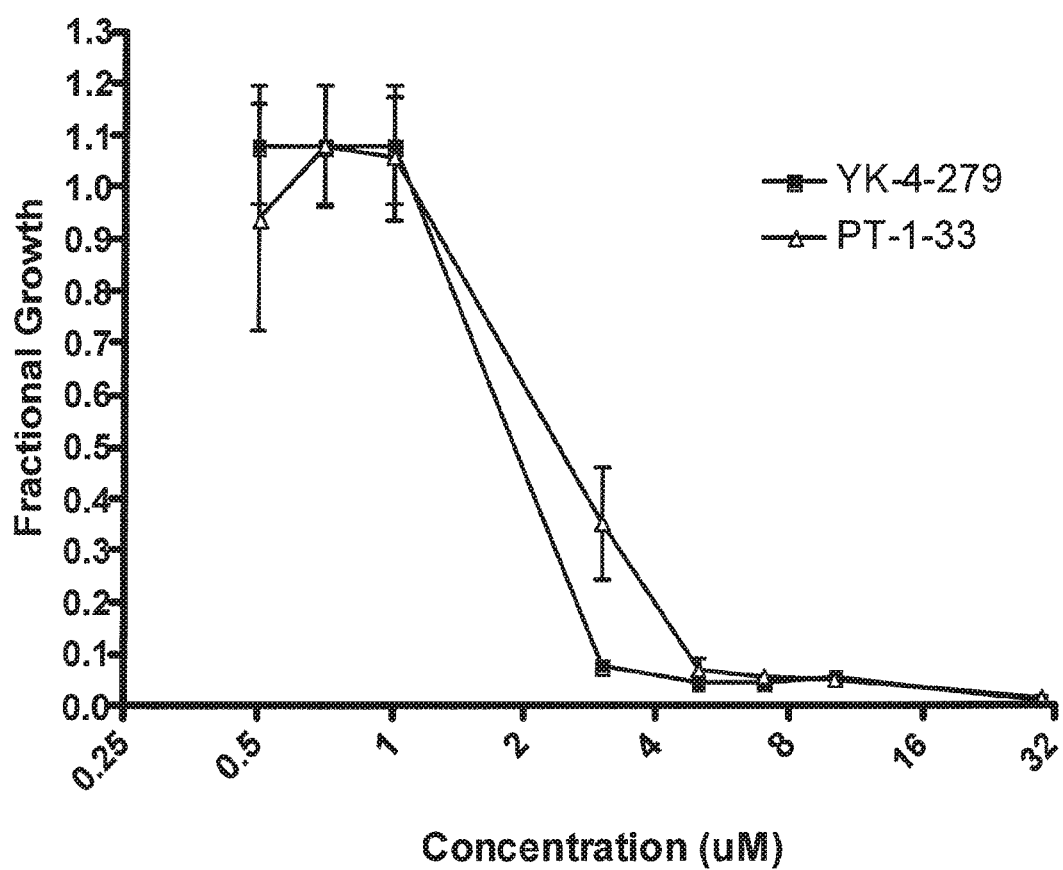
FIG. 3A is a graph of the growth inhibition of TC71 and TC32 cells for various concentrations of YK-4-279 and PT-1-33.
Figure 3B:
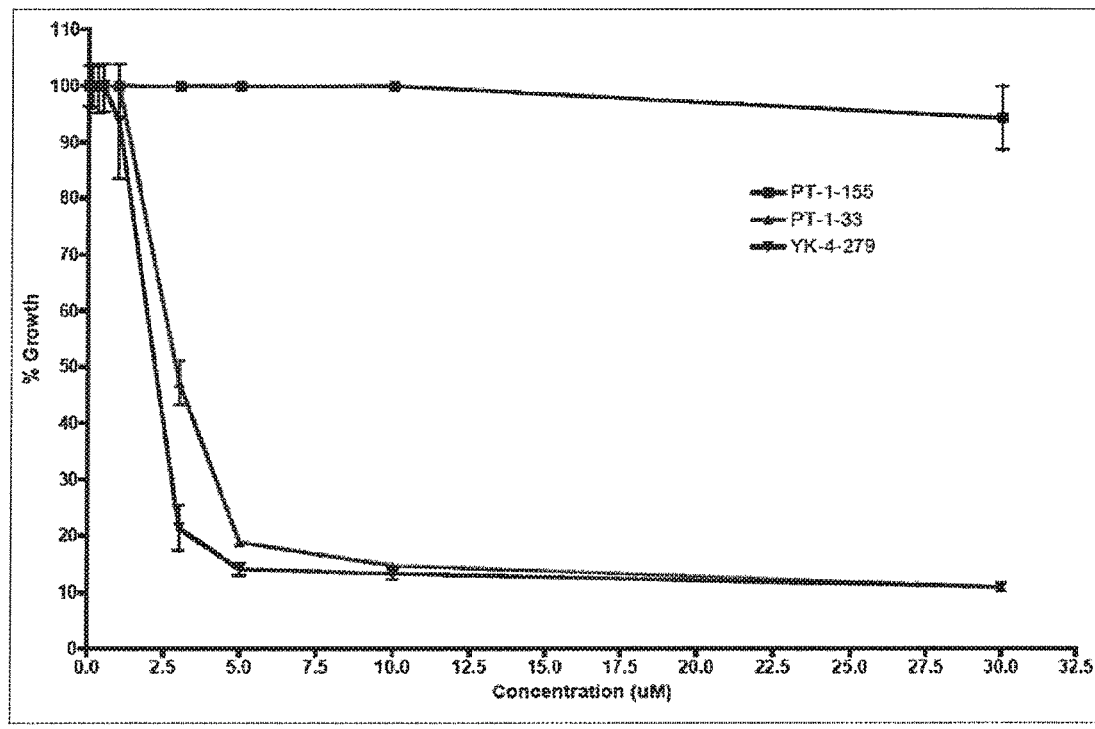
FIG. 3B is a graph of the growth inhibition of TC71 cells for various concentrations of YK-4-279, PT-1-33, and PT-1-55.
Figure 3C:
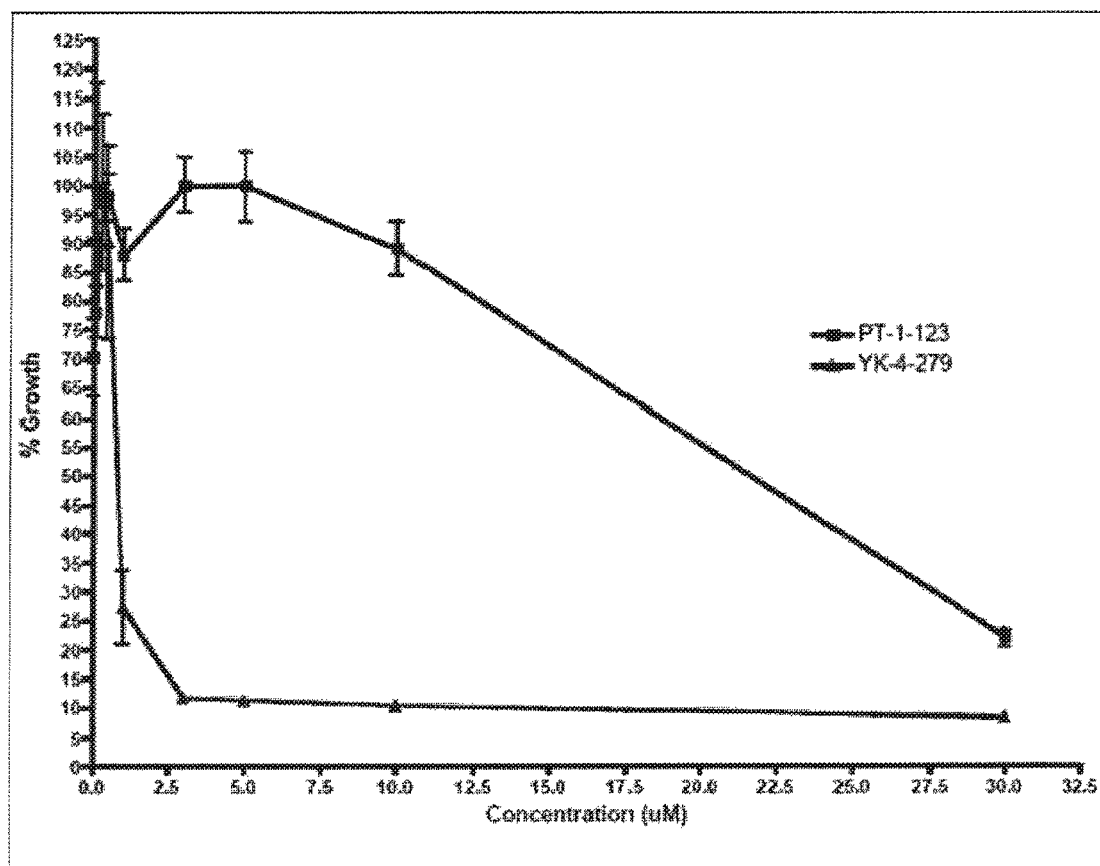
FIG. 3C is a graph of the growth inhibition of TC71 cells for various concentrations of YK-4-279 and PT-1-123.

The effects of the YK-4-279 analogs on the ESFT cells were tested by determining their growth inhibition. The IC50 of the lead compound was 900 nM for cells growing in monolayer. Growth inhibition of ESFT cells was measured for various concentrations of particular compounds. Growth inhibition of TC71 and TC32 cells was measured for various concentrations of YK-4-279 and PT-1-33 (FIG. 3A). Growth inhibition of TC71 cells was measured for various concentrations of YK-4-279, PT-1-33, and PT-1-55 (FIG. 3B). Growth inhibition of TC71 cells was measured for various concentrations of YK-4-279 and PT-1-123 (FIG. 3C). Some of the analogs had similar activity to YK-4-279. The dehydrated analogs and the alcohol analogs showed a similar activity against ESFT cells (FIG. 3A). Modifications of the ketone did not improve the activity of compounds (FIG. 3B and FIG. 3C).

Example 7

Apoptosis of EWS-FLI1 Cells

Figure 4:
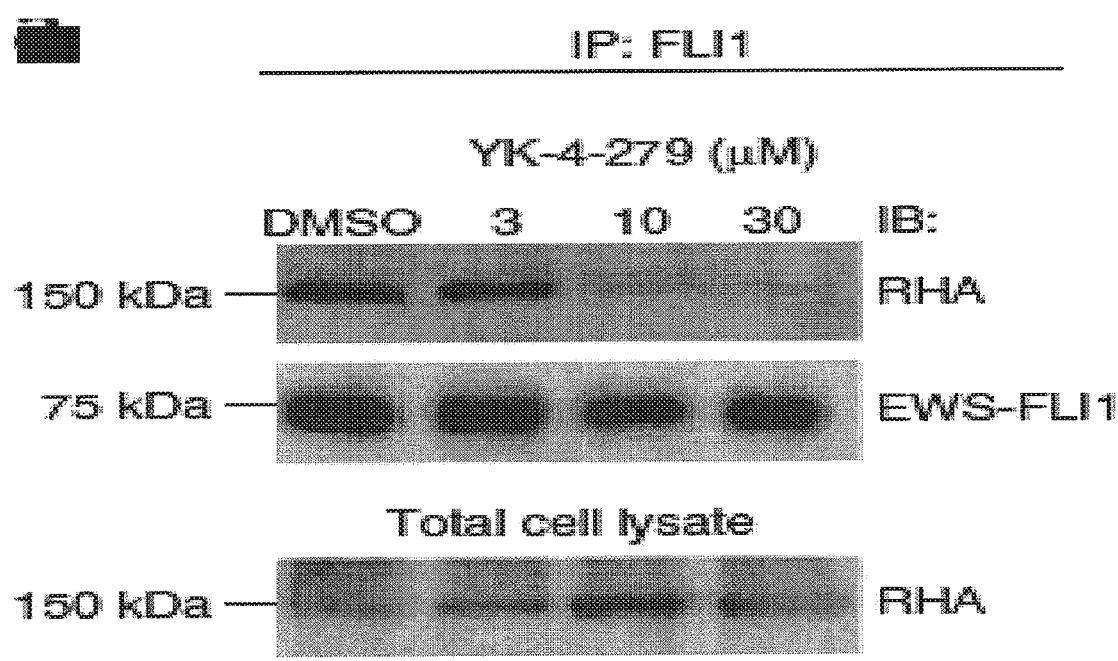
FIG. 4 is a photomicrograph of an immunoblot of protein lysates from TC32 cells treated with YK-4-279 and co-precipitated with RHA, EWS-FLI1 or total protein.

Immunoblots were prepared from protein lysates from TC32 cells treated with YK-4-279 and co-precipitated with RHA, EWS-FLI1 or total protein (FIG. 4). YK-4-279 did not directly affect the level of EWS-FLI1 or RHA but did disrupt their interactions. The disruption of the interaction of RHA with EWS-FLI1 presents an avenue for the development of a class of small molecules as potential therapeutics against the Ewing's family sarcoma tumors. While YK-4-279 disrupted the protein-protein interaction, PT-1-17 appeared to be more potent in the TC71 cells. Dehydrated analogs of YK-4-279 did not significantly increase the potency of the compounds.

Example 8

Disruption of EWS-FLI1/RHA Binding

The activity of candidate small molecules to disrupt binding between EWS-FLI1 and the His-tagged RHA protein, His-Tag RHA (647-1075), was screened in an ELISA assay. Briefly, candidate agents were incubated with RHA on plates coated with EWS-FLI1. After washing the plates, the amount of RHA that remained bound to the plates was determined using a primary anti-RHA antibody, and a secondary signal antibody.

Figure 5A:
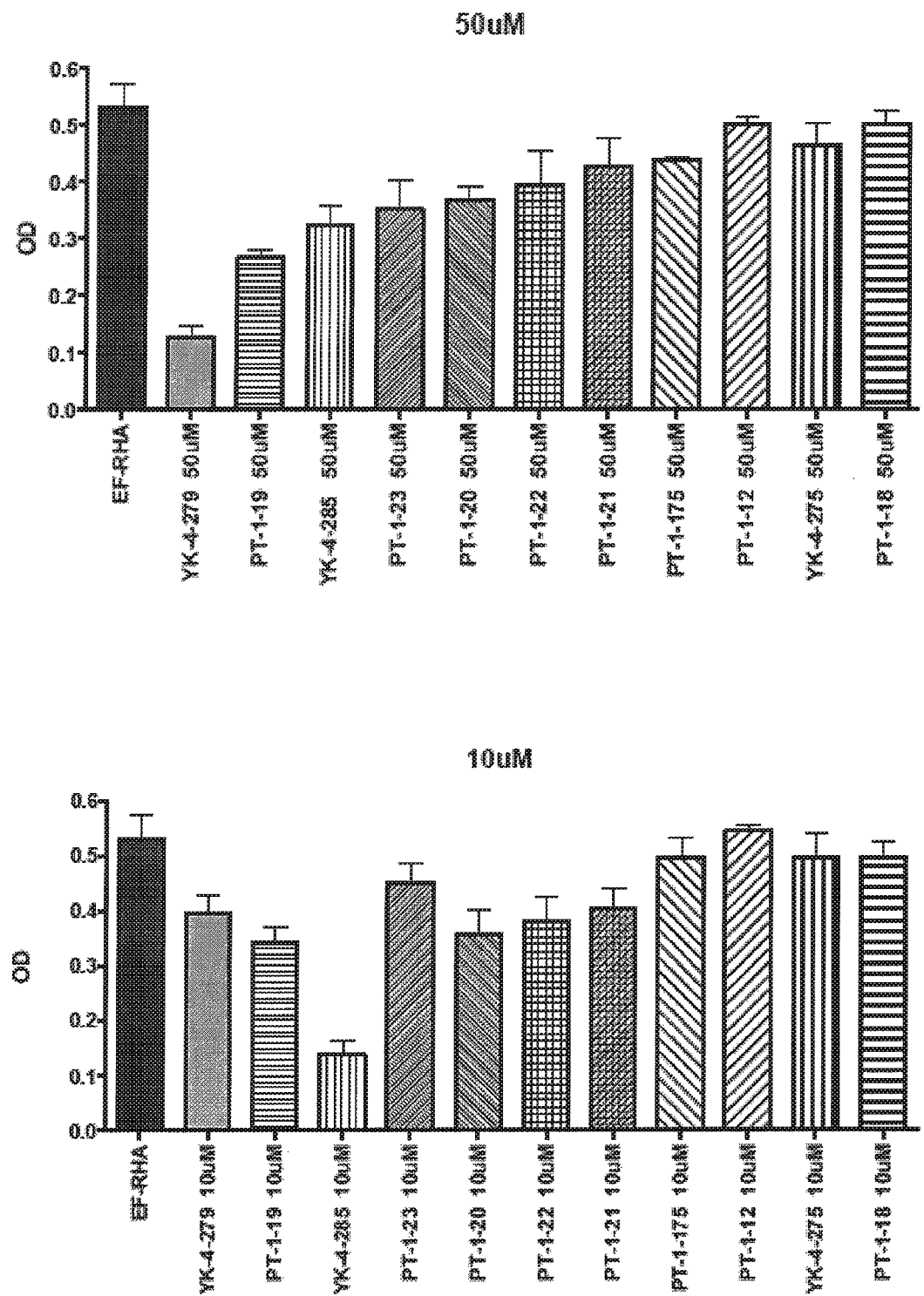
FIGS. 5A-5G are graphs of the relative optical density in ELISA assays measuring inhibition of EWS-FLI1 binding to RHA by various candidate agents.
Figure 5B:
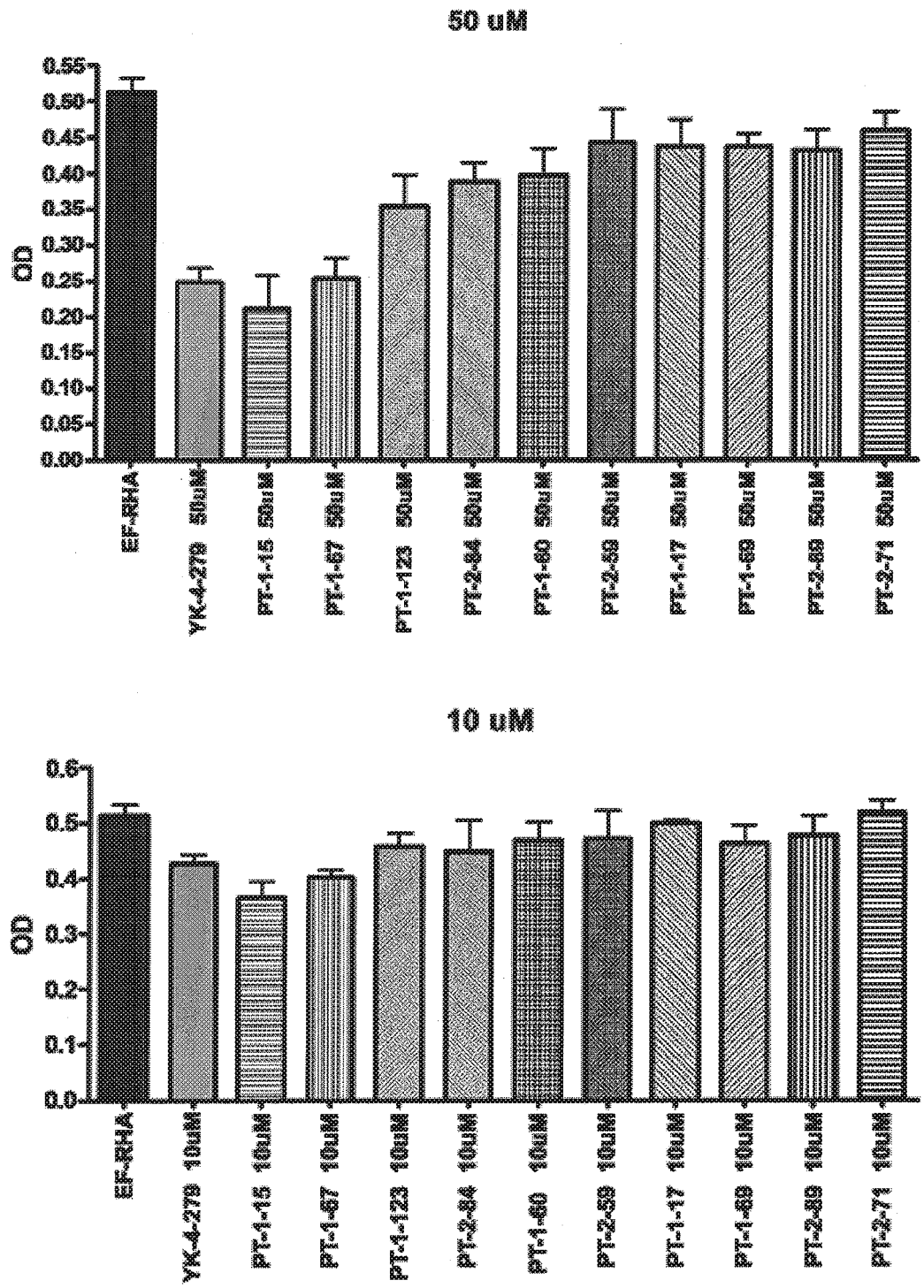
Figure 5C:
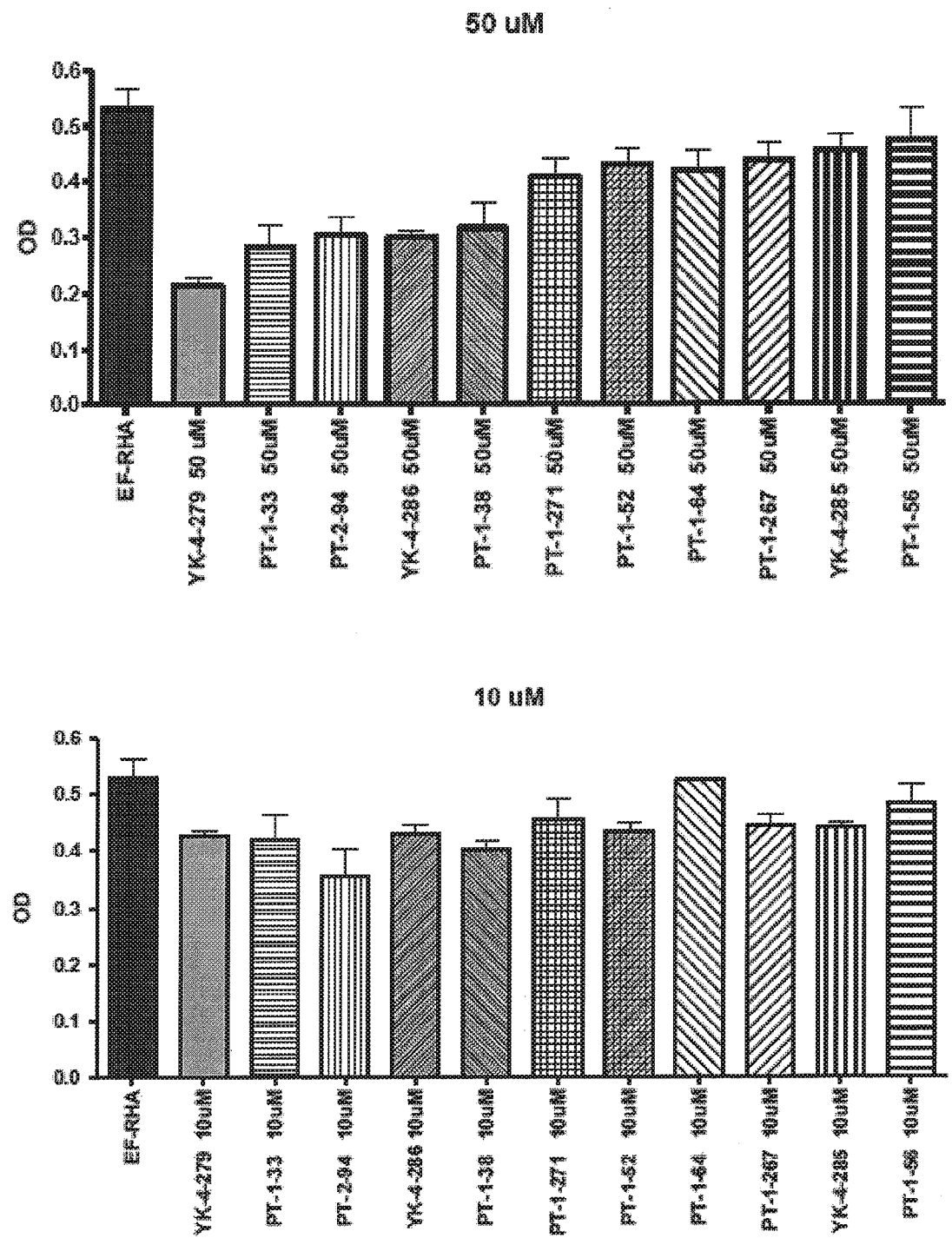
Figure 5D:
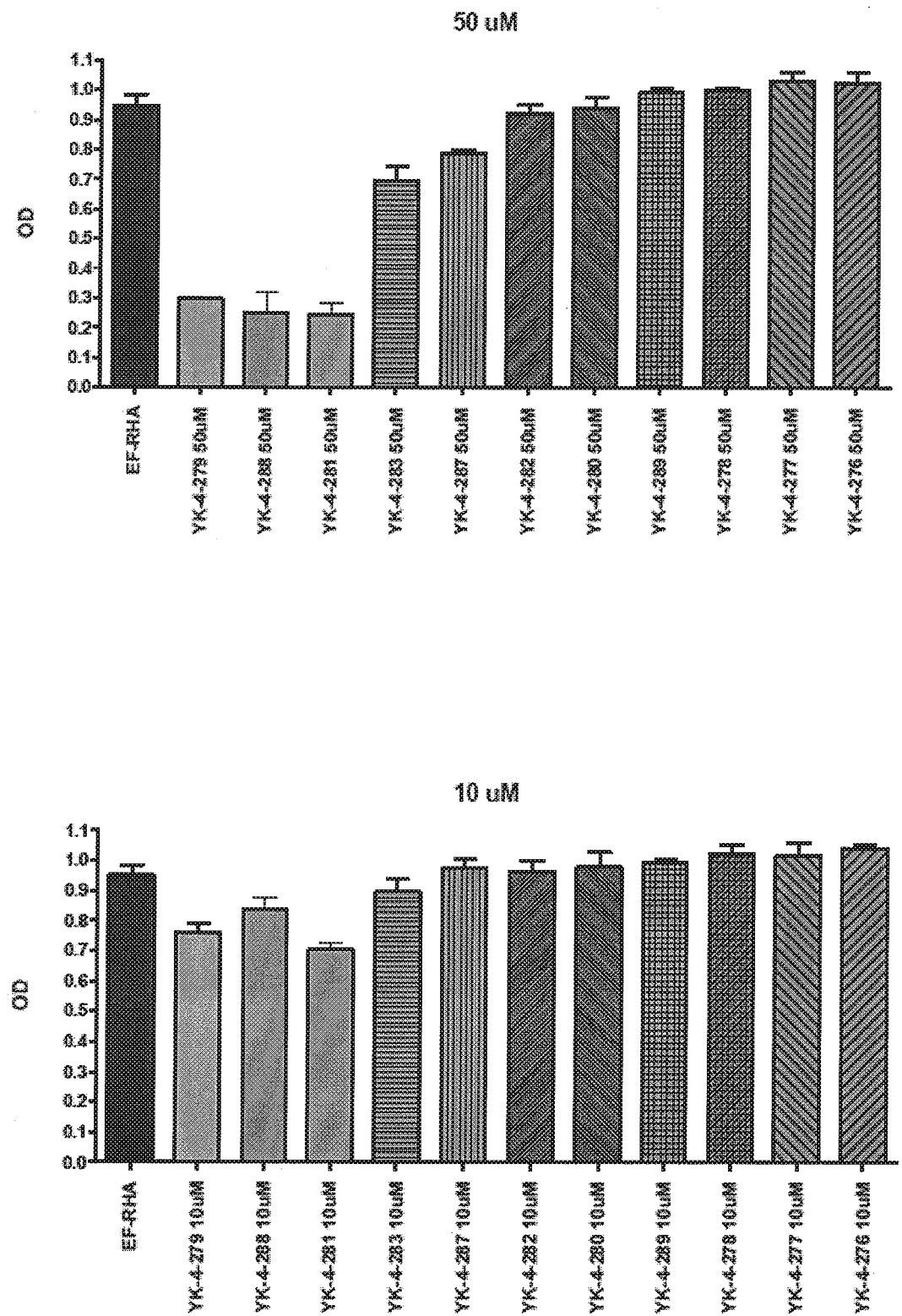
Figure 5E:
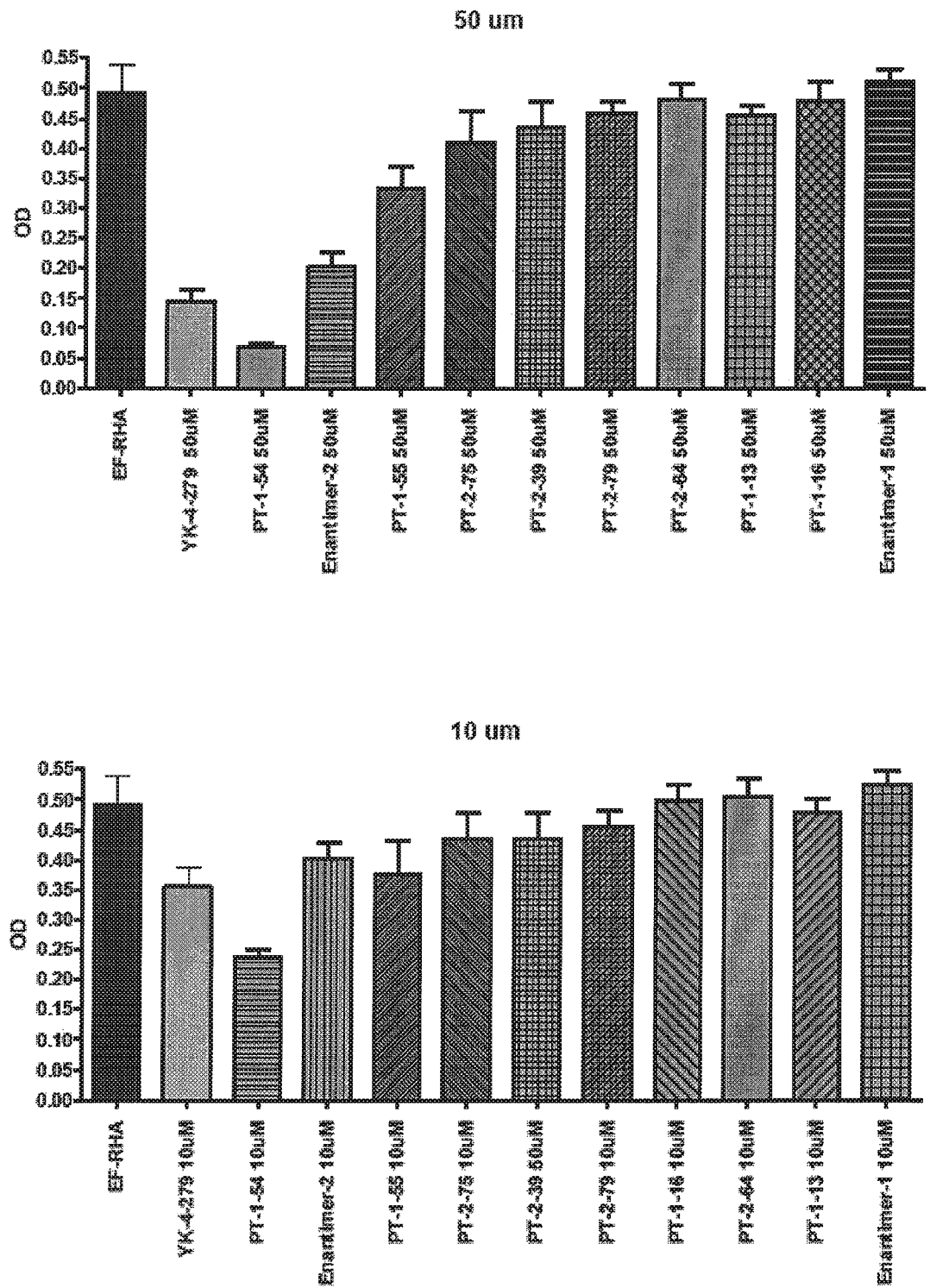
Figure 5F:
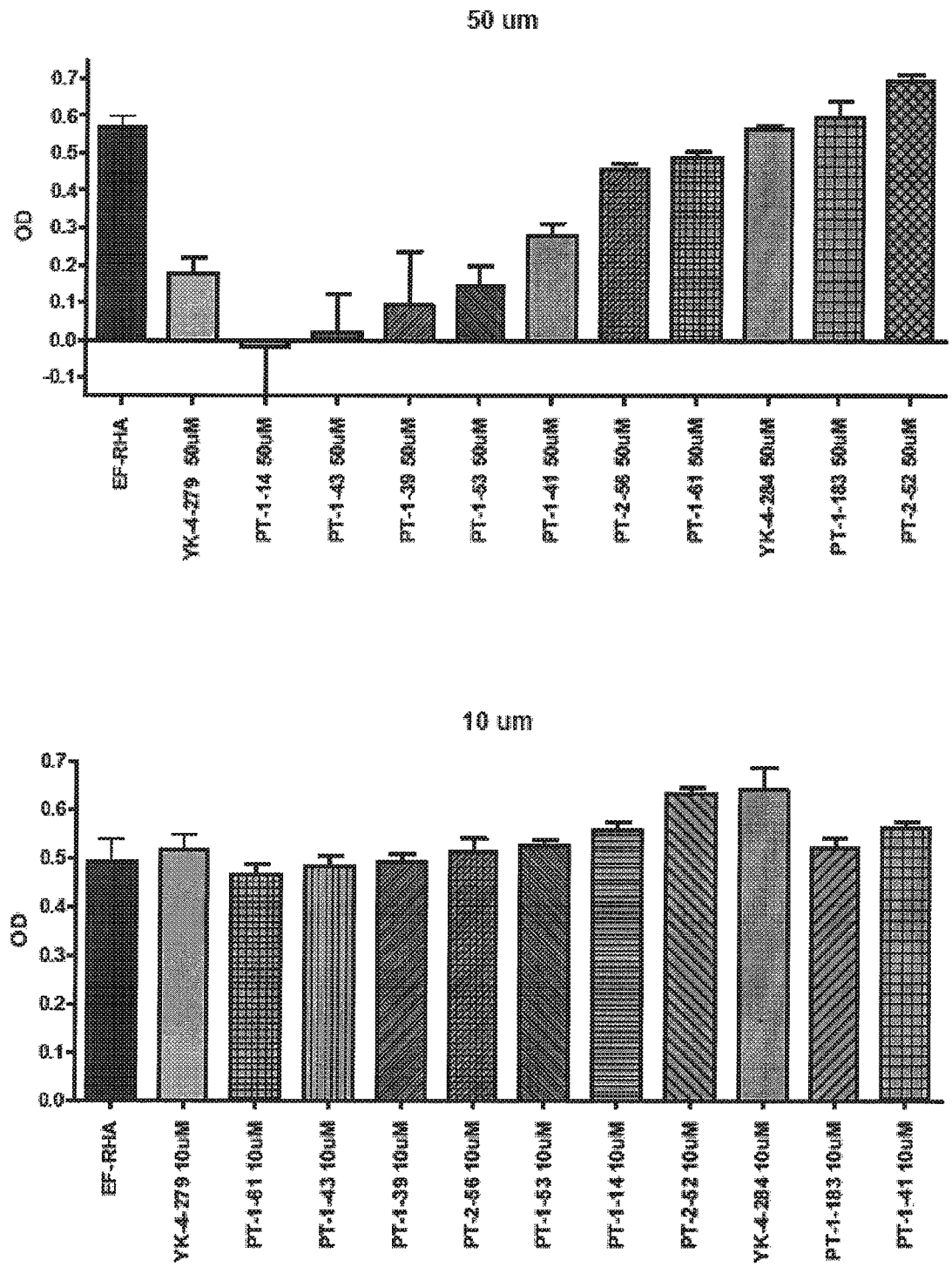
Figure 5G:
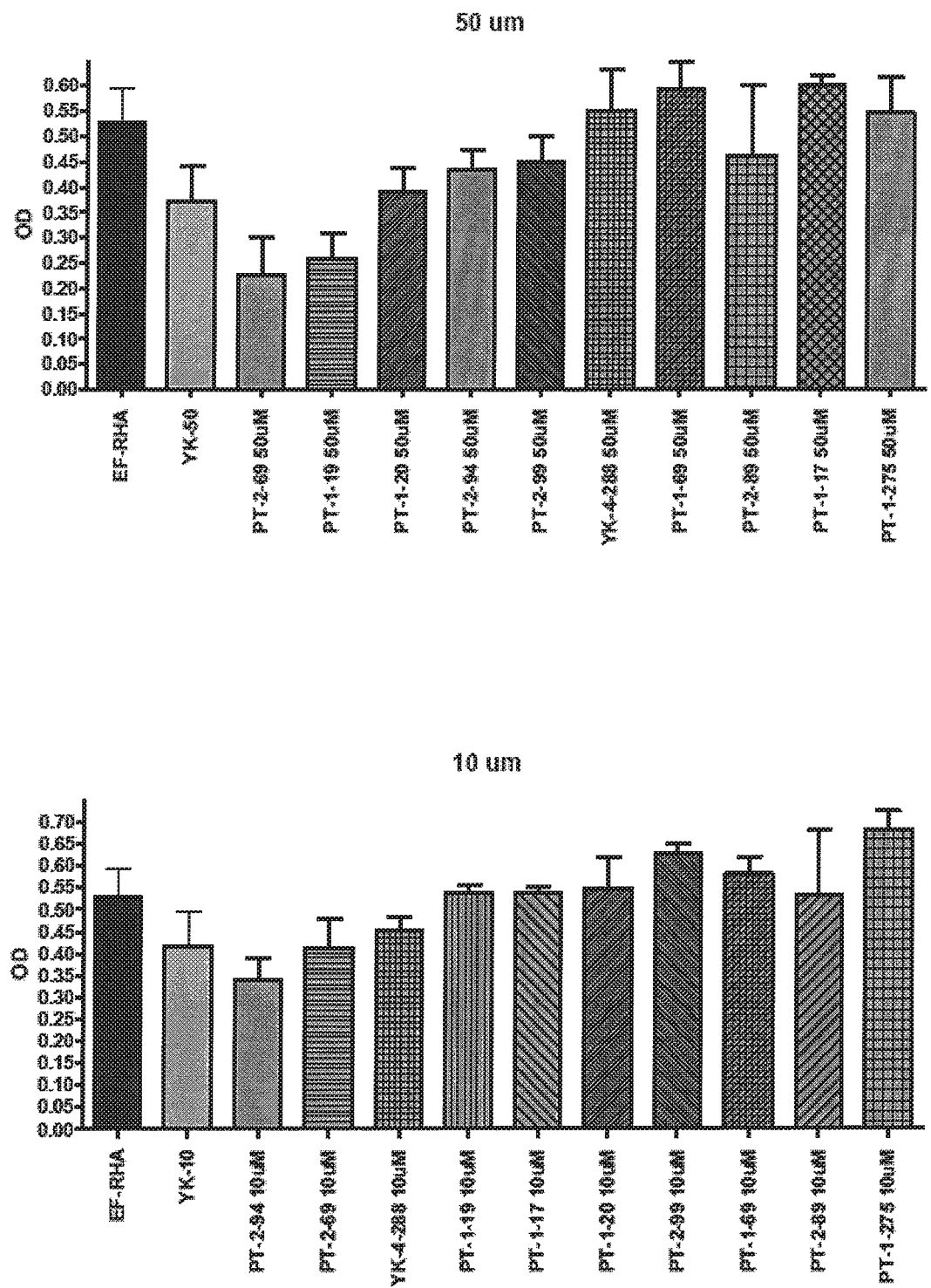

Wells in a 96-well plate were incubated with 100 µl/well 20 nM EWS-FLI1 protein solution (1M imidazole, 20 mM Tris, 500 mM NaCl) overnight at 4° C. Plates were washed with PBS, blocked with 150 µl/well 4% BSA for at least 2 h at room temperature, and then washed again with ELISA wash solution (PBS+0.1% T20, 200 µl/well). Plates were incubated for 1 hour at room temperature with 100 µl/well candidate agent in PBS (10 µM or 50 µM final), or DMSO control. Plates were incubated overnight at 4° C. with 100 µl/well 20 nM His-RHA protein solution (0.5 M imidazole, 125 mM NaCl, 20 mM Tris), and then washed with ELISA wash solution (PBS+0.1% T20, 200 µl/well). RHA bound to the plates was detected by incubating plates for 1 hour at room temperature with 100 µl/well primary anti-RHA antibody (1:1000 goat Anti-DHX9/EB09297, Everest), and then washing with ELISA wash solution (PBS+0.1% T20, 200 µl/well). Primary antibody was detected by incubating plates for 1 hour at room temperature with 100 µl/well secondary anti-goat antibody (1:500 donkey anti-goat IgG-HRP: sc-2020), and then washing with ELISA wash solution (PBS+0.1% T20, 200 µl/well). A horseradish peroxidase assay kit was used to determine the amount of secondary anti-goat antibody in each well (Bio-Rad-TMB Peroxidase EIA Substrate Kit #172-1066), with plates read at 450 nm. A relatively lower optical density indicating lower amounts of HRP indicate a candidate agent with increased inhibitory activity for EWS-FLI1-RHA binding. The results are summarized in FIGS. 5A-5G. FIG. 5A summarizes results for the following candidate molecules: YK-4-275, YK-4-285, PT-1-12, PT-1-18, PT-1-19, PT-1-20, PT-1-21, PT-1-22, PT-1-23, PT-1-175. FIG. 5B summarizes results for the following candidate molecules: PT-2-84, PT-2-59, PT-1-17, PT-2-71, PT-2-89, PT-1-123, PT-1-15, PT-1-60, PT-1-67, PT-1-69. FIG. 5C summarizes results for the following candidate molecules: YK-4-285, YK-4-286, PT-1-33, PT-1-38, PT-1-271, PT-1-52, PT-1-56, PT-1-64, PT-2-94, PT-1-267). FIG. 5D summarizes results for the following candidate molecules: YK-4-282, YK-4-287, YK-4-2 80, YK-4-289, YK-4-288, YK-4-278, YK-4-276, YK-4-283, YK-4-277, YK-4-281 FIG. 5E summarizes results for the following candidate molecules: PT-1-54, YK-4-279 (S), YK-4-279 (R), PT-1-55, PT-2-75, PT-2-39, PT-2-79, PT-1-16, PT-1-13, PT-2-64. FIG. 5F summarizes results for the following candidate molecules: YK-4-284, PT-1-14, PT-1-39, PT-1-41, PT-1-43, PT-1-53, PT-2-56, PT-2-52, PT-1-61, PT-1-183. FIG. 5G summarizes results for the following candidate molecules: PT-1-275, PT-2-69, PT-2-99, YK-4-288, PT-1-19, PT-1-20, PT-1-69, PT-2-89, PT-1-17, PT-2-94.

Example 9

Disruption of EWS-FLI1 Transcription Factor Activity

Figure 6A:
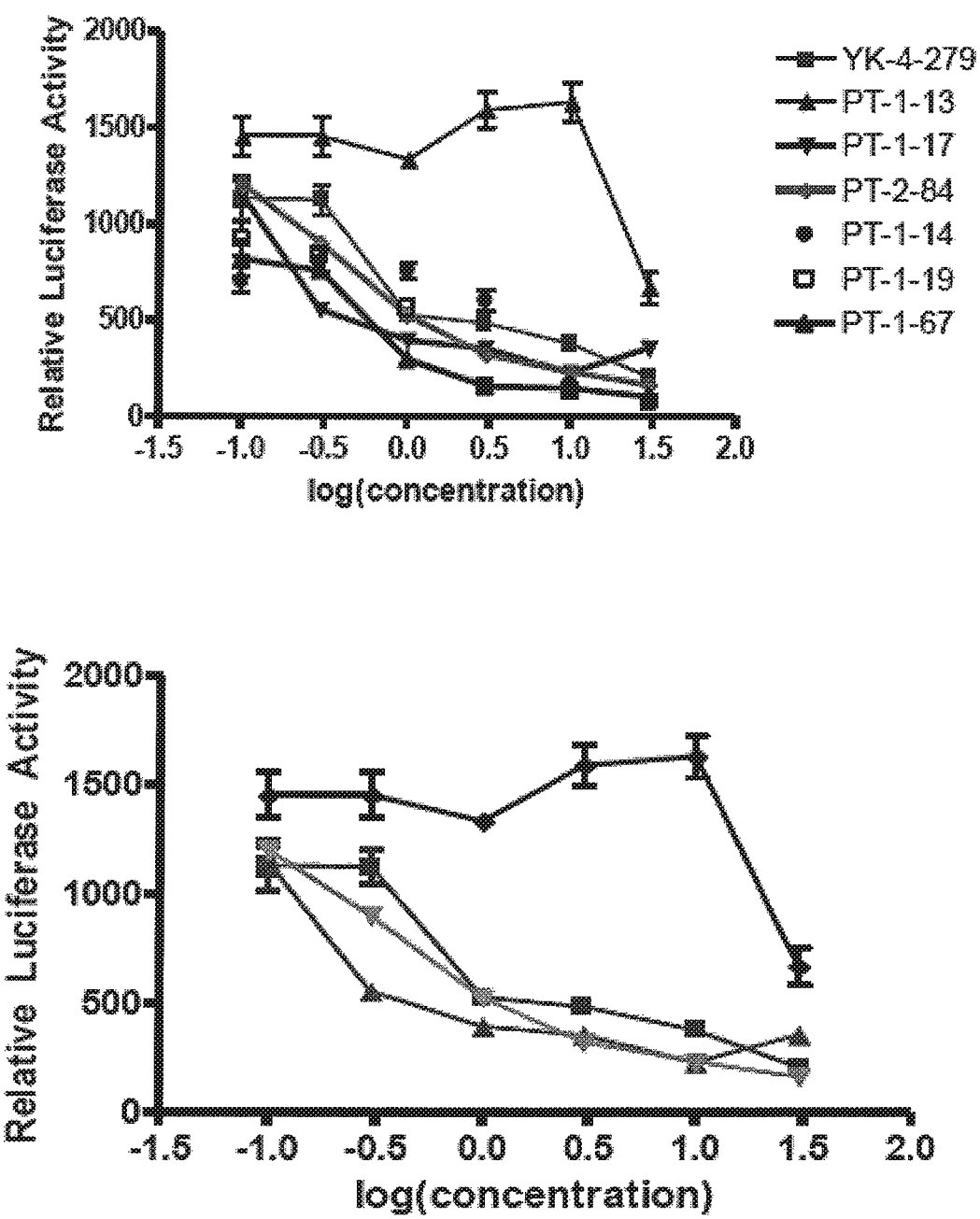
FIG. 6A and FIG. 6B are graphs showing general trends for relative luciferase activity for various concentrations of candidate agents in luciferase assays measuring inhibition of EWS-FLI1 binding to the NROB1 promoter.
Figure 6B:
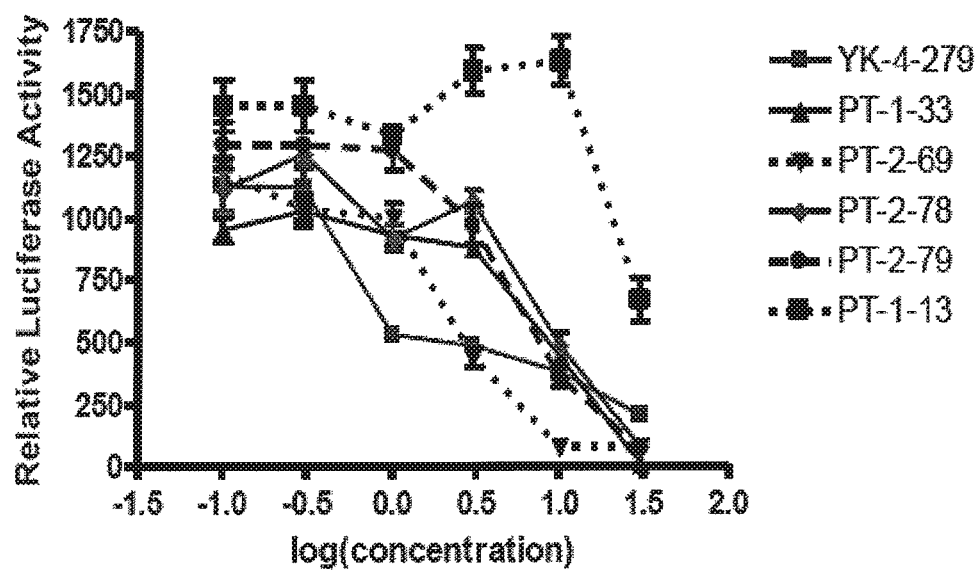
Figure 6B:
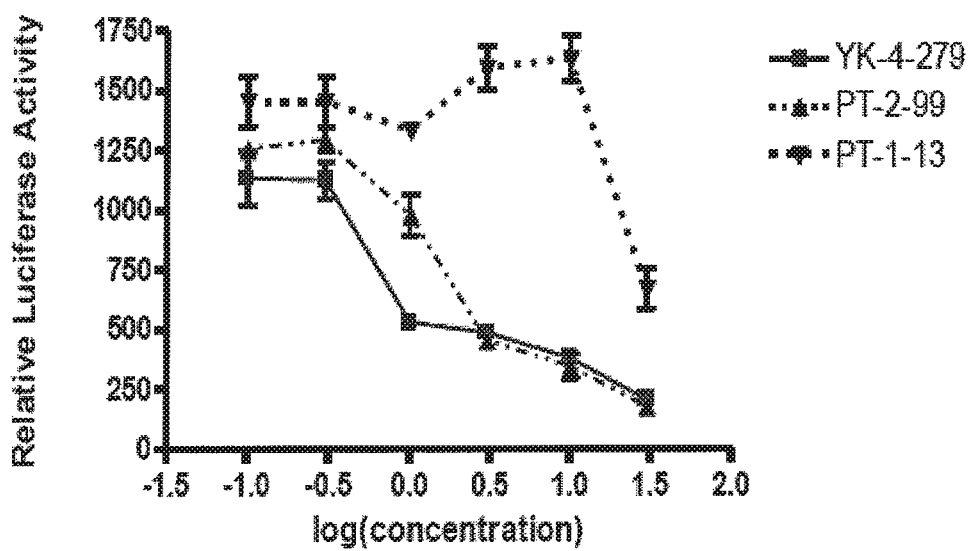
Figure 7A:
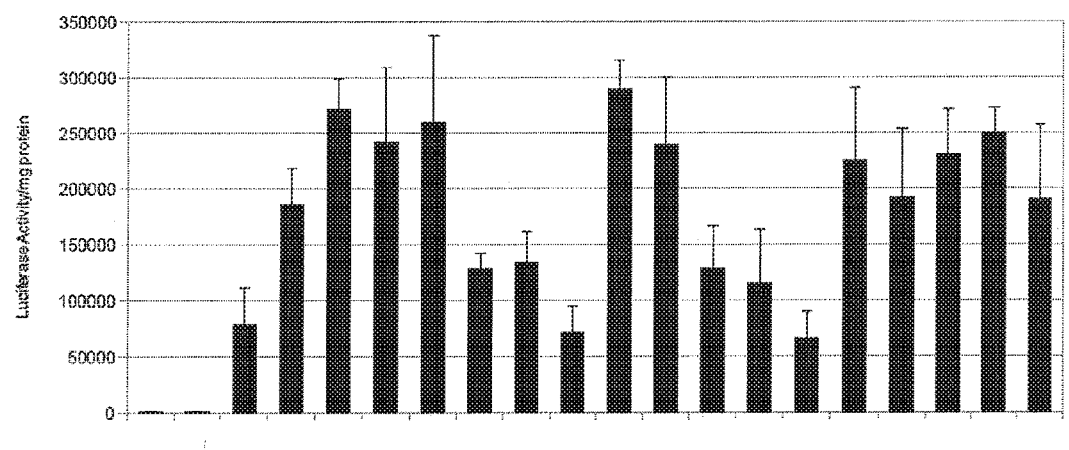
FIG. 7A-FIG. 7I illustrate luciferase activity for various concentrations of candidate agents in luciferase assays measuring inhibition of EWS-FLI1 binding to the NROB 1 promoter.
Figure 7B:
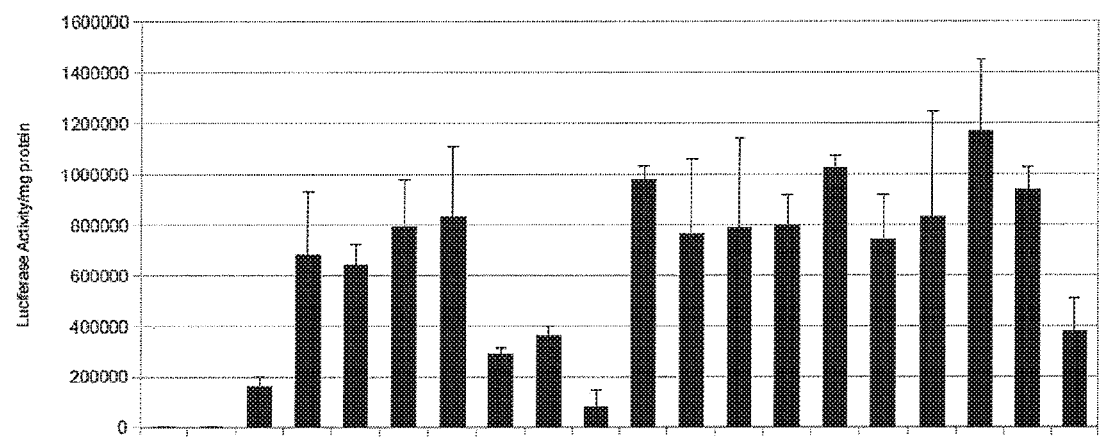
Figure 7C:
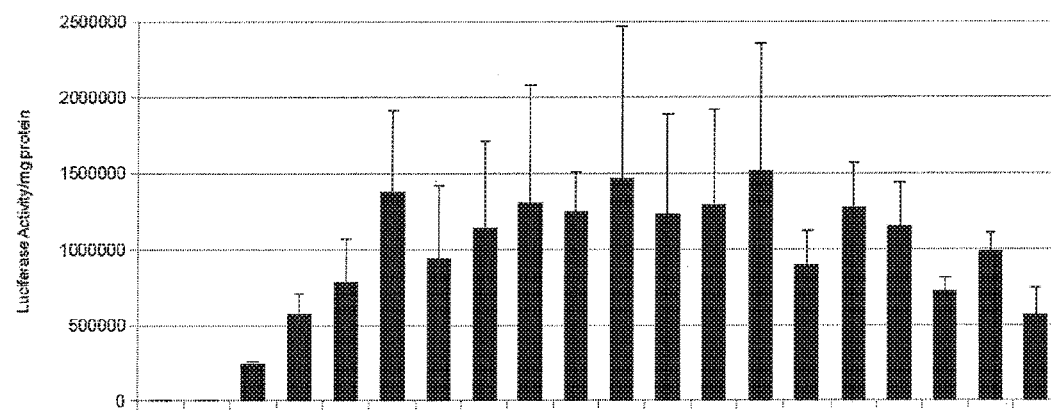
Figure 7D:
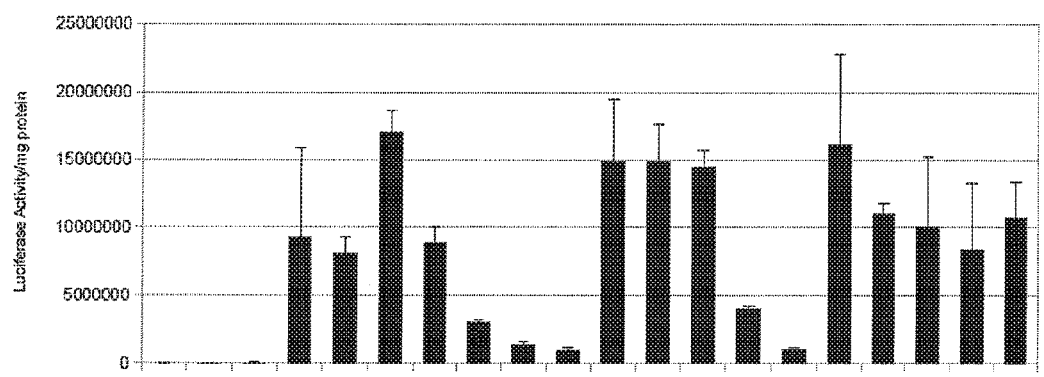
Figure 7E:
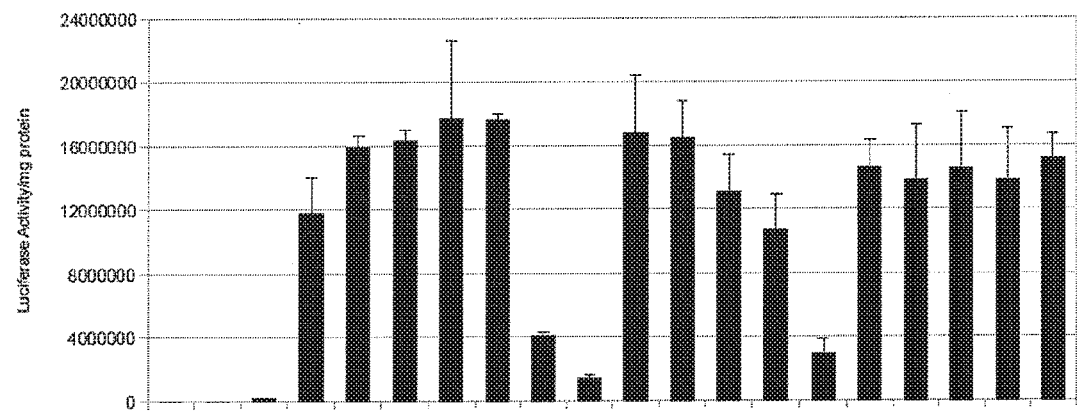
Figure 7F:
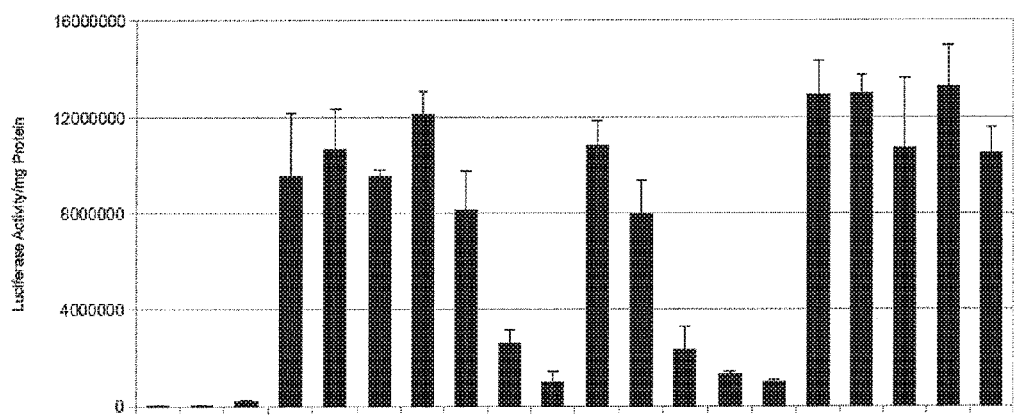
Figure 7G:
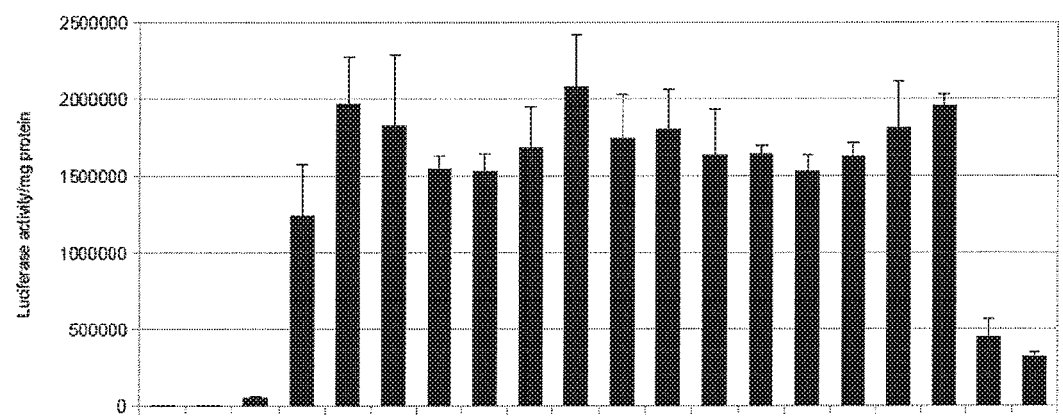
Figure 7H:
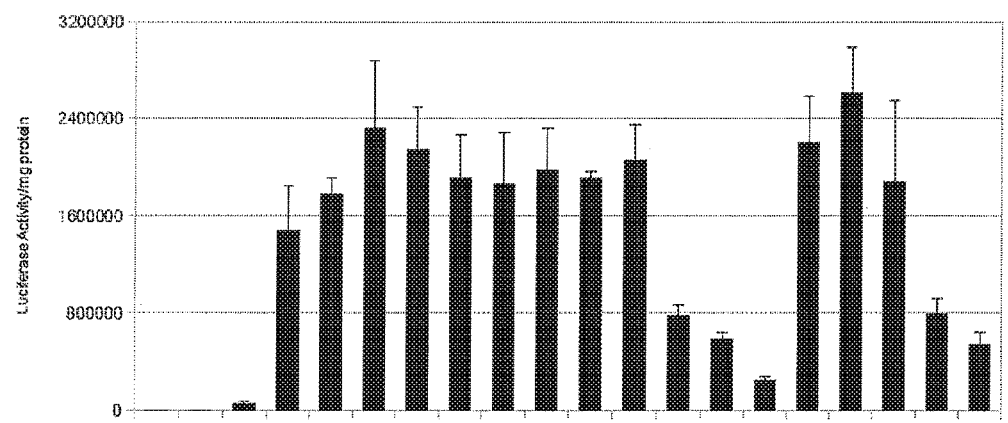
Figure 7I:
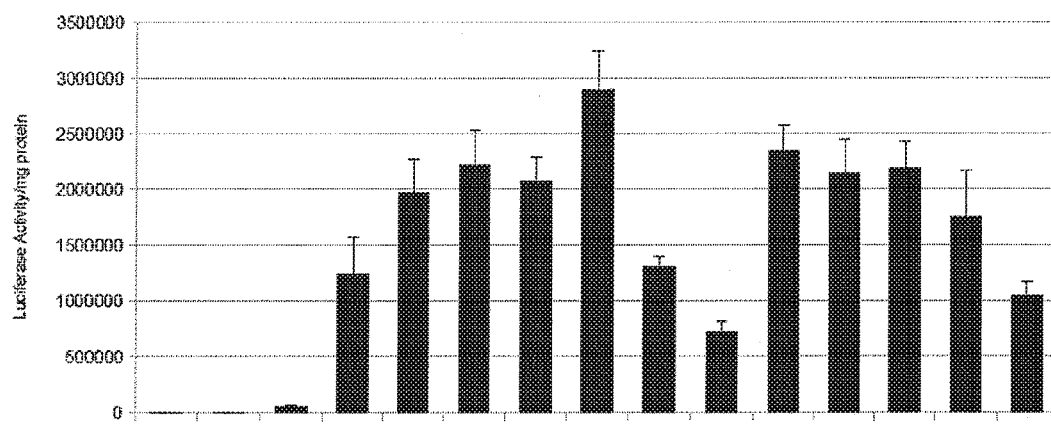

The activity of candidate small molecules to disrupt EWS-FLI1 transcription factor activity was screened using a luciferase assay in which EWS-FLI1 binding to the NROB 1 promoter increases luciferase expression. Briefly, cells were transfected with a vector containing the NROB1 promoter driving luciferase expression, and an EWS-FLI1 expression vector. Transfected cells were treated with various concentrations of a candidate agent, and any change in the relative level of luciferase expression was determined. COST cells were plated in 96-well plates and transfected with pciNEO/EF vector and pGL3-NROB1. Controls included transfections with each vector only. Transfected cells were treated with various concentrations of a candidate agent, and treated cells were assays for luciferase activity. Decreased luciferase activity indicates a candidate agent with inhibitory activity in EWS-FLI1 acting as a transcription factor, promoting transcription of luciferase. FIG. 6A and FIG. 6B show general trends for relative luciferase activity for various concentrations of candidate agents. FIGS. 7A-7I show inhibitory activity for various concentrations of candidate agents.

Example 10

Treating Glioblastoma Multiforme

Glioblastoma multiforme (GBM) is a very well annotated tumor from the perspective of its genetics that have led to molecular segregation into classic, proneural, neural, and mesenchymal categories (Purow B W, Schiff D. Glioblastoma genetics: in rapid flux. Discov Med. 2010 February; 9(45):125-31. PubMed PMID: 20193638. Pubmed Central PMCID: 3365574). The genetic alterations that categorize GBM include constitutive activation of signaling pathways, loss of tumor suppressors, mutations in metabolic pathways, abnormal DNA repair, and loss of mitotic regulators (Suzuki E, Williams S, Sato S, Gilkeson G, Watson D K, Zhang X K. The transcription factor Fli-1 regulates monocyte, macrophage and dendritic cell development in mice. Immunology. 2013 July; 139(3):318-27. PubMed PMID: 23320737. Pubmed Central PMCID: 3701178; Chow L M, Endersby R, Zhu X, Rankin S, Qu C, Zhang J, et al. Cooperativity within and among Pten, p53, and Rb pathways induces high-grade astrocytoma in adult brain. Cancer Cell. 2011 Mar. 8; 19(3):305-16. PubMed PMID: 21397855. Pubmed Central PMCID: 3060664; Solomon D A, Kim T, Diaz-Martinez L A, Fair J, Elkahloun A G, Harris B T, et al. Mutational inactivation of STAG2 causes aneuploidy in human cancer. Science. 2011 Aug. 19; 333(6045):1039-43. PubMed PMID: 21852505. Epub 2011/Aug./20. eng). Even within these categories, GBM is recognized as a tumor with significant intratumoral heterogeneity (Garraway L A, Lander E S. Lessons from the cancer genome. Cell. 2013 Mar. 28; 153(1):17-37. PubMed PMID: 23540688; Nabilsi N H, Deleyrolle L P, Darst R P, Riva A, Reynolds B A, Kladde M P. Multiplex mapping of chromatin accessibility and DNA methylation within targeted single molecules identifies epigenetic heterogeneity in neural stem cells and glioblastoma. Genome Res. 2013 Oct. 8. PubMed PMID: 24105770). Despite this extraordinary variability in genetics, little attention has been focused on transcriptional regulators. One reason transcription factors have been less well studied in GBM may be the absence of effective small molecule inhibitors. The exception to this is p53, whose wild-type function can be sustained with the small molecule protein interaction inhibitor Nutlin-3 (Vassilev L T. p53 Activation by small molecules: application in oncology. J Med Chem. 2005 Jul. 14; 48(14):4491-9. PubMed PMID: 15999986).

Despite the genetic diversity, many clinical trials have been completed that evaluate targeted and non-targeted therapeutics for GBM. Despite all of these trials, including radiation therapy and molecularly guided surgical resection, progress towards effective, long-term GBM therapy has been unsuccessful for the vast majority of patients (Yin A A, Cheng J X, Zhang X, Liu B L. The treatment of glioblastomas: A systematic update on clinical Phase III trials. Crit Rev Oncol Hematol. 2013 September; 87(3):265-82. PubMed PMID: 23453191). A most recent VEGFR small molecule inhibitor plus temozolomide phase III trial also showed no improvement over standard of care temozolomide plus radiation therapy (Batchelor T T, Mulholland P, Neyns B, Nabors L B, Campone M, Wick A, et al. Phase III Randomized Trial Comparing the Efficacy of Cediranib As Monotherapy, and in Combination With Lomustine, Versus Lomustine Alone in Patients With Recurrent Glioblastoma. J Clin Oncol. 2013 Sep. 10; 31(26):3212-8. PubMed PMID: 23940216). A significant challenge to any GBM therapy is overcoming the blood-brain barrier (BBB), and this has impacted many potential targeted therapies (Juratli T A, Schackert G, Krex D. Current status of local therapy in malignant gliomas—a clinical review of three selected approaches. Pharmacol Ther. 2013 September; 139(3):341-58. PubMed PMID: 23694764).

The use of microRNA (miRNA) both to understand the biology of GBM and develop novel therapies led to a novel discovery that diacylglycerol kinase alpha may be a potential target, and small molecule optimizations are currently underway for these inhibitors (Dominguez C L, Floyd D H, Xiao A, Mullins G R, Kefas B A, Xin W, et al. Diacylglycerol kinase alpha is a critical signaling node and novel therapeutic target in glioblastoma and other cancers. Cancer Discov. 2013 July; 3(7):782-97. PubMed PMID: 23558954. Pubmed Central PMCID: 3710531). In addition, the miRNA have been used to create bioinformatics models that do suggest a network of transcriptional regulation is clearly important for GBM oncogenesis (Sun J, Gong X, Purow B, Zhao Z. Uncovering MicroRNA and Transcription Factor Mediated Regulatory Networks in Glioblastoma. PLoS computational biology. 2012; 8(7):e1002488. PubMed PMID: 22829753. Pubmed Central PMCID: 3400583).

Friend Leukemia Insertion-1 (FLI1) is a Putative Novel GBM Target.

Figure 8:
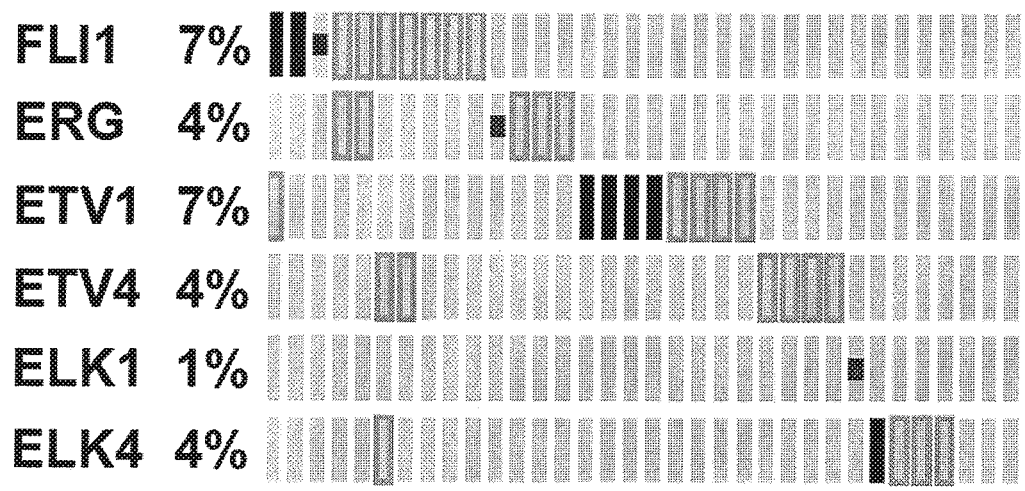
FIG. 8 depicts the cBioPortal for cancer genomics website interface.

Transcription factors are the focal driving oncogene in many cancers, yet have been considered 'undruggable' since they lack enzymatic activity. To date, despite the TCGA database for GBM, the therapeutic targeting of critical transcriptional nodes has not occurred. The ets family transcription factor FLI1 is expressed in GBM based upon querying the TCGA database (FIG. 8). Early ETS-1 studies correlated ETS-1 expression with malignant potential in human astrocytic tumors (Kitange G, Kishikawa M, Nakayama T, Naito S, Iseki M, Shibata S. Expression of the Ets-1 proto-oncogene correlates with malignant potential in human astrocytic tumors. Mod Pathol. 1999 June; 12(6): 618-26. PubMed PMID: 10392639). In addition, studies showed that ETS-1 may drive angiogenesis in astrocytic tumors (Valter M M, Hugel A, Huang H J, Cavenee W K, Wiestler O D, Pietsch T, et al. Expression of the Ets-1 transcription factor in human astrocytomas is associated with Fms-like tyrosine kinase-1 (Flt-1)/vascular endothelial growth factor receptor-1 synthesis and neoangiogenesis. Cancer Res. 1999 Nov. 1; 59(21):5608-14. PubMed PMID: 10554042). Many studies suggest a significant role for ets family ELK members in GBM transcription and overall biology (Day B W, Stringer B W, Spanevello M D, Charmsaz S, Jamieson P R, Ensbey K S, et al. ELK4 neutralization sensitizes glioblastoma to apoptosis through downregulation of the anti-apoptotic protein Mcl-1. Neuro Oncol. 2011 November; 13(11):1202-12. PubMed PMID: 21846680. Pubmed Central PMCID: 3199151; Shukla A A, Jain M, Chauhan SS. Ets-1/Elk-1 is a critical mediator of dipeptidylpeptidase III transcription in human glioblastoma cells. Febs J. 2010 April; 277(8):1861-75. PubMed PMID: 20236318; Uht R M, Amos S, Martin P M, Riggan A E, Hussaini I M. The protein kinase C-eta isoform induces proliferation in glioblastoma cell lines through an ERK/Elk-1 pathway. Oncogene. 2007 May 3; 26(20):2885-93. PubMed PMID: 17146445). While one immunohistochemical study did not find FLI1 expression in GBM, however, there are significant challenges in antibody selection and antigen retrieval that may have impacted on these negative results (Mhawech-Fauceglia P, Herrmann F R, Bshara W, Odunsi K, Terracciano L, Sauter G, et al. Friend leukaemia integration-1 expression in malignant and benign tumours: a multiple tumour tissue microarray analysis using polyclonal antibody. J Clin Pathol. 2007 June; 60(6):694-700. PubMed PMID: 16917000. Pubmed Central PMCID: 195505).

Using the cBioPortal for cancer genomics website interface, a subset of ets family members involved in cancer was evaluated. These alterations include amplifications (solid red bar), mutations (small green square), and mRNA upregulation (open red bars). See FIG. 8.

FLI1 targeting in GBM is further supported based upon its transcriptional activation of MDM2 (Truong A H, Cervi D, Lee J, Ben-David Y. Direct transcriptional regulation of MDM2 by Fli-1. Oncogene. 2005 Feb. 3; 24(6):962-9. PubMed PMID: 15592502). In this case, high MDM2 would cause degradation of p53, leading to loss of a key tumor suppressor protein. Of note, there is a loose correlation among the seven GBM cell lines between those with high FLI1 and high MDM2 (Table 3 and FIG. 10). In hematopoietic development, FLI1 is clearly an important protein, as noted by multiple immune defects when protein is eliminated by homologous recombination (Suzuki E, Williams S, Sato S, Gilkeson G, Watson D K, Zhang X K. The transcription factor Fli-1 regulates monocyte, macrophage and dendritic cell development in mice. Immunology. 2013 July; 139(3):318-27. PubMed PMID: 23320737. Pubmed Central PMCID: 3701178; Kruse E A, Loughran S J, Baldwin T M, Josefsson E C, Ellis S, Watson D K, et al. Dual requirement for the ETS transcription factors Fli-1 and Erg in hematopoietic stem cells and the megakaryocyte lineage. Proc Natl Acad Sci USA. 2009 Aug. 18; 106(33):13814-9. PubMed PMID: 19666492. Pubmed Central PMCID: 2728977; Liu F, Walmsley M, Rodaway A, Patient R. Fli1 acts at the top of the transcriptional network driving blood and endothelial development. Curr Biol. 2008 Aug. 26; 18(16):1234-40. PubMed PMID: 18718762). While FLI1 is critical from embryogenesis, it is not likely to be critical in mature tissues since its expression is limited to subsets of immune cells and endothelium (Watson D K, Smyth F E, Thompson D M, Cheng J Q, Testa J R, Papas T S, et al. The ERGB/Fli-1 gene: isolation and characterization of a new member of the family of human ETS transcription factors. Cell Growth Differ. 1992 October; 3(10):705-13. PubMed PMID: 1445800; Truong A H, Ben-David Y. The role of Fli-1 in normal cell function and malignant transformation. Oncogene. 2000 Dec. 18; 19(55):6482-9. PubMed PMID: 11175364; Prasad D D, Rao V N, Reddy E S. Structure and expression of human Fli-1 gene. Cancer Res. 1992; 52(20):5833-7). In addition, an approach to targeting FLI1 is to disrupt it from protein interactions with YK-4-279 rather than eliminating its expression.

YK-4-279 Inhibits the Function of ets Family Members ERG, ETV1, and EWS-FLI1

In the childhood/young adult cancer, Ewing sarcoma, the EWS transcription activation domain is fused to an ets family member leading to the novel fusion protein, EWS-FLI1. We identified and validated small molecule YK-4-279 that prevents the binding of EWS-FLI1 to RHA leading to cellular apoptosis in a panel of Ewing sarcoma cell lines (Erkizan H V, Kong Y, Merchant M, Schlottmann S, Barber-Rotenberg J S, Yuan L, et al. A small molecule blocking oncogenic protein EWS-FLI1 interaction with RNA helicase A inhibits growth of Ewing's sarcoma. Nat Med. 2009 July; 15(7):750-6. PubMed PMID: 19584866. eng). We also demonstrated reduced tumor growth in Ewing Sarcoma xenograft models while not affecting the growth of non-EWS-FLI1 containing tumors at similar dosages. As an important proof of specificity, only the (S) enantiomer of YK-4-279 is able to inhibit the functional activities of EWS-FLI1 including binding to RHA, transcript activation, and alternative splicing (Barber-Rotenberg J S, Selvanathan S P, Kong Y, Erkizan H V, Snyder T M, Hong P S, et al. Single Enantiomer of YK-4-279 Demonstrates Specificity in Targeting the Oncogene EWS-FLI1. Oncotarget. 2012 February; 3(2):172-82. PubMed PMID: 22383402. Epub 2012/Mar./3. eng). Advanced prostate cancers over-express ERG, ETV1 or ETV4 by either chromosomal translocation or gene amplification. ERG, ETV1, or ETV4 activity have been directly implicated to increase invasion and metastasis. All three are ets family proteins that share significant homology to FLI1, and have essentially identical DNA binding domains. Prostate cells driven by ERG or ETV1 showed significantly decreased invasion when treated with YK-4-279 (Rahim S, Beauchamp E M, Kong Y, Brown M L, Toretsky J A, Uren A. YK-4-279 Inhibits ERG and ETV1 Mediated Prostate Cancer Cell Invasion. PLoS ONE. 2011; 6(4):e19343. PubMed PMID: 21559405. Pubmed Central PMCID: 3084826. Epub 2011/May/12. eng). This cross-tumoral activity based upon the homology of ets transcription factors led us to explore additional tumors that might be in part driven by an ets transcription factor.

The ets family member FLI1 may therefore be a novel molecular target and YK-4-279 a potential targeted therapeutic in GBM. Orthotopic xenograft and genetically engineered mouse models of GBM are helpful for proof-of-principle studies to support a rationale for advancement to human clinical trials. FLI1 may be a novel vital target for GBM and that YK-4-279 may be useful as a future therapeutic.

GBM is one of the targeted tumor types of The Cancer Genome Atlas (TCGA), with multiple dataset available for analysis. Alterations in FLI1 as well as highly homologous proteins have been searched and it was found that 23% of GBM specimens had alterations that support FLI1 as a novel target (FIG. 8).

Figure 9:
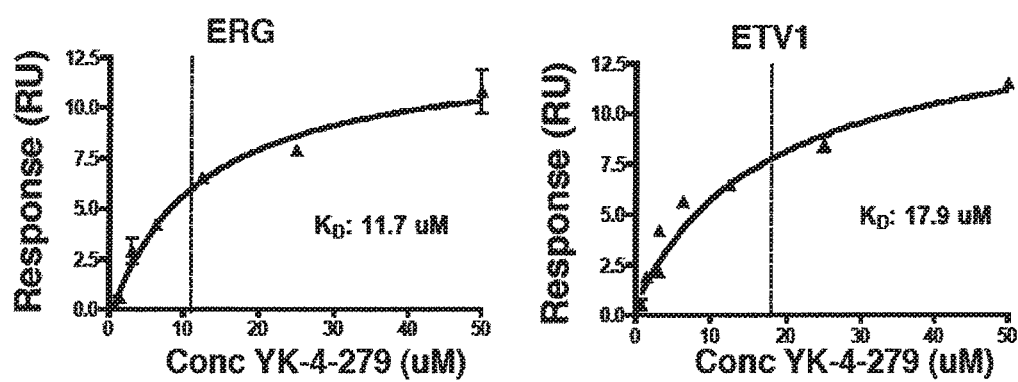
FIG. 9 depicts YK-4-279 binds to ERG and ETV1 with a KD of 11.7 μM and 17.9 μM respectively with steady state kinetics measured on a Biacore T100 instrument.

Considering the close homology between FLI1, ERG and ETV1, the binding of YK-4-279 to ERG and ETV1 was evaluated (Rahim S, Beauchamp E M, Kong Y, Brown M L, Toretsky J A, Uren A. YK-4-279 Inhibits ERG and ETV1 Mediated Prostate Cancer Cell Invasion. PLoS ONE. 2011; 6(4):e19343. PubMed PMID: 21559405. Pubmed Central PMCID: 3084826. Epub 2011 May 12. eng). The affinity (KD) of YK-4-279 for EWS-FLI1 was measured to be 9.5 µM (Erkizan H V, Kong Y, Merchant M, Schlottmann S, Barber-Rotenberg J S, Yuan L, et al. A small molecule blocking oncogenic protein EWS-FLI1 interaction with RNA helicase A inhibits growth of Ewing's sarcoma. Nat Med. 2009 July; 15(7):750-6. PubMed PMID: 19584866. Eng; Barber-Rotenberg J S, Selvanath). The steady state kinetics of YK-4-279 binding to recombinant ERG and ETV1 using surface plasmon resonance had a binding affinity (KD) of 11.7 µM for ERG and 17.4 µM for ETV1, whereas it bound the non-specific protein BSA with a weak affinity of 122.4 µM. FIG. 9 shows that YK-4-279 binds to ERG and ETV1 with a KD of 11.7 µM and 17.9 µM respectively. Steady state kinetics were measured on a Biacore T100 instrument, as previously described (Erkizan H V, Kong Y, Merchant M, Schlottmann S, Barber-Rotenberg J S, Yuan L, et al. A small molecule blocking oncogenic protein EWS-FLI1 interaction with RNA helicase A inhibits growth of Ewing's sarcoma. Nat Med. 2009 July; 15(7): 750-6. PubMed PMID: 19584866. Eng; Barber-Rotenberg J S, Selvanath), SPR sensograms are not shown.

A large sequencing project of GBM that included analysis of XX cell lines has been completed (Solomon D A, Kim T, Diaz-Martinez L A, Fair J, Elkahloun A G, Harris B T, et al. Mutational inactivation of STAG2 causes aneuploidy in human cancer. Science. 2011 Aug. 19; 333(6045):1039-43. PubMed PMID: 21852505. Epub 2011 Aug. 20. eng). Seven cell lines were selected with a spectrum of genetic abnormalities that occur in GBM. Table 3 shows the heterogeneity of GBM cell lines. A panel of GBM cell lines were acquired that represent the heterogeneity of the disease. The (+) indicates the expression of the listed protein, either wild-type or mutant. The (−) indicates the absence of expression on an immunoblot. These cell lines were used to evaluate the expression of FLI1 as well as sensitivity to the inhibitor YK-4-279 (FIG. 3).

TABLE 3

|  | DKMG | DBTRG | 42MGBA | GAMG | U87MG | H4 | 8MGBA |
|---|---|---|---|---|---|---|---|
| EGFR | + | − | + | + | + | − | + |
| Myc | + | − | + | + | + | + | + |
| PTEN | + | − | − | + | + | − | + |
| MDM2 | + | + | − | + | − | − | − |
| p53 | + | + | + | + | − | − | + |
| p14ARF | − | − | − | − | − | − | + |
| 21WAF1/CIP | + | + | + | + | + | + | + |
| CDK4 | + | + | + | + | + | + | + |
| CDK6 | + | + | + | + | − | + | + |
| p16INK4a | − | − | − | − | − | − | + |
| p18INK4c | + | + | + | + | − | + | + |
| RB | + | + | − | + | + | + | − |

Figure 10:
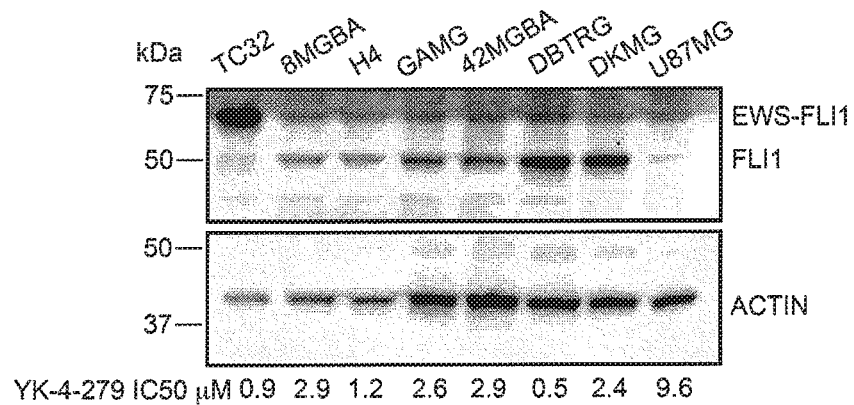
FIG. 10 depicts GBM cell lines overexpress FLI1 which correlates with YK-4-279 sensitivity. Top panel: immunoblot probed with anti-FLI1. Ewing sarcoma TC32 included as positive control. Expected size of FLI1, 50, EWS-FLI1 68 kDa. Bottom panel: graph of IC50 and densiometry.
Figure 10:
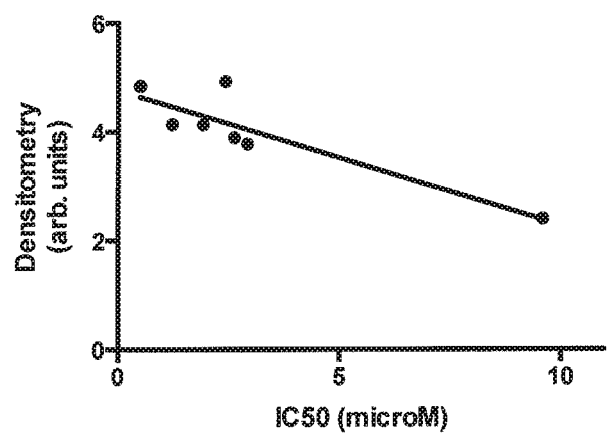

Six of the 7 GBM cell lines (85%) demonstrated FLI1 expression by immunoblot (FIG. 10, top panel). Growth of each of these cell lines was reduced by YK-4-279 with IC50 ranging from 0.5 up to 9.9 µM and an inverse correlation was observed between the level of FLI1 and the sensitivity to YK-4-279 ($r^2$=0.8, FIG. 10).

Figure 11:
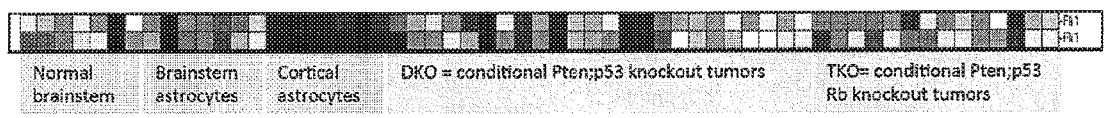
FIG. 11 depicts GEMM overexpression of FLI1 compared with normal brain. RNA was extracted from normal and tumor tissues from control and genetically modified mice. Hybridization followed by normalization showed that FLI1 probes were significantly elevated it the tumors but not normal brain tissues.

To evaluate the potential of FLI1 as a GBM target, two transgenic models were analyzed (Chow L M, Endersby R, Zhu X, Rankin S, Qu C, Zhang J, et al. Cooperativity within and among Pten, p53, and Rb pathways induces high-grade astrocytoma in adult brain. Cancer Cell. 2011 Mar. 8; 19(3):305-16. PubMed PMID: 21397855. Pubmed Central PMCID: 3060664). Very low expression for two FLI1 probe sets comparing normal brainstem, brainstem astrocytes, and cortical astrocytes was observed (FIG. 11). However, 20 of 22 double knock-out (PTEN/p53) and 13 of 14 triple knock-out (PTEN/p53/Rb) tumors had significant expression of the FLI1 based upon the two probesets analyzed (FIG. 11).

Figure 12:
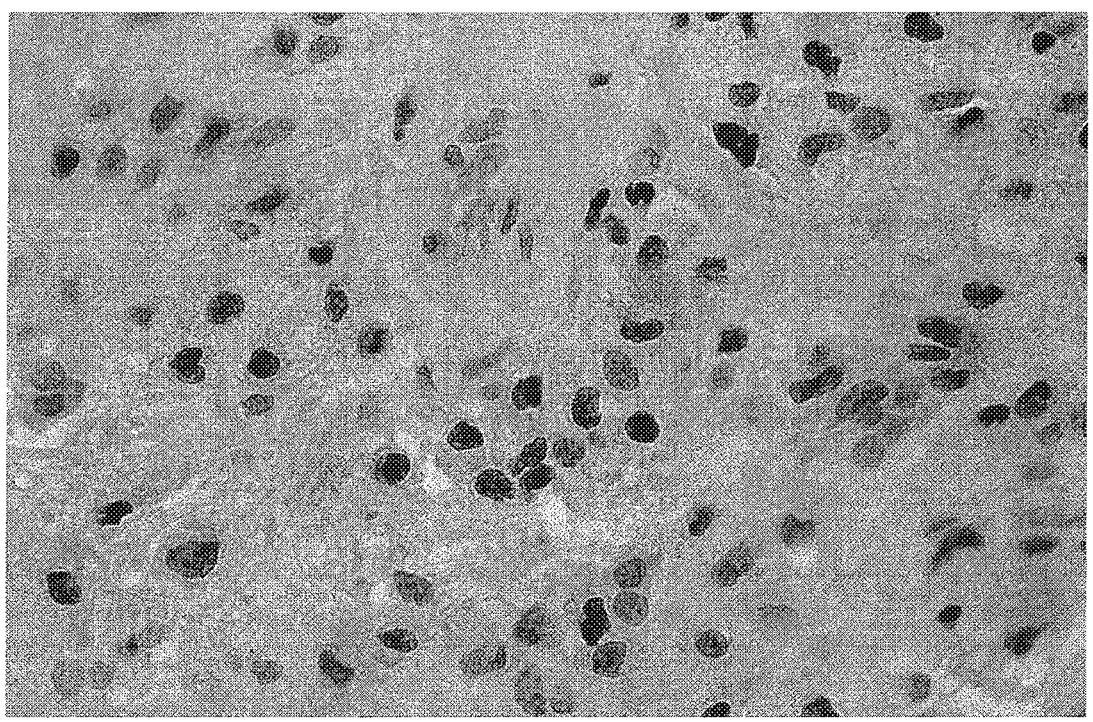
FIG. 12 depicts GBM expression of FLI1. Immunostaining against FLI1 in human glioblastoma shows positive nuclear staining in many of the tumor cells as well as in vessel endothelium and inflammatory cells (40× objective).

In order to determine the FLI1 expression level in human GBM, a panel of GBM was stained with FLI1 antibody. The panel consisted of six randomly selected grade 4 tumors; four of six (66%) showed convincing IHC staining for FLI1 after an antibody was optimized to eliminate cross-reacting proteins and non-specific signal (FIG. 12). Four additional tumors were considered unevaluable since the internal positive control, endothelial cells, were not positive.

One of the significant challenges in getting novel targeted therapy into GBM is overcoming the blood-brain barrier (BBB). As part of a pharmacokinetic evaluation of YK-4-279, tissue levels were measured and compared these with plasma in 12 mice that received 75 mg/kg IV racemic YK-4-279. Levels of YK-4-279 in brain tissue were 74% that of the Ewing sarcoma pretibial xenograft tumor, which would be adequate for inhibiting FLI1. In addition, when rat pharmacokinetics were performed using IV injection of compound, rats became somnolent after rapid injection, which did not occur with slower infusion, thus supporting an ability to pass into the central nervous system across the BBB.

The data provided herein identifies FLI1 as a putative target for GBM. The combination of TCGA data, a panel of cell lines, GEMM model, and panel of IHC from human tumors support further validation of FLI1.

Validation of FLI1 as a Novel Target in GBM

FLI1 as putative target is validated by evaluating whether it is necessary for GBM cell growth. Whether FLI1 is a potential oncogene in glial stem cells is determined. GBM cells are compared with normal human astrocytes and glial stem cells for the importance of FLI1 in order to address the therapeutic index of targeting FLI1. The comparison with normal brain cells is useful to establish FLI1 as a valid target with a preferable therapeutic index.

GBM Cell Lines Require FLI1 Expression for Survival, Growth, and Invasion are Identified Using an shRNA vector that is tagged with EGFP which targets the 3'UTR of FLI1 GBM cell lines require FLI1 expression for survival, growth, and invasion are identified. The shRNA are infected into cells using a lentiviral system. Thus, the relative importance of FLI1 in seven GBM cell lines which span much of the genotypic heterogeneity is evaluated (Table 3). After FLI1 is reduced with shRNA, changes are measure between scrambled shRNA control and FLI1 reduction in monolayer growth, invasion, anchorage-independent growth, and tumorigenesis assays. Cell culture experiments are performed as previously reported (Erkizan H V, Kong Y, Merchant M, Schlottmann S, Barber-Rotenberg J S, Yuan L, et al. A small molecule blocking oncogenic protein EWS-FLI1 interaction with RNA helicase A inhibits growth of Ewing's sarcoma. Nat Med. 2009 July; 15(7): 750-6. PubMed PMID: 19584866. Eng; Rahim S, Beauchamp E M, Kong Y, Brown M L, Toretsky J A, Uren A. YK-4-279 Inhibits ERG and ETV1 Mediated Prostate Cancer Cell Invasion. PLoS ONE. 2011; 6(4):e19343. PubMed PMID: 21559405. Pubmed Central PMCID: 3084826. Epub 2011 May 12. eng). Invasion assays are performed using tumor cells and their invasion through umbilical endothelial cells using an electrical-impedance based technique that monitors and quantifies in real-time the invasion of endothelial cells by malignant tumor cells. The xCELLigence instrument, manufactured by Roche, which measures changes in electrical impedance as cells attach and then as tumor cells disrupt this attachment is used (Rahim S, Beauchamp E M, Kong Y, Brown M L, Toretsky J A, Uren A. YK-4-279 Inhibits ERG and ETV1 Mediated Prostate Cancer Cell Invasion. PLoS ONE. 2011; 6(4):e19343. PubMed PMID: 21559405. Pubmed Central PMCID: 3084826. Epub May 12, 2011 Eng; Rahim S, Uren A. A real-time electrical impedance based technique to measure invasion of endothelial cell monolayer by cancer cells. Journal of visualized experiments : JoVE. 2011 (50). PubMed PMID: 21490581. Pubmed Central PMCID: 3169283). Xenograft experiments use polyclonal shRNA reduced FLI1 in all seven cell lines. Each shRNA FLI1 and scrambled cell lines are stereotactically injected into 5 athymic mice (assisted by Fiandanca). (7 cell lines, 5 animals per cell line, +/−FLI1=70). Growth is monitored by MRI in the GU Animal Imaging shared resource at 7-10 day intervals. Calculations of tumor growth kinetics are performed by region of interest analysis as described, using Bruker Paravision 5.0 software or ImageJ (NIH) (Truong A H, Cervi D, Lee J, Ben-David Y. Direct transcriptional regulation of MDM2 by Fli-1. Oncogene. 2005 Feb. 3; 24(6):962-9. PubMed PMID: 15592502; Pimanda J E, Chan W Y, Donaldson I J, Bowen M, Green A R, Gottgens B. Endoglin expression in the endothelium is regulated by Fli-1, Erg, and Elf-1 acting on the promoter and a -8-kb enhancer. Blood. 2006 Jun. 15; 107(12):4737-45. PubMed PMID: 16484587). Growth statistics of tumors are calculated to build a time-dependent profile of progression and treatment.

Transfection of Normal Human Astrocytes with a Full-Length FLI1 cDNA

To determine the transformative effect of FLI1 upon astrocytes, normal human astrocytes are transfected with a full-length FLI1 cDNA using lentiviral system and evaluate for transformation in soft agar and in vivo orthotopic injection assays. Control (empty vector) and FLI1 transfected polycolonal cells are placed in soft agar for anchorage-independent growth assays (Erkizan H V, Kong Y, Merchant M, Schlottmann S, Barber-Rotenberg J S, Yuan L, et al. A small molecule blocking oncogenic protein EWS-FLI1 interaction with RNA helicase A inhibits growth of Ewing's sarcoma. Nat Med. 2009 July; 15(7):750-6. PubMed PMID: 19584866. eng). Xenograft studies are performed as described above. (2 cell lines+/−FLI1, five animals per cell line=20 animals). Animals are imaged by MRI to assess tumor growth, as described above, every 10 days.

Glial stem cells are evaluated for both for their innate expression of FLI1 and the evaluation of oncogenic effects when FLI1 is exogenously expressed. Published (Lelievre E, Lionneton F, Mattot V, Spruyt N, Soncin F. Ets-1 regulates fli-1 expression in endothelial cells. Identification of ETS binding sites in the fli-1 gene promoter. J Biol Chem. 2002 Jul. 12; 277(28):25143-51. PubMed PMID: 11991951) and novel cell lines are used. To evaluate anchorage-independent growth and invasion assays, for both control and FLI1 expression are performed. In addition, these cell lines are used in xenograft experiments, both transfected with control and FLI1 expression (always proven by immunoblots prior to evaluation). These cells are all be carefully grown in minimal growth media with exogenous growth factors rather than serum to maintain their pristine neural qualities (Rossi S, Orvieto E, Furlanetto A, Laurino L, Ninfo V, Dei Tos A P. Utility of the immunohistochemical detection of FLI-1 expression in round cell and vascular neoplasm using a monoclonal antibody. Mod Pathol. 2004 May; 17(5):547-52. PubMed PMID: 15001993). (3 cell lines+/−FLI1, five animals per cell line=15 animals).

The correlation between YK-4-279 toxicity and FLI1 levels is measured. YK-4-279 targets the FLI1 component of EWS-FLI1 (Barber-Rotenberg J S, Selvanathan S P, Kong Y, Erkizan H V, Snyder T M, Hong PS, et al. Single Enantiomer of YK-4-279 Demonstrates Specificity in Targeting the Oncogene EWS-FLI1. Oncotarget. 2012 February; 3(2): 172-82. PubMed PMID: 22383402. Epub Mar. 3, 2011 Eng; Rahim S, Beauchamp E M, Kong Y, Brown M L, Toretsky J A, Uren A. YK-4-279 Inhibits ERG and ETV1 Mediated Prostate Cancer Cell Invasion. PLoS ONE. 2011; 6(4): e19343. PubMed PMID: 21559405. Pubmed Central PMCID: 3084826. Epub 2011 May 12. eng). Following an evaluation of the effect of FLI1 inhibitor YK-4-279 upon a panel of cell lines and correlation of inhibition with FLI1 expression, these results are compared to the shRNA data. Preliminary data for 7 GBM cell lines with correlation to FLI1 expression. This is expanded to more cell lines with methodology used to generate FIG. 9. Non-tumor glial cell lines are included for these comparisons.

Whether FLI1 expression correlates with other known GBM genotypes and phenotypes is determined. A series of on-line informatics tools from TCGA as well as correlation with our cell line data is used. The analysis includes FLI1 cDNA or protein expression and evaluates whether FLI1 correlates with other known GBM genetic events, such as loss of PTEN, p16, p53 mutation, IDH1 point mutation or EGFR mutation. This is expanded to include patient tumors that are resected at diagnosis and inclusion of FLI1 into the panel of genetic markers evaluated.

Utilizing Animal Models of GBM to Evaluate YK-4-279 as a Therapy

To establish whether YK-4-279 is effective in either slowing growth or causing regression of GBM, YK-4-279 is administered to mice with established GBM. This evaluates both xenograft and transgenic models of GBM.

To establish a method for evaluating intracranial lesions in groups of mice, rather than one at a time with MRI. While the MRI provides a highly detailed graphic and metabolic spectrum of GBM tumors, the time to screen mice limits its use for larger studies. Two GBM cell lines are created, selected from the GBM orthotopic screening of seven cell lines that are used for Xenogen intracranial imaging. The two GBM cell lines are selected based upon their requirements for FLI1, as determined above and growth kinetics. These two GBM cell lines are stably transfected with luciferase so that groups of animals can be screened/monitored using the Xenogen system. For more detailed studies and volumetric comparison, selected animals are evaluated using MRI. Cell lines are screened in vitro followed by an orthotopic xenograft pilot study (2 cell lines×5 animals=10 animals). Prior to Xenogen imaging, animals are injected with luciferase substrate intraperitoneally.

Figure 13A:
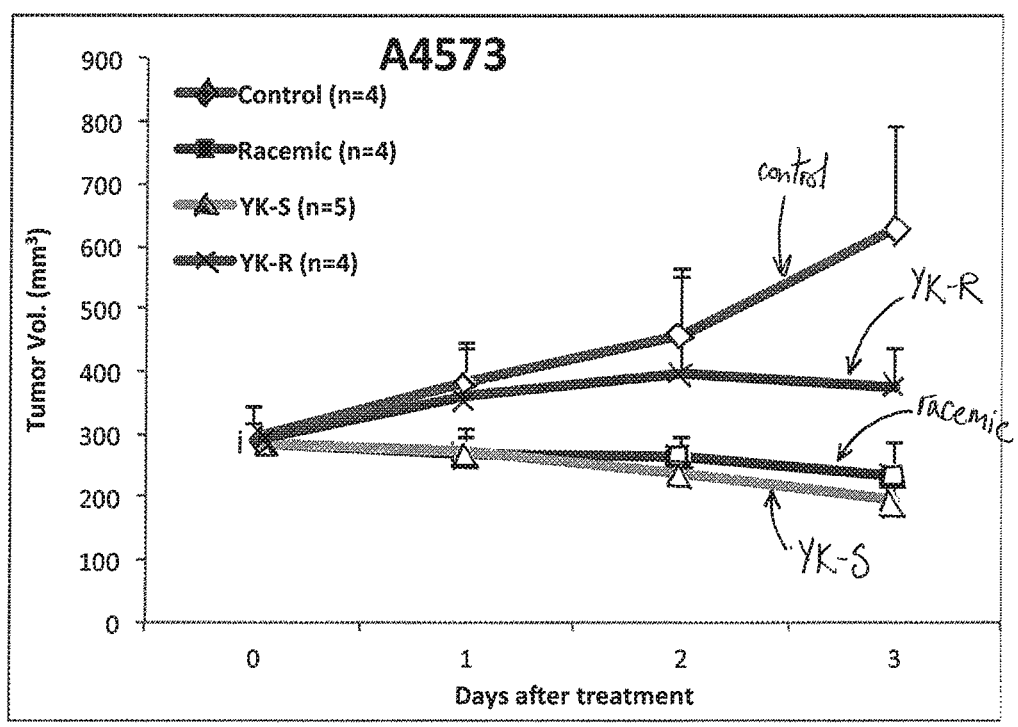
FIG. 13A and 13B illustrate that three days of treatment with (S)-YK-4-279 or racemic shows significant tumor regression.
Figure 13B:
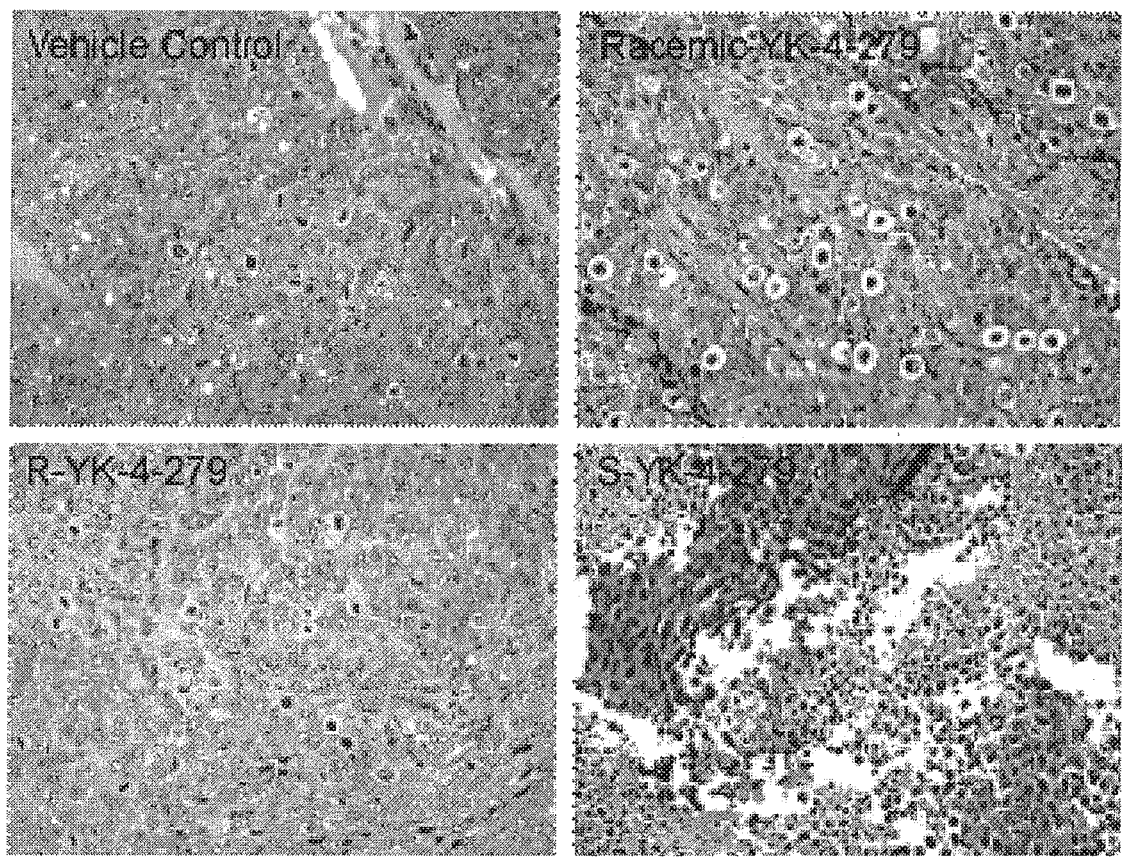

YK-4-279 upon xenograft GBM tumors is evaluated by treating animals seven days after tumor injection and those with symptomatic tumors. Early tumors are screened with Xenogen, and size correlated with MRI, and treatment started when animals 5 mm$^3$ lesions. YK-4-279 passes the blood-brain barrier. Animals are treated with BID injections of YK-4-279 similar to the dose that led to regression of Ewing sarcoma tumors (FIG. 13). The study will measure brain tumor volumes, animal symptoms, and overall survival. At necropsy, tumors and normal adjacent brain will be evaluated by immunohistochemistry for GBM markers, apoptosis, and FLI1 regulated target genes. FIG. 13 illustrates that three days of treatment with (S)-YK-4-279 or racemic shows significant tumor regression. FIG. 13A: Mice with ES xenografts were treated with 400 mg/kg compound or controls as indicated. Starting well-established tumors (300 mm$^3$), mice were treated with intraperitoneal compound for three days, 6 total doses. FIG. 13B: H and E stained tumors from same experiment.

Since the vast majority of patients with GBM present with symptoms and relatively large tumors, YK-4-279 is tested against larger, symptomatic tumors. Thus, YK-4-279 is evaluated on upon well-established GBM, 20 mm$^3$, by MRI, by treating animals after tumors are established and at first signs of symptoms. Tumors at this time are detectable with Xenogen. Animals undergo Xenogen evaluation twice a week while on treatment. The study compares tumor volumes, animal symptoms, and overall survival. At necropsy, tumors and normal adjacent brain are evaluated by immunohistochemistry for GBM markers, apoptosis, and FLI1 regulated target genes.

The GEMM model of GBM is used. Animals are bred as published (Chow L M, Endersby R, Zhu X, Rankin S, Qu C, Zhang J, et al. Cooperativity within and among Pten, p53, and Rb pathways induces high-grade astrocytoma in adult brain. Cancer Cell. 2011 Mar. 8; 19(3):305-16. PubMed PMID: 21397855. Pubmed Central PMCID: 3060664). At approximately 90 days of life, animals have MRI evaluation every 10-14 days to look for onset of GBM. In Experiment 1 animals are treated with YK-4-279 or control starting at day 90 (10 animals in control and treated=20 animals). In Experiment 2 animals are treated at the onset of symptoms or MRI measured tumor of greater than 2 mm in any dimension (10 animals in control and treated=20 animals). Following treatment, animals are evaluated as described above. Administration of YK-4-279 is using the intraperitoneal route.

Data is provided to support further exploration of FLI1 and potentially other ets family members as drivers of GBM.

References pertaining to selected cancers include the following: CBTRUS Statistical Report: Primary Brain and Central Nervous System Tumors Diagnosed in the United States in 2004-2008 (Mar. 23, 2012 Revision). Central Brain Tumor Registry of the United States [Internet]. 2012; http://www.cbtrus.org. Available from: http://www.cbtrus.org.

Example 11

Use of YK-4-279 for Treating Lung Cancer

Epithelial-to-mesenchymal transition (EMT) is a key component of the pathogenesis of carcinomas. EMT induces significant changes in cell morphology and behavior that impart metastatic and drug-resistant phenotypes. Moreover, there is evidence suggesting that EMT participates in the generation of cancer stem cells. Lung cancer is the leading cause of cancer-related mortality, mainly because it is typically diagnosed at advanced stages that are difficult to treat. Advances in our understanding of the molecular genetics of cancers have identified individual molecules required for tumorigenesis. This has led to the development of targeted therapies that are successful for treating certain cancers. Examples of these molecular targets include cell surface growth factor receptors and intracellular protein tyrosine kinases. Unfortunately, such treatments have not significantly improved overall survival or quality of life for patients with lung cancer.

Recent discoveries described here have led to the hypothesis that the product of the E-26 Transforming Sequence (ETS)-related gene ERG, a member of the ETS family of transcription factors, plays an important role in EMT. Moreover, it induces EMT and the malignant progression of epithelial cells through direct up-regulation of the expression of zinc finger E-box binding homeobox 1 and 2 genes (ZEB1, ZEB2). ZEB1 is linked to EMT in lung cancer cells, and inhibiting its expression using siRNA not only reverses EMT but also inhibits tumor growth in vitro and in vivo. Because lung cancer cells express high levels of ERG, ERG may induce EMT through ZEB. Experiments are conducted that determine whether ERG participates in EMT of lung cancer cells mediated by ZEB1/2. New formulations of YK-4-279 are produced and evaluated for treating lung cancer.

ERG as a transcription factor modulates expression of many genes that are important for carcinogenesis. Earlier observations suggested that oncogenic properties of ERG include its ability to induce epithelial-to-mesenchymal transition (EMT). In different experimental systems, ERG has been shown to induce expression of zinc finger E-box binding homeobox 1 and 2 genes (ZEB1, ZEB2), which are positive regulators of EMT in cancer cells. Since EMT results in metastasis and drug resistance in NSCLC, inhibition of molecular pathways leading to EMT may have significant clinical utility.

The role of ERG in mediating EMT in lung cancer cells is determined. EMT and drug resistance phenotypes of NSCLC cell lines in response to changes in ERG expression is determined. If ERG induces EMT like it does in other epithelial tumors is determined. Further, if the ERG mediated EMT in NSCLC is through ZEB 1/2 genes is determined. These experiments involve inhibition of ERG and ZEB expression in NSCLC cells by RNAi technologies. EMT phenotype is evaluated by real-time PCR and western blotting for established EMT markers.

Formulations of YK-4-279 that can be administered parenterally are produced and the effects of YK-4-279 on the proliferation and malignant properties of lung cancer cells are determined. An examples excipient is β-hydroxypropyl cyclodextrin (β-HPCD). NSCLC cells are treated with YK-4-279 and their response is measured in multiple in vitro and in vivo models. Cell viability, chemotaxis, endothelial cell invasion and xenograft growth in immunocompromised mice is measured. The potential synergy between YK-4-279 and most common chemotherapeutic agents for NSCLC is determined. The properties of drug resistance and high metastatic potential of NSCLC cells, mediated by EMT, contribute significantly to the poor prognosis of patients with NSCLC.

Figure 14:
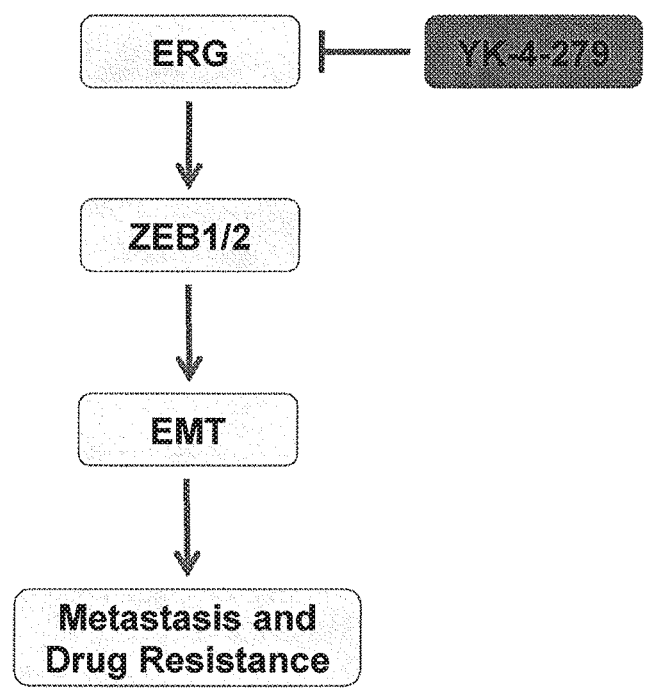
FIG. 14 illustrates ERG induces expression of ZEB 1 and ZEB2, which activate EMT leading to lung cancer metastasis and drug resistance.

The properties of drug resistance and high metastatic potential of NSCLC cells, mediated by EMT, contribute significantly to the poor prognosis of patients with NSCLC. A specific protein to reverse the EMT phenotype in lung cancer is targeted using a small molecule. FIG. 14 illustrates ERG induces expression of ZEB1 and ZEB2, which activate EMT leading to lung cancer metastasis and drug resistance.

Targeting drugs to specific molecules required for the growth of cancer cells remains a difficult challenge despite recent advances in molecular and cellular biology. Although proteins that drive the unregulated reproduction of cancer cells are known, only a few have served as targets of effective therapies. Examples include an intracellular protein tyrosine kinase whose activity is inhibited by a small molecule called imatinib mesylate used to treat chronic myelogenous leukemia; and a monoclonal antibody (trastuzumab) used to treat breast cancers, is targeted to a cell surface growth factor receptor. These limited but significant and highly encouraging successes have stimulated continuing and robust research by the pharmaceutical industry. Inhibiting the activity of an enzyme or the activation of receptor are well-established goals of drug development for numerous diseases in addition to cancer, because the biochemistry of these proteins is so well understood. In contrast, the biochemistry involved in the binding of proteins to one another is much more complex and poorly understood, and inhibiting these interactions has therefore received relatively little attention.

ERG is a further challenge for designing a targeted therapy, because it localizes to the nucleus and lacks enzyme activity. YK-4-279 is a small molecule that inhibits ERG's transcriptional activity, and is investigated for its role in NSCLC. Whether YK-4-279, by binding to and interfering with ERG function required for EMT is determined (FIG. 14), can be used to treat NSCLC.

ERG is an oncogenic protein. The E-26 Transforming Sequence (ETS)-related gene ERG encodes a member of the ETS family of transcription factors that is essential for endothelial homeostasis, differentiation, and angiogenesis in many tissues (Liu F, Patient R. Genome-wide analysis of the zebrafish ETS family identifies three genes required for hemangioblast differentiation or angiogenesis. Circulation research. 2008; 103:1147-54; Sashida G, Bazzoli E, Menendez S, Liu Y, Nimer S D. The oncogenic role of the ETS transcription factors MEF and ERG. Cell cycle. 2010; 9:3457-9). Evidence suggests that the activities of certain genes that are regulated by ERG are required for angiogenesis. For example, VE-cadherin, which requires ERG for its expression, is essential for endothelial junctional stability and endothelial survival, both critical processes in angiogenesis (Yuan L, Sacharidou A, Stratman A N, Le Bras A, Zwiers P J, Spokes K, et al. RhoJ is an endothelial cell-restricted Rho GTPase that mediates vascular morphogenesis and is regulated by the transcription factor ERG. Blood. 2011; 118:1145-53). In carcinogenesis, ETS transcription factors are involved in the regulation of numerous genes that participate in processes required for metastasis, including degradation of the extracellular matrix, and formation of cell-to-cell and cell-to-matrix junctions (Lelievre E, Lionneton F, Soncin F, Vandenbunder B. The Ets family contains transcriptional activators and repressors involved in angiogenesis. The international journal of biochemistry & cell biology. 2001; 33:391-407). Specific examples include the receptor for vascular endothelial growth factor, endoglin, matrix metalloproteinases, collagenase 1, and heme oxygenase 1. ERG is overexpressed in hematopoietic and epithelial cell cancers and acts as a potent oncogene in human prostate cancers (Chen Y, Chi P, Rockowitz S, Iaquinta P J, Shamu T, Shukla S, et al. ETS factors reprogram the androgen receptor cistrome and prime prostate tumorigenesis in response to PTEN loss. Nature medicine. 2013; Rahim S, Uren A. Emergence of ETS transcription factors as diagnostic tools and therapeutic targets in prostate cancer. American journal of translational research. 2013; 5:254-68; Turner D P, Watson D K. ETS transcription factors: oncogenes and tumor suppressor genes as therapeutic targets for prostate cancer. Expert review of anticancer therapy. 2008; 8:33-42).

ERG and EMT signifies poor clinical outcome in NSCLC. Notable findings leading to our interest in the role of ERG in lung cancers include the detection of relatively high levels of ERG expression in NSCLCs and the presence of alternatively spliced versions of ERG in 100% of lung tumor samples compared with normal tissue (Xi L, Feber A, Gupta V, Wu M, Bergemann A D, Landreneau R J, et al. Whole genome exon arrays identify differential expression of alternatively spliced, cancer-related genes in lung cancer. Nucleic acids research. 2008; 36:6535-47). Analysis of mRNA expression by micro array: ERG mRNA expression ranking is in top 8% (Ramaswamy S, Ross K N, Lander E S, Golub T R. A molecular signature of metastasis in primary solid tumors. Nature genetics. 2003; 33:49-54), and in top 11% (Ding L, Getz G, Wheeler D A, Mardis E R, McLellan M D, Cibulskis K, et al. Somatic mutations affect key pathways in lung adenocarcinoma. Nature. 2008; 455:1069-75) in NSCLC tissue samples. Since ERG target genes are involved in EMT phenotype we hypothesized that ERG mediated EMT may contribute to malignant phenotype of NSCLC.

EMT was first described in early embryonic development when cells lose their epithelial characteristics and acquire mesenchymal phenotypes (Sato M, Shames D S, Hasegawa Y. Emerging evidence of epithelial-to-mesenchymal transition in lung carcinogenesis. Respirology. 2012; 17:1048-59). As EMT progresses, cells acquire a more motile and invasive phenotype. Therefore, EMT emerged as an important component of carcinogenesis. The associations between EMT and NSCLC local invasion, angiogenesis, distant metastasis as well as drug resistance and anti-apoptotic phenotypes have been demonstrated by numerous studies conducted in vivo and in vitro (Table 4). For example, the expression of molecules involved in EMT correlate with the clinico-pathological features of NSCLC, including increased metastasis and shortened overall survival of patients (Dauphin M, Barbe C, Lemaire S, Nawrocki-Raby B, Lagonotte E, Delepine G, et al. Vimentin expression predicts the occurrence of metastases in non small cell lung carcinomas. Lung cancer. 2013; 81:117-22). Moreover, the important role of EMT in carcinogenesis is indicated by cellular phenotypes characteristic of stem cells (Mani S A, Guo W, Liao M J, Eaton E N, Ayyanan A, Zhou A Y, et al. The epithelial-mesenchymal transition generates cells with properties of stem cells. Cell. 2008; 133:704-15). Taken together, these studies provide strong justification for inhibiting EMT that occurs in the development of lung cancer. Table 4 lists molecules involved in EMT that correlate with clinical features in NSCLC.

TABLE 4

| EMT Genes | Clinical features | References |
|---|---|---|
| Epithelial Cadherin | Longer overall survival | Nakata S, Sugio K, Uramoto H, Oyama T, Hanagiri T, Morita M, et al. The methylation status and protein expression of CDH1, p16(INK4A), and fragile histidine triad in nonsmall cell lung carcinoma: epigenetic silencing, clinical features, and prognostic significance. Cancer. 2006; 106: 2190-9. |
| | Negative for lymph node metastasis | Kase S, Sugio K, Yamazaki K, Okamoto T, Yano T, Sugimachi K. Expression of E-cadherin and beta-catenin in human non-small cell lung cancer and the clinical significance. Clinical cancer research: an official journal of the American Association for Cancer Research. 2000; 6: 4789-96. |
| SLUG | Postoperative relapse | Shih J Y, Tsai M F, Chang T H, Chang Y L, Yuan A, Yu C J, et al. Transcription repressor slug promotes carcinoma invasion and predicts outcome of patients with lung adenocarcinoma. Clinical cancer research: an official journal of the American Association for Cancer Research. 2005; 11: 8070-8. |

TABLE 4-continued

| EMT Genes | Clinical features | References |
|---|---|---|
| | Shorter overall survival | Chiou S H, Wang M L, Chou Y T, Chen C J, Hong C F, Hsieh W J, et al. Coexpression of Oct4 and Nanog enhances malignancy in lung adenocarcinoma by inducing cancer stem cell-like properties and epithelial-mesenchymal transdifferentiation. Cancer research. 2010; 70: 10433-44. |
| SNAIL | Shorter overall survival | Yanagawa J, Walser T C, Zhu L X, Hong L, Fishbein M C, Mah V, et al. Snail promotes CXCR2 ligand-dependent tumor progression in non-small cell lung carcinoma. Clinical cancer research: an official journal of the American Association for Cancer Research. 2009; 15: 6820-9. |
| TWIST | Shorter overall survival | Hung J J, Yang M H, Hsu H S, Hsu W H, Liu J S, Wu K J. Prognostic significance of hypoxia-inducible factor-1alpha, TWIST1 and Snail expression in resectable non-small cell lung cancer. Thorax. 2009; 64: 1082-9. |
| HIF-1 alpha | Shorter overall survival Shorter recurrence free survival | |

ERG target gene ZEB1 mediates EMT. EMT is a complex cellular response that involves multiple signaling pathways. The zinc finger E-box-binding homeobox (ZEB) proteins are key regulators of EMT (Takeyama Y, Sato M, Horio M, Hase T, Yoshida K, Yokoyama T, et al. Knockdown of ZEB 1, a master epithelial-to-mesenchymal transition (EMT) gene, suppresses anchorage-independent cell growth of lung cancer cells. Cancer letters. 2010; 296:216-24). In particular, ZEB1 plays a predominant role in the EMT-associated carcinogenic phenotypes of lung cancer by regulating the expression of genes that encode proteins that participate in EMT. For example, inhibition of ZEB 1 expression by siRNA in lung cancer cell lines results in the reversal of EMT, increased sensitivity to docetaxel, and reduced growth of lung cancer cells in vitro and in vivo (Ren J, Chen Y, Song H, Chen L, Wang R. Inhibition of ZEB 1 reverses EMT and chemoresistance in docetaxel-resistant human lung adenocarcinoma cell line. Journal of cellular biochemistry. 2013; 114:1395-403). Most important, ERG mediates EMT in prostate cancer cells through the ZEB axis (Leshem O, Madar S, Kogan-Sakin I, Kamer I, Goldstein I, Brosh R, et al. TMPRSS2/ERG promotes epithelial to mesenchymal transition through the ZEB1/ZEB2 axis in a prostate cancer model. PloS one. 2011; 6:e21650). Moreover, miR-30 suppresses EMT in prostate cancer cells by directly targeting ERG expression (Kao C J, Martiniez A, Shi X B, Yang J, Evans C P, Dobi A, et al. miR-30 as a tumor suppressor connects EGF/Src signal to ERG and EMT. Oncogene. 2013). These and other studies indicate that it is reasonable to conclude that efforts to target ZEB 1 and ZEB2 to reverse EMT in lung cancer may be successful. Because RNAi technologies are not advanced enough for clinical applications, it will be necessary to identify alternative mechanisms to inhibit ZEB1 expression in lung cancers. It is known that ERG binding sites are present in the ZEB 1 and ZEB2 promoter regions (Leshem O, Madar S, Kogan-Sakin I, Kamer I, Goldstein I, Brosh R, et al. TMPRSS2/ERG promotes epithelial to mesenchymal transition through the ZEB1/ZEB2 axis in a prostate cancer model. PloS one. 2011; 6:e21650). In 2009 we discovered YK-4-279 as an inhibitor of EWS-FLI1, a fusion protein encoded by a tumor-specific rearranged gene in Ewing Sarcoma (Erkizan H V, Kong Y, Merchant M, Schlottmann S, Barber-Rotenberg J S, Yuan L, et al. A small molecule blocking oncogenic protein EWS-FLI1 interaction with RNA helicase A inhibits growth of Ewing's sarcoma. Nature medicine. 2009; 15:750-6). More recently, based on the homology between two ETS members, FLI1 and ERG, YK-4-279 binds directly to ERG and inhibits its transcriptional activity (Rahim S, Beauchamp EM, Kong Y, Brown M L, Toretsky J A, Uren A. YK-4-279 inhibits ERG and ETV1 mediated prostate cancer cell invasion. PloS one. 2011; 6:e19343). Inhibition of ERG function in lung cancer cells may reverse EMT mediated by ZEB proteins and lead to inhibition of metastatic growth and increased sensitivity to chemotherapeutic drugs.

YK-4-279 Binds ERG

Figure 15:
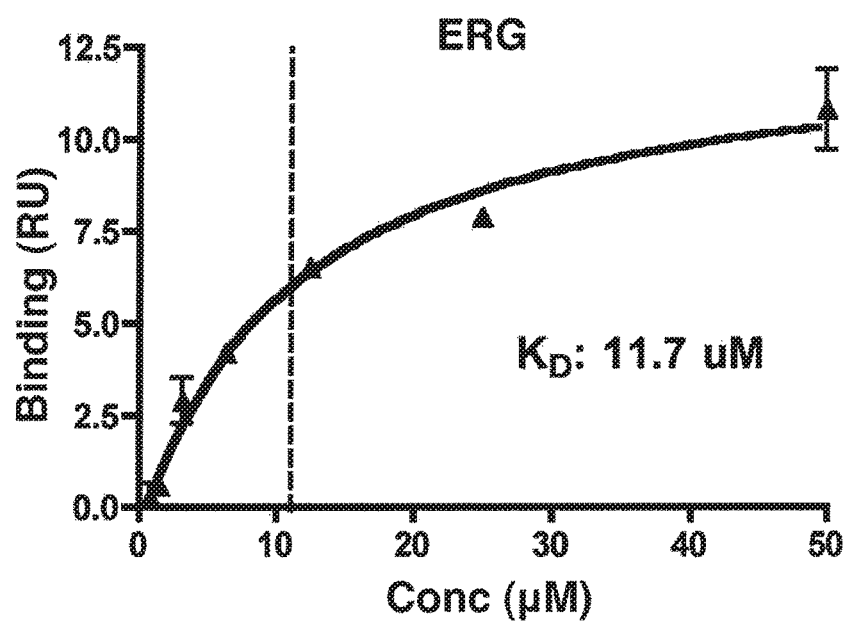
FIG. 15 illustrates YK-4-279 directly interacts with ERG protein. Purified recombinant ERG was immobilized on Biacore CM5 microchips, and direct binding to eight different YK-4-279 concentrations (0.1-50 µM) was determined by SPR. Steady state KD was calculated using Biaevaluation software.

YK-4-279, a small molecule that binds directly to EWS-FLI1 and inhibits the growth of Ewing Sarcoma cells (Erkizan H V, Kong Y, Merchant M, Schlottmann S, Barber-Rotenberg J S, Yuan L, et al. A small molecule blocking oncogenic protein EWS-FLI1 interaction with RNA helicase A inhibits growth of Ewing's sarcoma. Nature medicine. 2009; 15:750-6). EWS-FLI1 is the product of a chromosomal translocation. FLI1 is an ETS family transcription factor with a conserved DNA binding domain. Alignment of FLI1 with another ETS family member, ERG, amino acid sequence shows significant similarities (63.5% identity, 80.2% homology). Commercially available recombinant ERG protein (Origene, Rockville, Md.) was obtained and measured direct binding affinity for YK-4-279 on a Biacore T-100 (FIG. 15), which detects molecular interactions in real time without a reporter moiety. Recombinant protein was immobilized on Biacore microchips and binding was measured in the presence of varying YK-4-279 concentrations. We detected YK-4-279 binding to ERG with a steady state KD of 11.7 µM. FIG. 15 illustrates YK-4-279 directly interacts with ERG protein. Purified recombinant ERG was immobilized on Biacore CM5 microchips, and direct binding to eight different YK-4-279 concentrations (0.1-50 µM) was determined by SPR. Steady state KD was calculated using Biaevaluation software.

Figure 16A:
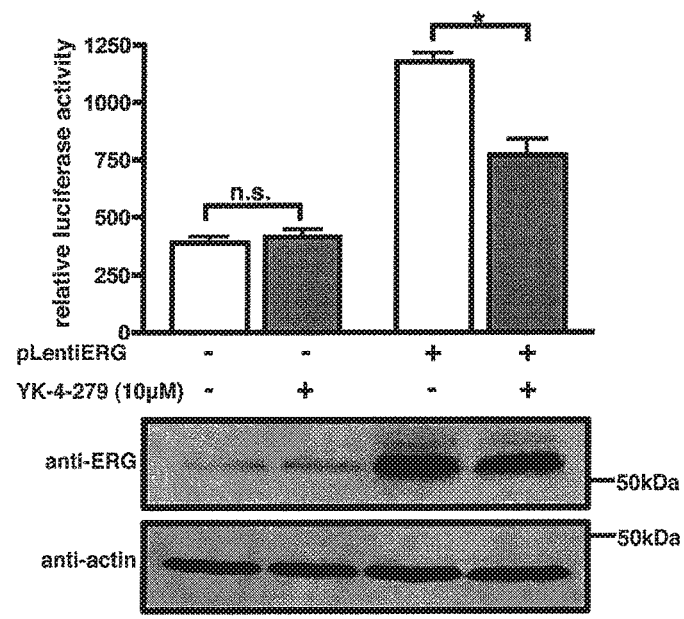
FIGS. 16A and 16B illustrates that YK-4-279 inhibits transcriptional activity of ERG.
Figure 16B:
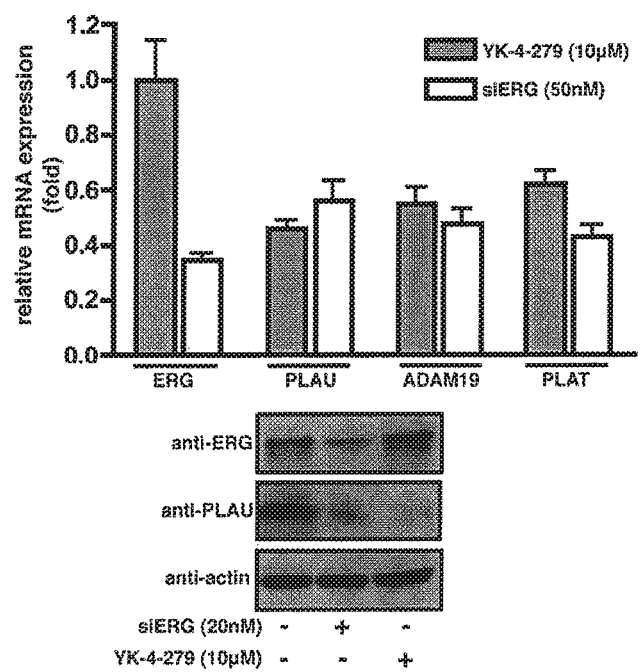

YK-4279 inhibits transcriptional activity of ERG. ETS proteins control expression of target genes encoding proteins that participate in diverse biochemical processes, many of which contribute to oncogenic growth (Hollenhorst P C, McIntosh L P, Graves B J. Genomic and biochemical insights into the specificity of ETS transcription factors. Annual review of biochemistry. 2011; 80:437-71). The effect of YK-4-279 on ERG's transcriptional activity was tested utilizing promoter reporter assays and endogenous gene expression profiling. YK-4-279 inhibited ERG activation of an ETS target gene promoter (Id2) controlling luciferase expression in COST cells (FIG. 16A). VCaP prostate cancer cells possess the TMPRSS2/ERG fusion gene, where ERG induces expression of specific endogenous target genes such as PLAU, ADAM19 and PLAT. Real time (RT)-PCR analysis revealed that YK-4-279 significantly inhibited their expression but not that of ERG expression (FIG. 16B). These findings were extended to the protein level for ERG and PLAU. Inhibition by YK-4-279 was comparable to that observed when cells were treated with ERG siRNA (FIG. 16B) (Rahim S, Beauchamp E M, Kong Y, Brown M L, Toretsky J A, Uren A. YK-4-279 inhibits ERG and ETV1 mediated prostate cancer cell invasion. PloS one. 2011; 6:e19343). Since epithelial cells do not express FLI1, YK-4-279's effects were most likely due to inhibiting ERG. This provides further evidence that YK-4-279 is not simply a general inhibitor of transcription and translation (ERG mRNA and protein levels did not change), but it specifically inhibits the transcriptional activities of ETS family proteins.

ERG is Expressed in NSCLC Cell Lines and Induces EMT Markers

Figure 17:
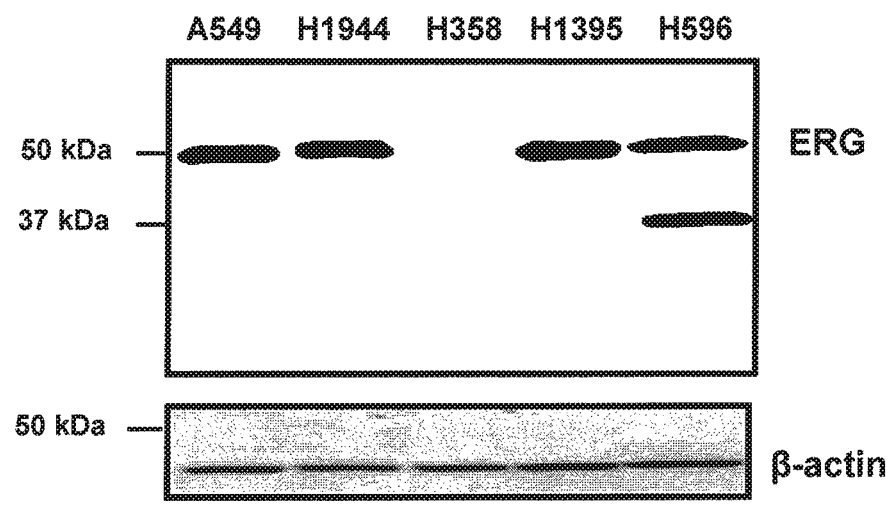
FIG. 17 illustrates that NSCLC cell lines express ERG protein. Total protein lysates from indicated NSCLC cell lines were separated by PAGE. Expression of human ERG protein was confirmed by western blotting using an anti-ERG antibody (upper panel). Molecular weight markers are given on the left. Equal protein loading was confirmed by stripping and re-blotting the same membrane with an anti-beta-actin antibody (lower panel).

Five NSCLC cell lines were examined to confirm that significant ERG expression is present similar to what was observed in human tumor samples. A western blot analysis of A549, H1944, H358, H1395, and H596 cell lysates were performed (FIG. 17). Four out of 5 cell lines expressed high levels of ERG protein. H358 cell line that expressed very little ERG will be used as a negative control in our studies.

Figure 18A:
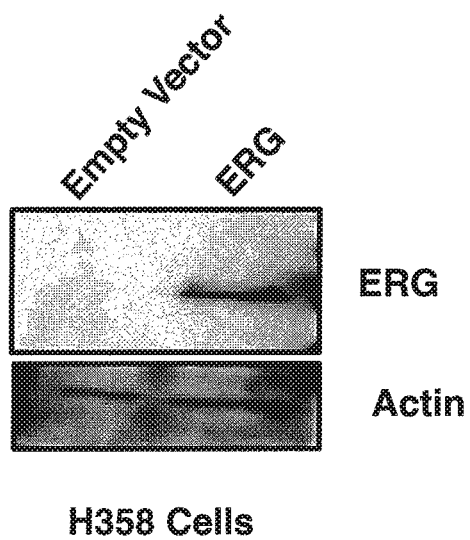
FIGS. 18A and 18B illustrate that ERG expression induces EMT markers. H358 NSCLC cells were transfected with a cDNA coding for human ERG protein. Increased ERG expression was detected by western blotting (FIG. 18A). Real-time PCR analysis revealed higher expression of ZEB 1 and FOXC2 in ERG expressing cells (FIG. 18B). Data is first normalized for 18S RNA and then expressed as fold induction over empty vector transfected cells.

Earlier work in other tumor types suggested that ERG may induce EMT. In order to test, if the same effect exists in NSCLC cells, an ERG expression vector was transfected to H358 cells, which has relatively very low levels of endogenous ERG protein (FIG. 18A). When the H358 cells expressed high level of ERG protein, we observed a significant increase in expression of two EMT markers, ZEB 1 and Foxc2 (FIG. 18B), suggesting that ERG can induce EMT in NSCLC cells.

Figure 18B:
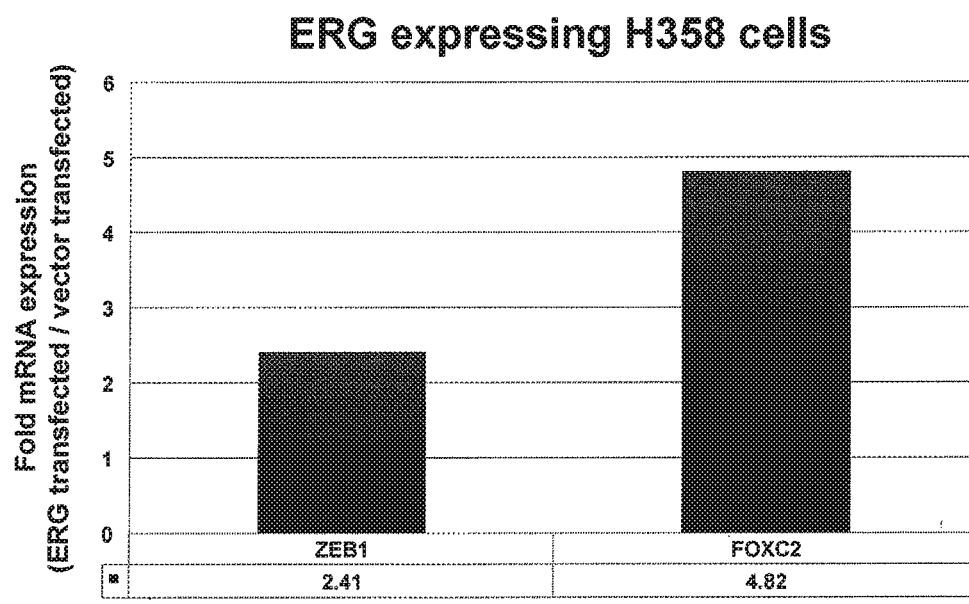

FIG. 18A and 18B illustrate that ERG expression induces EMT markers. H358 NSCLC cells were transfected with a cDNA coding for human ERG protein. Increased ERG expression was detected by western blotting (FIG. 18A). Real-time PCR analysis revealed higher expression of ZEB 1 and FOXC2 in ERG expressing cells (FIG. 18B). Data is first normalized for 18S RNA and then expressed as fold induction over empty vector transfected cells.

YK-4-279 Inhibits Expression of ERG Dependent EMT Markers

Figure 19:
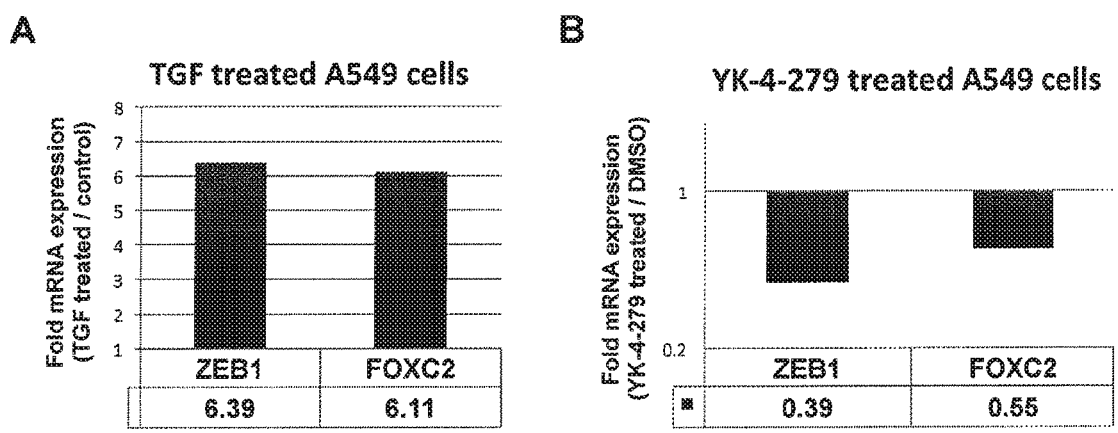
FIG. 19 illustrates that YK-4-279 inhibits EMT in NSCLC. A549 cells expressed higher levels of ZEB 1 and FOXC2 with increased TGF-β expression and reduced levels with ERG inhibition by YK-4-279. Data was first normalized to 18S RNA and then fold expression calculated by dividing to control for each group.

A549 cells express relatively high levels of ERG protein (FIG. 17). We evaluated the EMT marker gene expression in these cells by real-time quantitative PCR (FIG. 19). TGF-β, a known EMT inducer, treatment of A549 cells resulted in increased ZEB1 and FOXC2 expression. When the untransfected A549 cells were treated with the ERG inhibitor, YK-4-279, we observed the complete opposite, both ZEB and FOXC2 expression was inhibited.

The preliminary data presented here confirms that YK-4-279 directly binds to ERG protein and inhibit its function as a transcription factor. Furthermore, we demonstrated that ERG can induce EMT markers in NSCLC cells and this effect can be reversed by YK-4-279.

Experiments summarized in this section test the hypothesis that ERG contributes to the pathogenesis of NSCLC by inducing (EMT), and that ERG can serve as a target for lung cancer therapy. We establish that ERG may be successfully inhibited by YK-4-279 as a novel therapeutic approach.

The Role of ERG in Mediating EMT in Lung Cancer Cells

We assess the effects of modulating the levels of ERG expression on lung cancer cell lines, particularly regarding EMT. The H358 cell line, derived from a non-small cell lung cancer, expresses relatively low levels of endogenous ERG protein (FIG. 17). We introduce an ERG-expression vector to elevate ERG levels in these cells. Other lung cancer cell lines (A549, H1944, H1395, and H596) express very high levels of endogenous ERG. We use RNA interference techniques (shRNA or siRNA) targeted to ERG to reduce its expression levels in these cells. In each case, the effect on EMT is assessed by determining the expression levels of mRNAs and their cognate proteins that serve as specific markers for EMT as follows: E-cadherin, vimentin, Snail, Slug, and ZEB1. A heightened EMT expression profile in H358 cells overexpressing ERG or a reduced EMT expression profile in cells (A549, H1944, H1395, and H596) in which ERG expression has been inhibited by RNA interference is observed, we extend these studies by determining the effects of ZEB 1 and ZEB 2 siRNAs. The hypothesis that ERG mediates EMT functions through ZEB1 and ZEB2 is supported if the effect of ERG on EMT is diminished when ZEB1 and ZEB2 expression is inhibited.

We determine IC50 values for common chemotherapeutic agents, cisplatin, paclitaxel, gemcitabine, etoposide, and vinblastine on five NSCLC cell lines. Cell viability is determined by electric impedance and WST assays. Once the baseline IC50 values are established, we repeat the experiment with altered EGR expression. ERG expression is inhibited in in A549, H1944, H1395, and H596 cells with shRNA. If stable shRNA expression and reduced ERG protein expression cannot be achieved, we will perform these experiments with transient transfection of siRNA targeting ERG. Reducing ERG expression in NSCLC cell lines is expected to shift the IC50 curves significantly to the left such that the cells become more sensitive these chemotherapeutic agents. To complement these experiments we establish a stable H358 cell line that express high levels of ERG protein from a mammalian expression vector. In this cell line we see a significant shift to right in the IC50 curve such that the cells become more resistant to chemotherapy.

New formulations of YK-4-279 that can be administered parenterally are produced and the effects of YK-4-279 on the proliferation and malignant properties of lung cancer cells are determined.

The lead excipient is β-hydroxypropyl cyclodextrin ((3-HPCD), while β-HPCD is a clinically viable vehicle. The top seven formulations are compared to kinetics for HPβCD. CD-1 are injected IP followed by time-points at 0, 5, 10, 15, 30, 60, 120, 180, 240 and 480 minutes. A 24 hour point also checks for delayed clearance. A series of CD-1 mice with IV injection followed by time-points at 0, 5, 10, 15, 30, 60, 120, 180, 240 are used to measure absorption levels. Plasma are analyzed and pharmacokinetic parameters calculated. The goal of these studies is to determine if there is a superior preparation to HPβCD by comparing absorption and half-life. If a formulation can achieve IP absorption and sustain plasma levels of greater than 3 µM for 24 hours, we consider this a significant improvement. This allows us to evaluate daily dosing in comparison with continuous infusion therapy. The use of a daily dose rather than continuous IV is preferred for future animal and clinical studies.

We inhibit ERG function by treating cells with YK-4-279. Changes in EMT markers are determined as described above to confirm that YK-4-279 treatment results in the same EMT marker expression profile as the lack of ERG (siRNA or shRNA). The goal of following experiments is to assess the effects on functional outcomes when EMT is altered. For this purpose, we evaluate surrogate markers of the malignant phenotype as follows: cell motility, chemotaxis, invasion of an endothelial cell monolayer, growth on plastic, growth in soft agar, and in vivo growth as xenografts. In parallel experiments, cells are treated with YK-4-279 and varying concentrations of different chemotherapeutic agents for NSCLC, including cisplatin, paclitaxel, gemcitabine, etoposide, and vinblastine. We observe a synergistic inhibitory effect induced by YK-4-279 in combination with these drugs. To support the hypotheses that inhibiting ERG expression diminishes EMT through ZEB 1/2, we determine whether enforced overexpression of ZEB1/2 reverses the effects of YK-4-279 on cell phenotype.

We test the effects of YK-4-279 on NSCLC cell motility and invasion. We test YK-4-279 for its ability to inhibit NSCLC cell invasion using the xCELLigence system. This new method allows real-time measurement of cell motility in a classical Boyden chamber format with a layer of gold electrodes on the underneath surface of the porous membrane (xCELLigence sim-plates). As the cells move from the upper chamber through the membrane towards a chemoattractant in the lower chamber, they increase electric impedance on the under surface of the membrane, which is recorded in real-time. The same instrument is also used for measuring invasion through an endothelial monolayer (Rahim S, Uren A. A real-time electrical impedance based technique to measure invasion of endothelial cell monolayer by cancer cells. Journal of visualized experiments: JoVE. 2011). In this experimental format, human umbilical vein endothelial cells (HUVEC) grow on regular cell culture plates with gold electrodes on the surface (xCELLigence E-plates). Once the endothelial cells form a stable monolayer, NSCLC cells are added on top. As the cancer cells break tight junctions between endothelial cells and penetrate through the endothelial monolayer, they alter the electric impedance. These experiments allow us to evaluate if YK-4-279 alters motility, chemotaxis and invasive phenotype of NSCLC cells We perform synergy studies in cell culture by titrating YK-4-279 and chemotherapeutic agents (cisplatin, paclitaxel, gemcitabine, etoposide, and vinblastine). Cell death is used as the end point and any potential synergy is calculated by combination index (CI) isobologram equation method (Chou T C. Theoretical basis, experimental design, and computerized simulation of synergism and antagonism in drug combination studies. Pharmacological reviews. 2006; 58:621-81).

We test the effect of ERG inhibition on growth of 3 different human NSCLC xenografts (two with high ERG expression and one with low ERG expression). Cell suspension prepared in matrigel is subcutaneously implanted into four- to six-week-old male SCID mice. Adjusting for take rate, two groups of animals (10 animals/xenograft line) are administered the inhibitor YK-4-279, and the carrier only placebo based on the formulation studies for each xenograft line. Drug treatment start when the tumors reach to 200 mm3 size. Tumor growth and body weight is measured twice weekly. All experimental groups have a power of 83% with $p<0.05$ to detect a 35% difference in total tumor volume. The animals are harvested at eight weeks or earlier if animals become compromised (primary tumor reaching to 2000 $mm^3$, primary tumor ulcerating, or mice showing signs of pain and distress) Half of the tumor tissue is embedded in paraffin for immunohistochemical analysis and the other half flash frozen for molecular analysis. We hypothesize that blocking ERG activity in NSCLC xenografts may result in a reduction in primary tumor size.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of treating a subject having a cancer selected from the group consisting of lung cancer and glioblastoma multiforme, the method comprising administering to a subject in need thereof an effective amount of a compound having the structure:

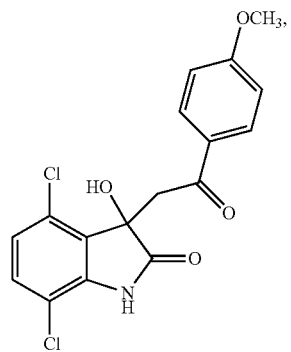 [SMILES: COc1ccc(C(=O)CC2(O)C(=O)Nc3c(Cl)ccc(Cl)c32)cc1]

or a pharmaceutically acceptable salt thereof.

2. The method of claim 1, wherein the lung cancer comprises a non-small-cell lung carcinoma.

3. The method of claim 1, wherein the lung cancer comprises a glioblastoma multiforme.

4. The method of claim 1, wherein the cancer comprises a translocation comprising an ETS gene selected from the group consisting of FLI1, ETV1, ETV4, ERG, ETS1, and ETS2.

5. The method of claim 1, wherein the compound is administered in combination with an additional chemotherapeutic agent.

6. The method of claim 1, wherein the additional chemotherapeutic agent is selected from the group consisting of cisplatin, paclitaxel, gemcitabine, etoposide, and vinblastine.

7. The method of claim 1, wherein the compound is administered parentally.

8. The method of claim 1, wherein the compound substantially consists of the (S) enantiomer.

9. The method of claim 1, wherein the compound is administered in combination with a β-hydroxypropyl cyclodextrin excipient.

10. The method of claim 1, wherein the subject is mammalian.

11. The method of claim 1, wherein the subject is human.

12. A method of inhibiting the growth of a neoplastic cell selected from the group consisting of a lung cell and a glial cell, the method comprising contacting the cell with a compound having the structure:

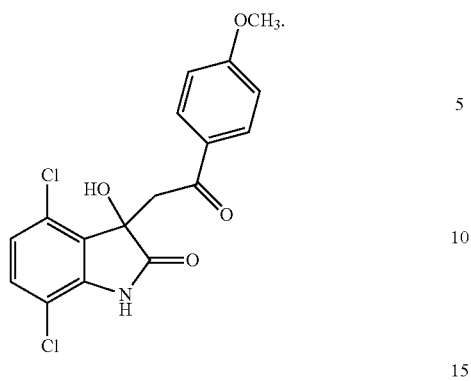

13. The method of claim 12, wherein the cell is a glioblastoma multiforme cell.

14. The method of claim 12, wherein the cell is a glioblastoma cell selected from the group consisting of a DKMG cell, a DBTRG cell, a 42MGBA cell, a GAMG cell, a U87MG cell, a H4 cell, and a 8MGBA cell.

15. The method of claim 12, wherein the cell is a non-small-cell lung carcinoma cell.

16. The method of claim 12, wherein the cell is a lung cell selected from the group consisting of a A549 cell, a H1944 cell, a H358 cell, a H1395 cell, and a H596 cell.

17. The method of claim 12, wherein the cell is in vivo.

18. The method of claim 12, wherein the cell is in vitro.

19. The method of claim 12, wherein the subject is mammalian.

20. The method of claim 12, wherein the subject is human.

* * * * *